(12) United States Patent
Dow et al.

(10) Patent No.: US 7,718,645 B2
(45) Date of Patent: May 18, 2010

(54) SUBSTITUTED BICYCLOLACTAM COMPOUNDS

(75) Inventors: Robert L. Dow, Groton, CT (US); Michael J. Munchhof, Salem, CT (US)

(73) Assignee: Pfizer Inc., New York, NY (US)

( * ) Notice: Subject to any disclaimer, the term of this patent is extended or adjusted under 35 U.S.C. 154(b) by 3 days.

(21) Appl. No.: 12/357,544

(22) Filed: Jan. 22, 2009

(65) Prior Publication Data
US 2009/0137551 A1 May 28, 2009

Related U.S. Application Data

(63) Continuation of application No. 12/174,820, filed on Jul. 17, 2008, now abandoned.

(60) Provisional application No. 60/953,507, filed on Aug. 2, 2007.

(51) Int. Cl.
C07D 267/02 (2006.01)
A61K 31/55 (2006.01)
A61P 3/10 (2006.01)
A61P 43/00 (2006.01)

(52) U.S. Cl. .................. 514/211.05; 540/490
(58) Field of Classification Search ............ 514/211.05; 540/490
See application file for complete search history.

(56) References Cited

U.S. PATENT DOCUMENTS

2005/0085469 A1   4/2005   Seto et al. ................. 514/230.5
2008/0306059 A1   12/2008   Birch et al. ............... 514/230.5

FOREIGN PATENT DOCUMENTS

WO   WO2004047755   6/2004
WO   WO2005072740   8/2005
WO   WO2007071966   6/2007

*Primary Examiner*—Bruck Kifle
(74) *Attorney, Agent, or Firm*—Jennifer Kispert; Lisa A. Samuels

(57) ABSTRACT

The invention provides compounds of formula (1),

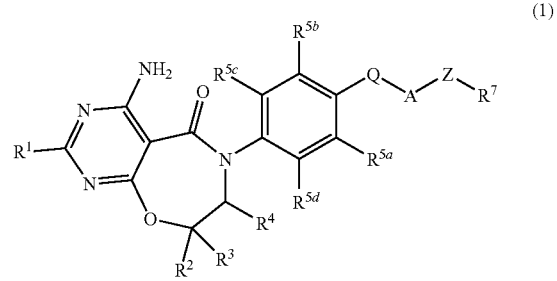

and the pharmaceutically acceptable salt thereof, wherein $R^1$, $R^2$, $R^3$, $R^4$, $R^{5a}$, $R^{5b}$, $R^{5c}$, $R^{5d}$, Q, A, Z, and $R^7$ are as described herein; compositions thereof; and uses thereof.

27 Claims, No Drawings

SUBSTITUTED BICYCLOLACTAM COMPOUNDS

FIELD OF THE INVENTION

The invention relates to substituted bicyclolactam derivatives, pharmaceutical formulations thereof, and uses thereof.

BACKGROUND OF THE INVENTION

Obesity, which is an excess of body fat relative to lean body mass, is a chronic disease that is highly prevalent in modern society. It is associated with decreased life span and numerous medical problems, including adverse psychological development, coronary artery disease, hypertension, stroke, Type 2 diabetes, hyperlipidemia, and some cancers. A hallmark characteristic of obesity is an increase in white adipose tissue (WAT) mass that is largely due to accumulation of triacylglycerol. This increase in WAT mass is a key contributor to obesity-associated complications.

Diacylglycerol O-acyltransferase 1 (DGAT-1) is a membrane-bound enzyme that catalyzes the terminal step of triacylglycerol biosynthesis. DGAT-1 is expressed in the intestine and adipose tissue It has been found that DGAT-1 null mice do not become obese when challenged with a high fat diet in contrast to wild-type littermates (Smith, et al., Nature Genetics 25:87 90, 2000). DGAT-1 null mice display reduced postprandial plasma glucose levels and exhibit increased energy expenditure, but have normal levels of serum triglycerides.

The phenotype of the DGAT-1 null mouse, along with the results of our studies with DGAT-1 inhibitors in diet-induced obese (DIO) mice, indicate that such mice are resistant to diet induced obesity and have increased insulin and leptin sensitivity. These effects suggest that inhibition of DGAT in vivo may be a novel therapeutic target not only for obesity but also for diabetes. (Subauste A, Burant C F, *Curr Drug Targets Immune Endocr Metabol Disord.* 2003 December; 3(4):263-70.)

Therefore, a need exits in the art, however, for DGAT-1 inhibitors that have efficacy for the treatment of metabolic disorders such as, for example, obesity, Type 2 diabetes and insulin resistance syndrome. Further, a need exists in the art for DGAT-1 inhibitors having $IC_{50}$ values of less than about 1000 nM and preferably below 100 nM.

SUMMARY OF THE INVENTION

The present invention relates to compounds having the structure of formula (1)

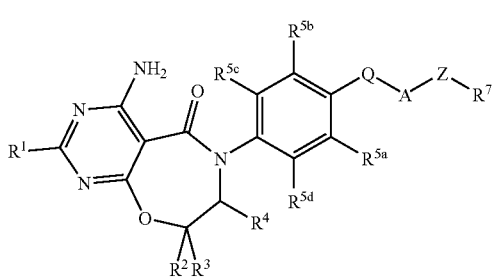

(1)

or a tautomer thereof, or a pharmaceutically acceptable salt of said compound or tautomer, wherein:

$R^1$ is H —$(C_1-C_4)$alkyl, —$(C_1-C_4)$perfluoroalkyl, —$(C_1-C_4)$perfluoroalkoxy, or —$(C_1-C_4)$alkoxy;

$R^2$ and $R^3$, taken separately, are independently H, —$(C_1-C_4)$alkyl, or —$(C_1-C_4)$perfluoroalkyl;

or $R^2$ and $R^3$, taken together with the carbon to which they are attached, is —$(C_3-C_6)$cycloalkyl;

$R^4$ is H or —$(C_1-C_4)$alkyl;

$R^{5a}$, $R^{5b}$, $R^{5c}$ and $R^{5d}$ are each independently H, F, Cl, Br, —$(C_1-C_4)$alkyl, —OH or —O—$(C_1-C_4)$alkyl;

Q is —O— or a bond;

A is a —$(C_3-C_6)$cycloalkylene group, a —$(C_3-C_6)$cycloalkenylene group or phenylene;

Z is —$C(R^{6a})(R^{6b})$— or a bond wherein $R^{6a}$ and $R^{6b}$ are each independently —H or —$(C_1-C_4)$alkyl, or $R^{6a}$ and $R^{6b}$, taken together with the carbon to which they are attached, is a —$(C_3-C_6)$cycloalkyl;

$R^7$ is $C(O)R^8$, cyano, hydroxyl, —$(C_1-C_4)$alkoxy, —$(C_1-C_4)$perfluoroalkoxy or a carboxylic acid mimic;

$R^8$ is —$OR^9$ or $NHR^{10}$;

$R^9$ is —H, —$(C_1-C_4)$alkyl, or —$(C_1-C_4)$perfluoroalkyl; and $R^{10}$ is —H, —$(C_1-C_4)$alkyl, tetrazolyl or $S(O)_2CF_3$.

The present invention also relates to a pharmaceutical composition comprising a compound of the present invention, or a pharmaceutically acceptable salt of the compound, and a pharmaceutically acceptable carrier, vehicle, diluent or excipient.

The present invention further relates to a method of treating Type 2 diabetes, insulin resistance syndrome or obesity, comprising administering to a mammal in need of such treatment a therapeutically effective amount of a compound of the present invention, or a pharmaceutically acceptable salt of the compound.

The present invention additionally relates to a method of inhibiting DGAT-1 in a mammal comprising administering to said mammal an inhibitory amount of a compound of the present invention, or a pharmaceutically acceptable salt of said compound.

The compounds, salts, and pharmaceutical compositions of the present invention are useful for the treatment of obesity, Type 2 diabetes and insulin resistance syndrome.

The compounds, salts and pharmaceutical compositions of the present invention are also useful for the treatment of impaired glucose tolerance, hyperglycemia, diabetic complications such as sugar cataracts, diabetic neuropathy, diabetic nephropathy, diabetic retinopathy and diabetic cardiomyopathy, anorexia nervosa, bulimia, cachexia, hyperuricemia, hyperinsulinemia, hypercholesterolemia, hyperlipidemia, dyslipidemia, mixed dyslipidemia, hypertriglyceridemia, nonalcoholic fatty liver disease, atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, vascular stenosis, solid tumors, skin cancer, melanoma, lymphoma, breast cancer, lung cancer, colorectal cancer, stomach cancer, esophageal cancer, pancreatic cancer, prostate cancer, kidney cancer, liver cancer, bladder cancer, cervical cancer, uterine cancer, testicular cancer and ovarian cancer.

DETAILED DESCRIPTION OF THE INVENTION

The terms used to describe the present invention have the following meanings herein.

The compounds and intermediates of the present invention may be named according to either the IUPAC (International Union for Pure and Applied Chemistry) or CAS (Chemical Abstracts Service) nomenclature systems.

The carbon atom content of the various hydrocarbon-containing moieties herein may be indicated by a prefix designating the minimum and maximum number of carbon atoms in the moiety, for example, the prefixes $(C_a\text{-}C_b)$alkyl, and $C_{a\text{-}b}$alkyl, indicate an alkyl moiety of the integer "a" to "b" carbon atoms, inclusive. Thus, for example, $(C_1\text{-}C_6)$alkyl and $C_{1\text{-}6}$alkyl refer to an alkyl group of one to six carbon atoms inclusive.

The symbol "–" represents a covalent bond.

The term "alkyl" denotes a straight or branched chain monovalent radical of an aliphatic chain of carbon atoms. Examples of alkyl groups include methyl, ethyl, propyl, iso-propyl, isobutyl, and the like.

The term "alkoxy" refers to straight or branched, monovalent radical of a saturated aliphatic chain of carbon atoms bonded to an oxygen atom that is attached to a core structure. Examples of alkoxy groups include methoxy, ethoxy and iso-propoxy.

The term "carboxylic acid mimic' refers to a mimic or bioisostere of carboxylic acid group as described in "The Practice of Medicinal Chemistry", Wermuth C. G. Ed.; Academic Press; New York, 1996, p 203. Examples of suitable carboxylic acid mimics include, but are not limited to, —$SO_3H$, —$CH_2S(O)_2R^7$, —$C(O)NHS(O)_2R^7$, —$C(O)NHOH$, —$C(O)NHCN$, —$C(O)NHR^7$, —$CH(CF_3)OH$, —$C(CF_3)_2OH$, —$P(O)(OH)_2$, 1,2,5-thiadiazol-3-ol-4-yl, 1H-tetrazole-5-yl, 1H-1,2,4-triazole-5-yl, 1H-pyrazol-5-ol-3-yl, isoxazol-5-ol-3-yl, isoxazol-3-ol-5-yl, thiazolidine-2,4-dione-5-yl, imidazolidine-2,4-dione-5-yl, 1H-pyrrole-2,5-dione-3-yl, 1H-imidazol-2-ol-5-yl, dihydropyrimidine-2,4 (1H,3H)-dione-6-yl, imidazolidine-2,4-dione-1-yl, 1H-imidazol-5-ol-2-yl, 1H-pyrazol-3-ol-1-yl, 1H-pyrazol-3-ol-4-yl, 1,3,4-thiadiazol-2-ol-5-yl, 1,3,4-oxadiazol-2-ol-5-yl, 1,2,4-oxadiazol-3-ol-5-yl, 1,2,4-thiadiazol-3-ol-5-yl, oxazol-2-ol-4-yl, thiazol-2-ol-4-yl, thiazol-4-ol-2-yl, 1,2,4-oxadiazol-5-ol-3-yl, 1,2,4-thiadiazol-5-ol-3-yl, 1,1-di-oxo-1,2,5-thiadiazolidin-3-one-2-yl, 1,1-di-oxo-1,2,5-thiadiazolidin-3-one-5-yl, isothiazol-3-ol-5-yl, 2H-1,2,3-triazol-4-ol-2-yl, 1H-1,2,3-triazol-4-ol-1-yl, 1H-imidazole-2,4-diol-5-yl, 1-oxo-2,3-dihydro-1,2,4-thiadiazol-5-ol-3-yl, thiazole-2,4-diol-5-yl, oxazole-2,4-diol-5-yl, 3,4-dihydroxyfuran-2(5H)-one-5-yl, and 5-hydroxy-1,2,4-thiadiazol-3(2H)-one-2-yl. $R^7$, as used herein, is —H, —$(C_1\text{-}C_4)$alkyl or —$(C_3\text{-}C_6)$cycloalkyl.

The term "cycloalkyl" denotes a non-aromatic, monocyclic carbocyclic radical. Examples of cycloalkyl groups include cyclopropyl, cyclobutyl, cyclopentyl, cyclohexyl. Cycloalkyl groups may be optionally fused to aromatic hydrocarbons such as benzene to form fused cycloalkyl groups, such as indanyl and the like.

The term "cycloalkylene" denotes a saturated, or partially saturated, monocyclic, bicyclic or tricyclic carbocyclic di-valent radical. Examples of cycloalkylene groups include cyclopropylene, cyclobutylene, cyclopentylene, cyclohexylene, cyclohexen-di-yl octahydropentalene-di-yl and tricycloctylene-di-yl. Cycloalkylene groups may be optionally fused to aromatic hydrocarbons such as benzene to form fused cycloalkylene groups, such as indenylene and the like.

The term "perfluoroalkyl" is defined herein as a monovalent alkyl radical wherein each hydrogen is substituted with a fluoro. Examples of perfluoroalkyl groups include, but are not limited to, trifluoromethyl, perfluoroethyl, and the like.

The term "perfluoroalkoxy" is defined herein as an alkoxy group wherein each hydrogen is substituted with a fluoro. Examples of perfluoroalkoxy groups include, but are not limited to, trifluoromethoxyl, perfluoroethoxy, and the like.

The term "radical" denotes a group of atoms that behaves as a single reactant in a chemical reaction, e.g., an organic radical is a group of atoms that imparts characteristic properties to a compound containing it, or which remains unchanged during a series of reactions, or transformations.

The term "substituted" means that a hydrogen atom on a molecule has been replaced with a different atom or molecule. The atom or molecule replacing the hydrogen atom is denoted as a "substituent."

The term "tautomer" refers to organic compounds that are interconvertible by a chemical reaction called tautomerization. Usually, the reaction involves the migration of a hydrogen atom or proton, accompanied by a switch of a single bond and adjacent double bond.

The terms "treating", "treated", or "treatment" as employed herein includes preventing (e.g., prophylaxis), palliating, slowing progression and curing a disease, such as obesity, insulin resistance syndrome, Type 2 diabetes, or a disease-related condition such as a diabetic complication.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. The phrase "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

The term "mammal" relates to an individual animal that is a member of the taxonomic class Mammalia. Examples of mammals include, but are not limited to, humans, dogs, cats, horses and cattle. In the present invention, the preferred mammals are humans, dogs and cats. More preferably, the mammal is a human.

The term "related salts" as used herein means pharmaceutically acceptable salts of compounds of the present invention.

In the present invention, it is preferred, for the compounds of formula (1), or for tautomers thereof, or for salts of said compounds or tautomers, that (a) $R^1$, $R^2$, $R^3$ and $R^4$ are each independently H or —$CH_3$; (b) $R^{5b}$ and $R^{5c}$ are each H; (c) $R^{5d}$ is H, F or Cl; (d) $R^{5a}$ is H, F, Cl or methyl; (e) Z is —$CH_2$— or a bond, and (f) $R^7$ is $C(O)R^8$ or cyano.

More preferably, Q is a bond; A is a —$(C_3\text{-}C_{10})$cycloalkylene group or a —$(C_3\text{-}C_{10})$cycloalkenylene group. $R^1$, $R^2R^3$ and $R^4$ are each independently H or —$CH_3$; $R^{5b}$ and $R^{5c}$ are each H; $R^{5d}$ is H, F or Cl; $R^{5a}$ is H, F, Cl or methyl; Z is —$CH_2$— or a bond, and $R^7$ is $C(O)R^8$ or cyano.

Even more preferably, $R^{5d}$ is H; Q is a bond; A is a —$(C_3\text{-}C_{10})$cycloalkylene group or a —$(C_3\text{-}C_{10})$cycloalkenylene group; $R^1$, $R^2$, $R^3$ and $R^4$ are each independently H or —$CH_3$; $R^{5b}$ and $R^{5c}$ are each H; $R^{5a}$ is H, F, Cl or methyl; Z is —$CH_2$— or a bond, and $R^7$ is $C(O)R^8$ or cyano.

Yet even more preferably A is 1,4-cyclohexylene, cyclohex-3-en-1,4-di-yl, tricyclo[3.2.1.0~2,4~]octylene-1,3-di-yl or octahydropentalene-1,4-di-yl; $R^{5d}$ is H; Q is a bond; $R^1$, $R^2$, $R^3$ and $R^4$ are each independently H or —$CH_3$; $R^{5b}$ and $R^{5c}$ are each H; $R^{5a}$ is H, F, Cl or methyl; Z is —$CH_2$— or a bond, and $R^7$ is $C(O)R^8$ or cyano.

Most preferably, the compounds or formula (1), tautomers thereof, and salts of the compounds or tautomers, include compounds having the structure of formula (2)

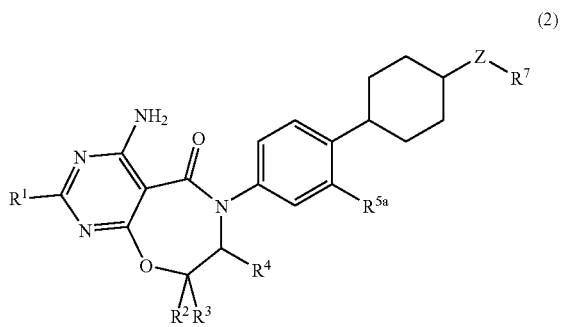

(2)

or a tautomer thereof, or a pharmaceutically acceptable salt of said compound or tautomer, wherein: $R^1$ is H or —$CH_3$; $R^2$ is H or —$CH_3$; $R^3$ is H or —$CH_3$; $R^4$ is H or —$CH_3$; $R^{5a}$ is H, F, Cl or methyl; Z is —C($R^{6a}$)($R^{6b}$)— or a bond wherein $R^{6a}$ and $R^{6b}$ are each independently-H or —($C_1$-$C_4$)alkyl, or $R^{6a}$ and $R^{6b}$, taken together with the carbon to which they are attached, is a —($C_3$-$C_6$)cycloalkyl; $R^7$ is C(O)$R^8$, cyano, hydroxyl, —($C_1$-$C_4$)alkoxy, —($C_1$-$C_4$)-perfluoroalkoxy or a carboxylic acid mimic; $R^8$ is —O$R^9$ or NH$R^{10}$; $R^9$ is —H, —($C_1$-$C_4$)alkyl, or —($C_1$-$C_4$)perfluoroalkyl; and $R^{10}$ is —H, —($C_1$-$C_4$)alkyl, tetrazolyl or S(O)$_2$CF$_3$. Preferably, Z is —$CH_2$—.

In the present invention, it is preferred, for the compounds of formula (2), or for tautomers thereof, or for salts of said compounds or tautomers, that Z is —$CH_2$—.

In one preferred embodiment of the compounds of formula (2), or the tautomers thereof, or the salts of said compounds or tautomers, Z is —$CH_2$— and $R^7$ is —C(O)NH$R^{10}$.

In a second preferred embodiment of the compounds of formula (2), or the tautomers thereof, or the salts of said compounds or tautomers, Z is —$CH_2$— and $R^7$ is —CN. A preferred compound of this embodiment is {trans-4-[4-(4-amino-5-oxo-7,8-dihydropyrimido[5,4-f][1,4]oxazepin-6(5H)-yl)phenyl]cyclohexyl}acetonitrile, or a tautomer thereof, or a salt of said compound or tautomer.

In a third preferred embodiment of the compounds of formula (2), or the tautomers thereof, or the salts of said compounds or tautomers, Z is —$CH_2$— and $R^7$ is —C(O)OH. One preferred compound of this embodiment is 2-(4-(4-(4-amino-5-oxo-7,8-dihydropyrimido[5,4-f][1,4]oxazepin-6(5H)-yl)-2-fluorophenyl)cyclohexyl)acetic acid, or a tautomer thereof, or a salt of said compound or tautomer. Another preferred compound of this embodiment is {trans-4-[4-(4-amino-5-oxo-7,8-dihydropyrimido[5,4-f][1,4]-oxazepin-6(5H)-yl)phenyl]cyclohexyl}acetic acid, or a tautomer thereof, or a salt of said compound or tautomer.

In a fourth preferred embodiment of the compounds of formula (2), or the tautomers thereof, or the salts of said compounds or tautomers, Z is —$CH_2$— and $R^2$ is (R)-methyl. For this embodiment, it is more preferred that $R^7$ is —C(O)NH$R^{10}$, —CN, or —C(O)OH. A preferred compound of this embodiment is (trans-4-{4-[(8R)-4-amino-8-methyl-5-oxo-7,8-dihydropyrimido[5,4-f][1,4]oxazepin-6(5H)-yl]phenyl}cyclohexyl)acetonitrile, or a tautomer thereof, or a salt of said compound or tautomer. Another preferred compound of this embodiment is (trans-4-{4-[(8R)-4-amino-8-methyl-5-oxo-7,8-dihydropyrimido-[5,4-f][1,4]oxazepin-6(5H)-yl]phenyl}cyclohexyl)acetic acid, or a tautomer thereof, or a salt of said compound or tautomer. Yet another preferred compound of this embodiment is (R)-2-(4-(4-(4-amino-8-methyl-5-oxo-7,8-dihydro-pyrimido[5,4-f][1,4]ox-azepin-6(5H)-yl)-2-fluorophenyl)cyclohexyl)acetic acid, or a tautomer thereof, or a salt of said compound or tautomer.

Wherein a compound of formula (I) contains an alkenyl or alkenylene group, geometric cis/trans (or Z/E) isomers are possible. Cis/trans isomers may be separated by conventional techniques well known to those skilled in the art, for example, chromatography and fractional crystallization.

When the compounds of the present invention contain one or more stereogenic centers, said compounds may be resolved into the pure enantiomers by methods known to those skilled in the art, for example by formation of stereoisomeric salts which may be separated, for example, by crystallization; formation of stereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, the specific stereoisomers may be synthesized by using an optically active starting material, by asymmetric synthesis using optically active reagents, substrates, catalysts or solvents, or by converting one stereoisomer into the other by asymmetric transformation.

Certain compounds of formula (1) may exist in different stable conformational forms which may be separable. Torsional asymmetry due to restricted rotation about an asymmetric single bond, for example because of steric hindrance or ring strain, may permit separation of different conformers. The compounds of the present invention further include each conformational isomer of compounds of formula (1) and mixtures thereof.

It follows that a single compound may exhibit more than one type of isomerism. Included within the scope of the claimed compounds present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

The compounds of the present invention, and the salts thereof, may exist in unsolvated as well as solvated forms with pharmaceutically acceptable solvents such as water, ethanol, and the like. The term 'solvate' is used herein to describe a molecular complex comprising the compound of the invention and one or more pharmaceutically acceptable solvent molecules, for example, ethanol. The term 'hydrate' is employed when said solvent is water.

Pharmaceutically acceptable solvates include hydrates and other solvates wherein the solvent of crystallization may be isotopically substituted, e.g. $D_2O$, $d_6$-acetone, $d_6$-DMSO. The compounds of the present invention may exist as clathrates or other complexes.

Certain compounds of formula (1) and their salts and solvates may exist in more than one crystal form. Polymorphs of compounds represented by formula (1) form part of this invention and may be prepared by crystallization of a compound of formula (1) under different conditions. For example, using different solvents or different solvent mixtures for recrystallization; crystallization at different temperatures; various modes of cooling, ranging from very fast to very slow cooling during crystallization. Polymorphs may also be obtained by heating or melting a compound of formula (1) followed by gradual or fast cooling. The presence of polymorphs may be determined by solid probe NMR spectroscopy, IR spectroscopy, differential scanning calorimetry, powder X-ray diffraction or such other techniques.

This invention also includes isotopically-labeled compounds, which are identical to those described by formula (2), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur and fluorine, such as $^2$H, $^3$H, $^{13}$C, $^{14}$C, $^{15}$N, $^{18}$O, $^{17}$O, $^{35}$S, $^{36}$Cl, $^{125}$I, $^{129}$I, and $^{18}$F respectively. Compounds of the present invention, and pharmaceutically acceptable salts of the compounds which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated (i.e., $^3$H), and carbon-14 (i.e., $^{14}$C), isotopes are particularly preferred for their ease of preparation and detectability. Further, substitution with heavier isotopes such as deuterium (i.e., $^2$H), can afford certain therapeutic advantages resulting from greater metabolic stability, for example increased in vivo half-life or reduced dosage requirements and, hence, may be preferred in some circumstances. Isotopically labeled compounds of formula (2) of this invention, and salts thereof can generally be prepared by carrying out the procedures disclosed in the schemes and/or in the Examples below, by substituting a readily available isotopically labeled reagent for a non-isotopically labeled reagent.

Pharmaceutically acceptable salts, as used herein in relation to compounds of the present invention, include pharmaceutically acceptable inorganic and organic salts of said compound. These salts can be prepared in situ during the final isolation and purification of a compound, or by separately reacting the compound or prodrug thereof, with a suitable organic or inorganic acid and isolating the salt thus formed. Representative salts include, but are not limited to, the acetate, aspartate, benzoate, besylate, bicarbonate, dimesylate, diphosphate, bisulfate, bitartrate, bromide, camsylate, carbonate, chloride, citrate, edisylate, esylate, fumarate, gluceptate, hemifumarate, hydrobromide, hydrochloride, isethionate, lactate, malate, maleate, mesylate, napsylate, nitrate, oxalate, palmitate, pamoate, phosphate, saccharate, stearate, succinate, sulfate, tartrate, tosylate, and trifluoroacetate salts.

These may also include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, diethylamine and the like. For additional examples see, Berge, et al., J. Pharm. Sci., 66, 1-19 (1977) and "Handbook of Pharmaceutical Salts: Properties, Selection, and Use" by Stahl and Wermuth (Wiley-VCH, Weinheim, Germany, 2002).

The compounds of the present invention may be isolated and used per se or in the form of their pharmaceutically acceptable salts. In accordance with the present invention, compounds with multiple basic nitrogen atoms can form salts with varying number of equivalents ("eq.") of acid. It will be understood by practitioners that all such salts are within the scope of the present invention.

The present invention further includes prodrugs of compounds of formula (1). A prodrug of a compound of formula (1) may be one formed in a conventional manner with a functional group of the compound, such as with an amino, hydroxy or carboxy group. The term "prodrug" means a compound that is transformed in vivo to yield a compound of formula (1) or a pharmaceutically acceptable salt of the compound. The transformation may occur by various mechanisms, such as through hydrolysis in blood. A discussion of the use of prodrugs is provided by T. Higuchi and W. Stella, "Pro-drugs as Novel Delivery Systems,"Vol. 14 of the A.C.S. Symposium Series, and in Bioreversible Carriers in Drug Design, ed. Edward B. Roche, American Pharmaceutical Association and Pergamon Press, 1987.

For example, as all of the compounds of the present invention incorporate an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$) alkyl, ($C_3$-$C_7$)cycloalkyl, benzyl, or R-carbonyl is a natural α-aminoacyl or natural α-aminoacyl-natural α-aminoacyl, —C(OH)C(O)OY' wherein Y' is H, ($C_1$-$C_6$)alkyl or benzyl, —C(OY$_0$)Y$_1$ wherein Y$_0$ is ($C_1$-$C_4$) alkyl and Y$_1$ is ($C_1$-$C_6$) alkyl, carboxy($C_1$-$C_6$)alkyl, amino($C_1$-$C_4$)alkyl or mono-N— or di-N,N—($C_1$-$C_6$)alkylaminoalkyl, —C(Y$_2$)Y$_3$ wherein Y$_2$ is H or methyl and Y$_3$ is mono-N— or di-N,N—($C_1$-$C_6$)alkylamino, morpholino, piperidin-1-yl or pyrrolidin-1-yl.

Similarly, if a compound of the present invention contains an alcohol functional group, a prodrug can be formed by the replacement of the hydrogen atom of the alcohol group with a group such as ($C_1$-$C_6$)alkanoyloxy-methyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O)($C_1$-$C_6$)alkyl)$_2$ or glycosyl (the radical resulting from the removal of a hydroxyl group of the hemiacetal form of a carbohydrate).

If a compound of the present invention contains a carboxylic acid functional group, a prodrug can comprise an ester formed by the replacement of the hydrogen atom of the acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyl-oxy)ethyl having from 4 to 7 carbon atoms, 1-methyl-1-(alkoxycarbonyloxy)-ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$) alkylcarbamoyl-($C_1$-$C_2$)alkyl and piperidino-, pyrrolidino- or morpholino($C_2$-$C_3$)alkyl.

Synthesis

In general, the compounds of formula (1) of this invention may be prepared by methods that include processes known in the chemical arts, particularly in light of the description contained herein. Certain processes for the manufacture of the compounds of formula (1) of this invention are illustrated by the following reaction schemes. Other processes are described in the experimental section. Some of the starting compounds for the reactions described in the schemes and Examples are prepared as illustrated herein.

In Schemes 1, 3 and 4 below, generalized methods for preparing the compounds of formula (1) are depicted.

Scheme 1
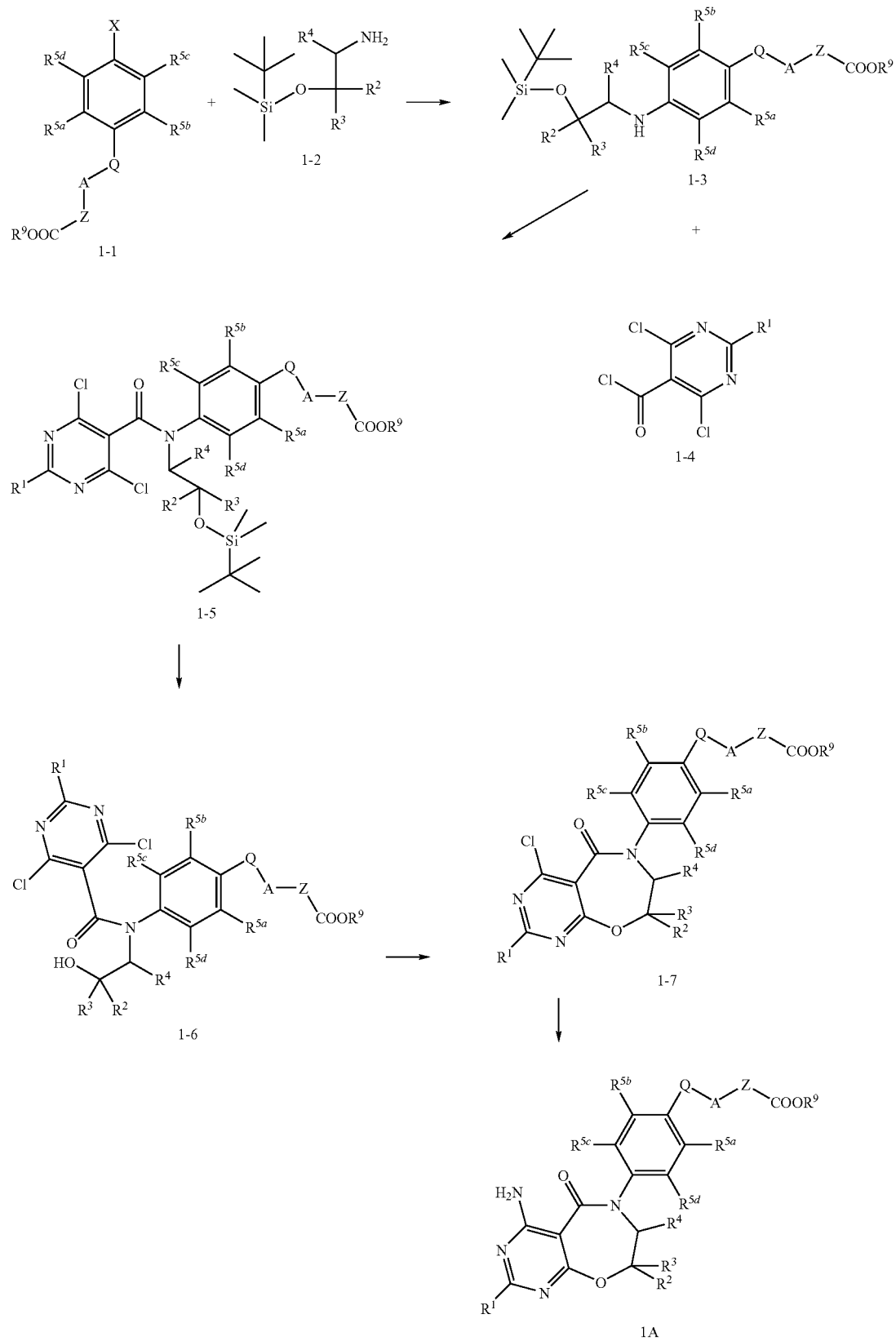

In Scheme 1, aryl halide/sulfonates 1-1 can be prepared beginning with commercially available starting materials and using general synthetic techniques known to those skilled in the arts. Additional support for the preparation of intermediates such as 1-1, wherein X is a halide or $OSO_2R$, are provided in U.S. Pat. No. 7,244,727, issued Jul. 17, 2007, the teachings of which are incorporated herein, by reference, in their entirety. Compound 1-2 was prepared by the method of C. Palomo et al., Synthesis of β-Lactam Scaffolds for Ditopic Peptidomimetics, *Organic Letters* (2007), 9(1), pages 101-104. Compounds 1-1 and 1-2 can be coupled using a metal catalyst, such as palladium or copper to form Compound 1-3. More specifically, 1-1 and 1-2 are heated to a temperature between 80° C. to 130° C. in a solvent, such as toluene, with cesium carbonate, palladium acetate and 2-dicyclohexyl phosphino-2',4',6'-triisopropylbiphenyl (X-PHOS) under nitrogen for about 15-20 hours to form Compound 1-3.

Compound 1-3 is acylated with 1-4 using conditions and reagents known to the skilled artisan (utilizing a mild base, such as triethylamine or pyridine) to afford compound 1-5. Compound 1-4 is prepared by the method of Tarasov, Evgeniy V.; Henckens, Anja; Ceulemans, Erik; Dehaen, Wim. A short total synthesis of cerpegin by intramolecular hetero Diels-Alder cycloaddition reaction of an acetylene tethered pyrimidine. Synlett (2000), (5), 625-626. The protecting group (Pg) present in compound 1-5 can be removed by one skilled in the art, utilizing conditions referenced in Greene's Protective Groups in Organic Synthesis, 4$^{th}$ Ed., P. G. M Wuts and T. W. Greene, Wiley-Interscience to afford compound 1-6. In the case where Pg=t-butyldimethyl-silyl, deprotection can be accomplished by a range of conditions including acidic and fluoride-based conditions. Preferred conditions when Pg is t-butyldimethylsilyl are dilute aqueous hydrochloric acid in methanol at ambient temperature for 2-10 hours. Cyclization of compound 1-6 to afford compound 1-7 can be accomplished utilizing a wide range of basic conditions, including organic (e.g. triethylamine) and inorganic (e.g. potassium carbonate) as the bases, in an aprotic solvent at 20° C. to 120° C. to provide the cyclic lactam structure 1-7. Preferred conditions for this cyclization are triethylamine in acetonitrile at 40° C. to 120° C. for 4-16 hours. Amination of compound 1-7 can be accomplished with ammonia in a range of aprotic or protic solvents at 0° C. to 100° C. for 4-20 hours. Preferred conditions are ammonia in p-dioxane at ambient temperature for 4 to 24 hours.

Compounds of formula (1), which contain a carboxylic ester functionality, can be hydrolyzed to the corresponding carboxylic acid utilizing base or acid catalyzed hydrolysis conditions as known in the art. A preferred method of hydrolysis is treating compound (1) with aqueous lithium hydroxide in an organic solvent at 20° C. to 100° C. for 1 to 10 hours.

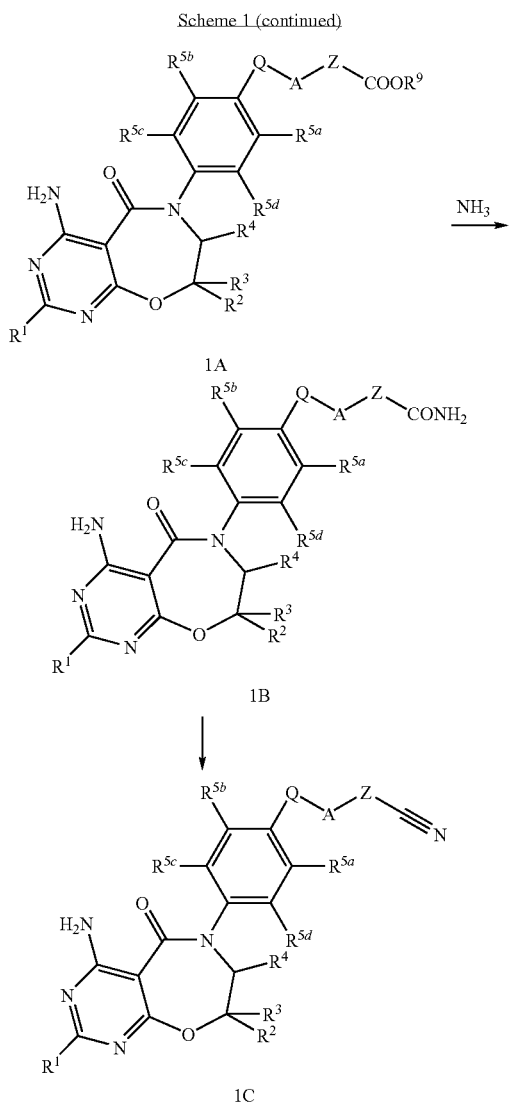

Compound 1B may be formed through a peptide coupling reaction between Compound 1A and ammonia. Compound 1B may be used to form Compound 1C by amide dehydration The dehydration may be performed by treating the amide with $SOCl_2$, $POCl_3$, $PCl_5$, p-TosCl/pyridine, $Tf_2O$/pyridine or with the Vilsmeier reagent in combination with an organic or inorganic base. The Vilsmeier reagent can be prepared by reacting dimethylformamide (DMF) with oxalylchloride in acetonitrile, dichloromethane, chloroform, dioxane, tetrahydrofuran (THF), or diethylether. In a general procedure, the Vilsmeier reagent is formed in the desired solvent for instance at a temperature between 0° C. and room temperature. The formation normally will be completed in 5-15 minutes. In a preferred embodiment a solution of the amide in the desired solvent is added dropwise to the Vilsmeier reagent at a temperature between 0° C. and room temperature. The addition normally will be completed in 10-20 minutes. For the formation of the nitrile, two equivalents of a base are added. Preferably an organic base, for instance pyridine or triethylamine (TEA) is used. Inorganic bases may also be effective.

Scheme 2
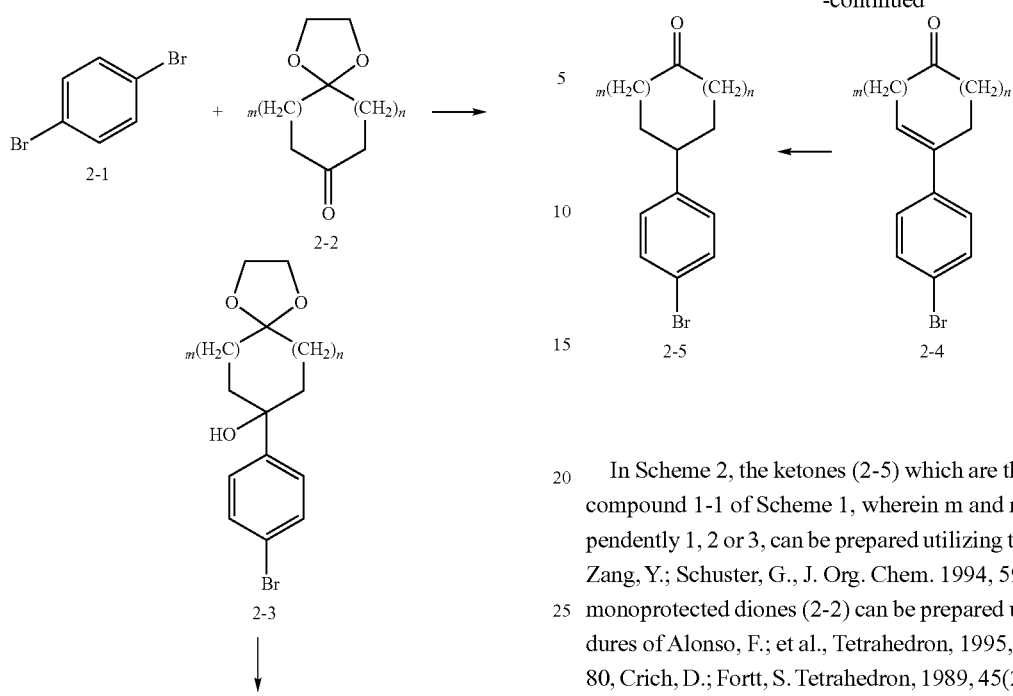
In Scheme 2, the ketones (2-5) which are the equivalent of compound 1-1 of Scheme 1, wherein m and n are each independently 1, 2 or 3, can be prepared utilizing the procedure of Zang, Y.; Schuster, G., J. Org. Chem. 1994, 59, 1855-62. The monoprotected diones (2-2) can be prepared using the procedures of Alonso, F.; et al., Tetrahedron, 1995, 51(37), 10259-80, Crich, D.; Fortt, S. Tetrahedron, 1989, 45(20), 6581-98, or Lee, S.; Fuchs, P., J. Amer. Chem. Soc., 2002, 124, 13978-9.
Scheme 3
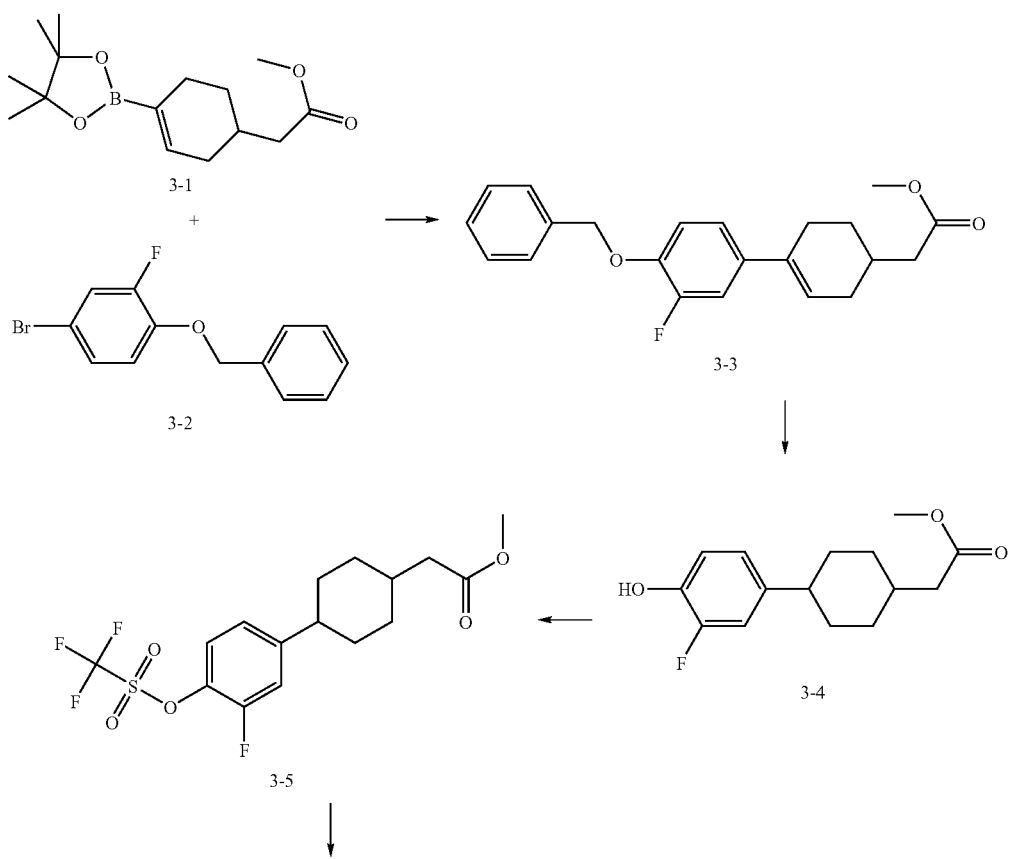

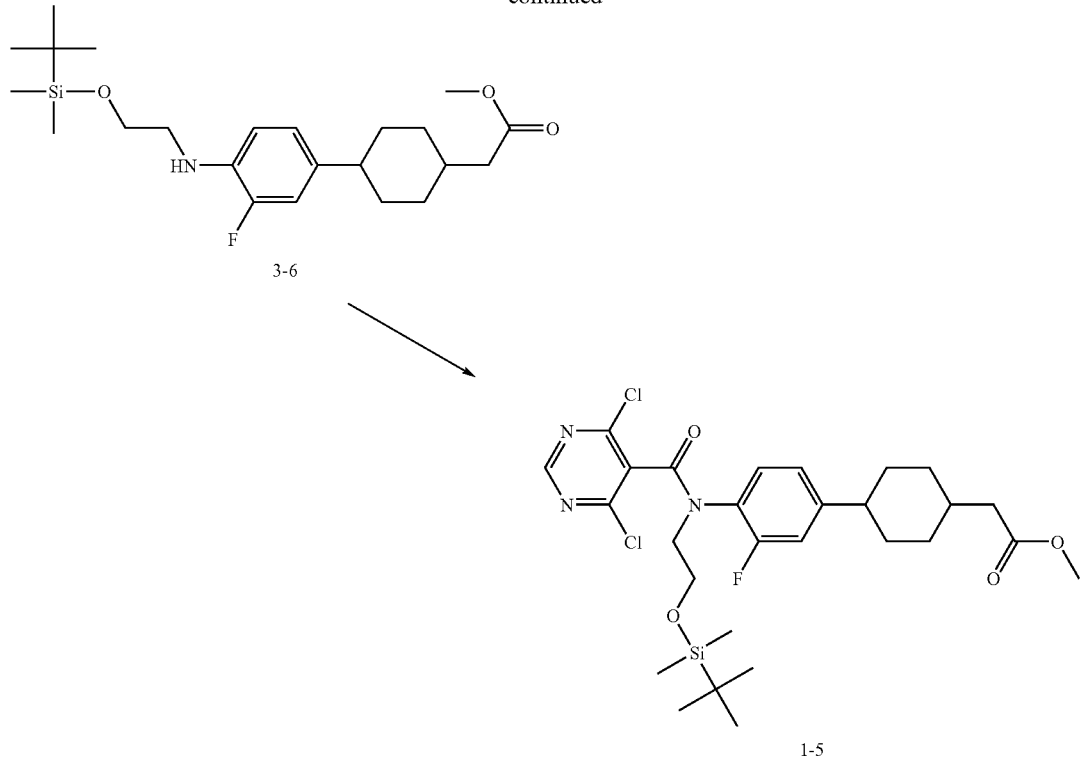
In Scheme 3, compound 1-5, and analogues thereto, may be prepared from compounds 3-1 and 3-2 as described in the following Preparation 4 and through methods known in the art.
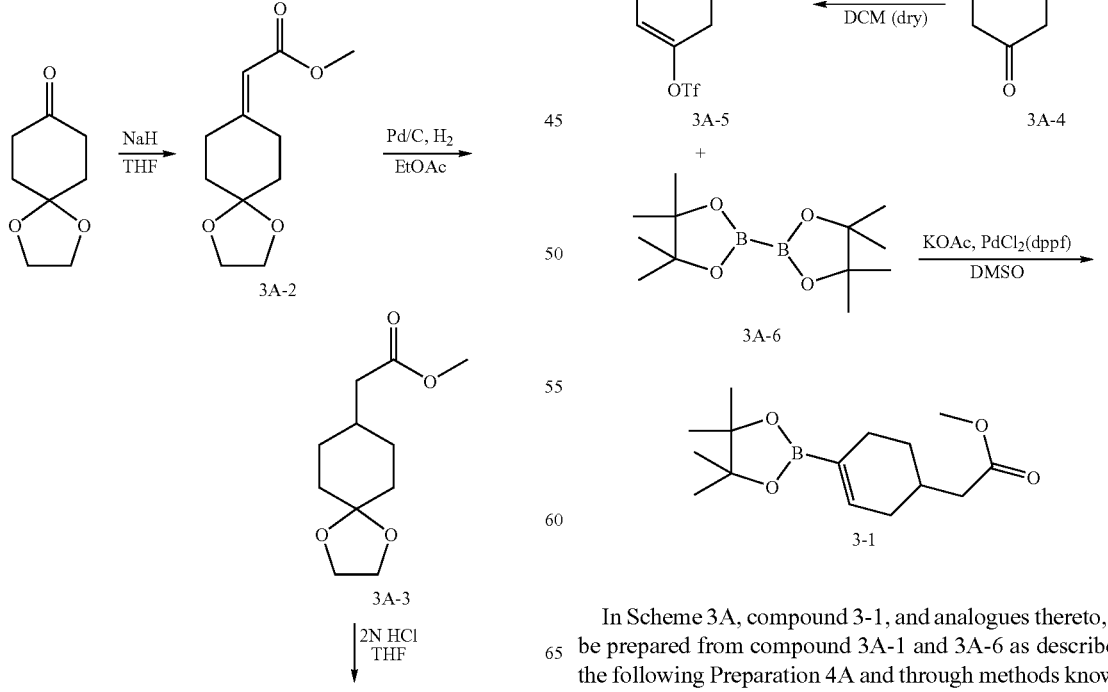
In Scheme 3A, compound 3-1, and analogues thereto, may be prepared from compound 3A-1 and 3A-6 as described in the following Preparation 4A and through methods known in the art.

Alternatively, in Scheme 4, compounds of formula (1) may also be prepared from compound 4-7, which is prepared by the method of Scheme 3 above, through methods known in the art.

and a pharmaceutically acceptable carrier, vehicle, diluent or excipient. A preferred pharmaceutical composition of the present invention comprises a therapeutically effective amount of a compound of formula (2), or a pharmaceutically

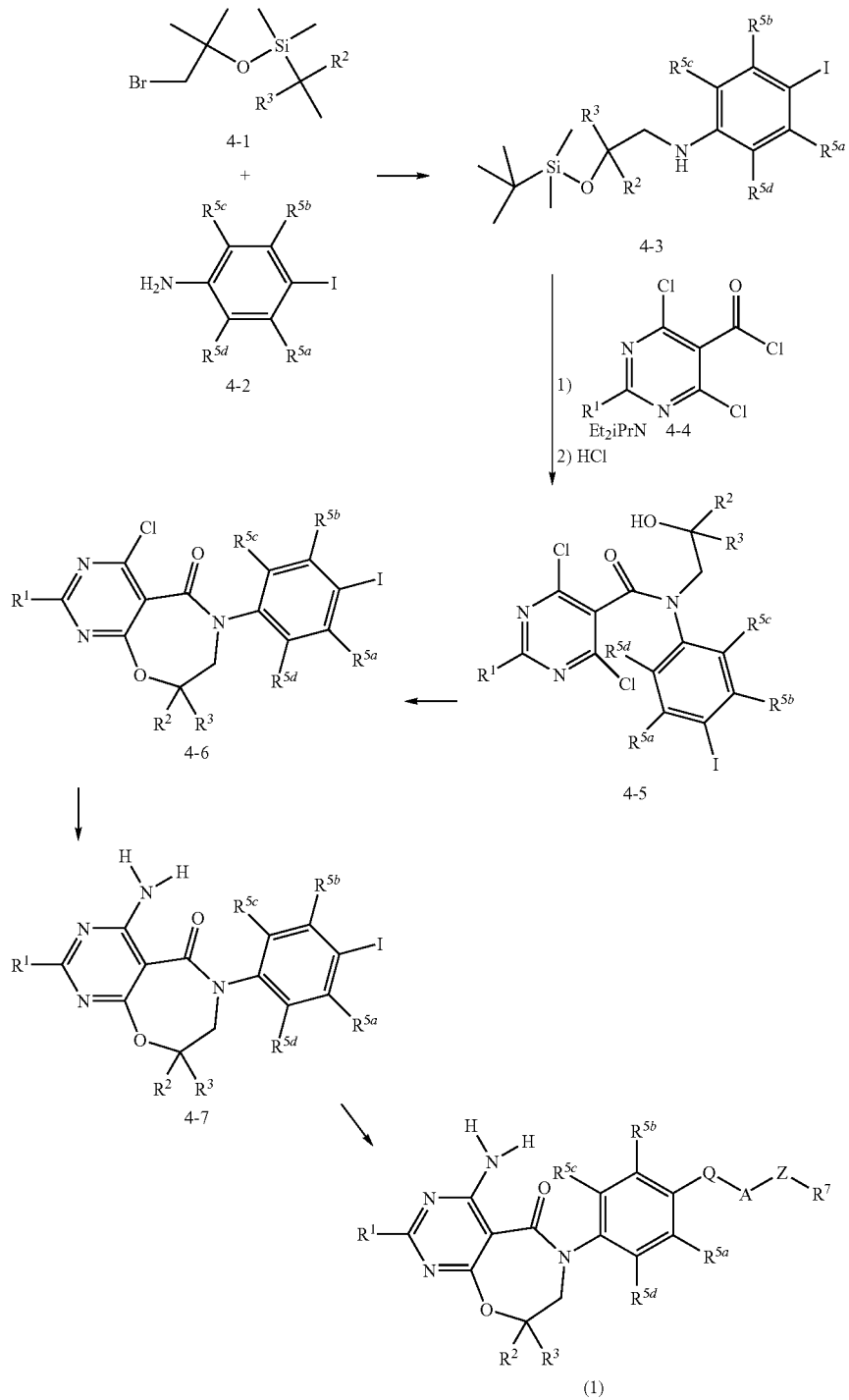

A pharmaceutical composition of the present invention comprises a therapeutically effective amount of a compound of formula (1) or a pharmaceutically acceptable salt thereof, acceptable salt thereof, and a pharmaceutically acceptable carrier, vehicle, diluent or excipient. Even more preferably, the pharmaceutical composition contains {trans-4-[4-(4- amino-5-oxo-7,8-dihydropyrimido[5,4-f][1,4]oxazepin-6
(5H)-yl)phenyl]cyclohexyl}-acetonitrile or a pharmaceutically acceptable salt thereof, 2-(4-(4-(4-amino-5-oxo-7,8-dihydropyrimido[5,4-f][1,4]oxazepin-6(5H)-yl)-2-fluorophenyl)-cyclohexyl)acetic acid or a pharmaceutically acceptable salt thereof, {trans-4-[4-(4-amino-5-oxo-7,8-dihydropyrimido[5,4-f][1,4]-oxazepin-6(5H)-yl)phenyl]-cyclohexyl}acetic acid or a pharmaceutically acceptable salt thereof, (trans-4-{4-[(8R)-4-amino-8-methyl-5-oxo-7,8-dihydropyrimido[5,4-f][1,4]oxazepin-6(5H)-yl]
phenyl}cyclohexyl)acetonitrile or a pharmaceutically acceptable salt thereof, (trans-4-{4-[(8R)-4-amino-8-methyl-5-oxo-7,8-dihydropyrimido[5,4-f]-[1,4]oxazepin-6(5H)-yl]
phenyl}cyclohexyl)acetic acid or a pharmaceutically acceptable salt thereof, or (R)-2-(4-(4-(4-amino-8-methyl-5-oxo-7,8-dihydro-pyrimido[5,4-f][1,4]oxazepin-6(5H)-yl)-2-fluorophenyl)-cyclohexyl)acetic acid or a pharmaceutically acceptable salt thereof; and a pharmaceutically acceptable carrier, vehicle, diluent or excipient.

The pharmaceutical compositions formed by combining the compounds of this invention and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like.

Thus, for purposes of oral administration, tablets containing various excipients such as sodium citrate, calcium carbonate and/or calcium phosphate, may be employed along with various disintegrants such as starch, alginic acid and/or certain complex silicates, together with binding agents such as polyvinylpyrrolidone, sucrose, gelatin and/or acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the active pharmaceutical agent therein may be combined with various sweetening or flavoring agents, coloring matter or dyes and, if desired, emulsifying or suspending agents, together with diluents such as water, ethanol, propylene glycol, glycerin and/or combinations thereof.

For parenteral administration, solutions of the compounds or compositions of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

For intranasal administration or administration by inhalation, the compounds or compositions of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of a compound of this invention.

Capsules and cartridges (made, for example, from gelatin) for use in an inhaler or insufflator may be formulated containing a powder mix of a compound or compounds of the invention and a suitable powder base such as lactose or starch.

Methods of preparing various pharmaceutical compositions with a certain amount of active ingredient are known, or will be apparent in light of this disclosure, to those skilled in this art. For examples of methods of preparing pharmaceutical compositions, see Remington's Pharmaceutical Sciences, Mack Publishing Company, Easton, Pa., 19th Edition (1995).

In another aspect, the invention is directed to a pharmaceutical composition, which comprises a therapeutically effective amount of a first compound of formula (1), or a pharmaceutically acceptable salt of the compound; a second compound that is an antidiabetic agent selected from insulin and insulin analogs; insulinotropin; biguanides; $\alpha_2$-antagonists and imidazolines; glitazones; aldose reductase inhibitors; glycogen phosphorylase inhibitors; sorbitol dehydrogenase inhibitors; fatty acid oxidation inhibitors; $\alpha$-glucosidase inhibitors; $\beta$-agonists; phosphodiesterase inhibitors; lipid-lowering agents; antiobesity agents; vanadate and vanadium complexes and peroxovanadium complexes; amylin antagonists; glucagon antagonists; growth hormone secretagogues; gluconeogenesis inhibitors; somatostatin analogs; antilipolytic agents; a prodrug of the antidiabetic agents, or a pharmaceutically acceptable salt of the antidiabetic agents and the prodrugs.

In another aspect, the invention is directed to a kit comprising: a first dosage form comprising a compound of formula (1), or a pharmaceutically acceptable salt of the compound; and a second dosage form comprising an antidiabetic agent selected from insulin and insulin analogs; insulinotropin; biguanides; $\alpha_2$-antagonists and imidazolines; glitazones; aldose reductase inhibitors; glycogen phosphorylase inhibitors; sorbitol dehydrogenase inhibitors; fatty acid oxidation inhibitors; $\alpha$-glucosidase inhibitors; $\beta$-agonists; phosphodiesterase inhibitors; lipid-lowering agents; antiobesity agents; vanadate and vanadium complexes and peroxovanadium complexes; amylin antagonists; glucagon antagonists; growth hormone secretagogues; gluconeogenesis inhibitors; somatostatin analogs; antilipolytic agents; prodrugs of the antidiabetic agents, or a pharmaceutically acceptable salts of the antidiabetic agents and the prodrug; and a container for containing said first dosage (a) and said second dosage (b). In a preferred embodiment of the kit, both the first and the second dosage forms independently comprise a pharmaceutically acceptable carrier or diluent.

In another aspect, the invention is directed to a method of inhibiting DGAT-I comprising administering to a mammal an inhibitory amount of a compound of formula (1), or a pharmaceutically acceptable salt of the compound, either alone or in combination with an antidiabetic agent as described above.

In another aspect, the invention is directed to a method of treating a condition mediated by DGAT-1 inhibition comprising administering to a mammal in need of such treatment a therapeutically effective amount of a compound of formula (1), or a pharmaceutically acceptable salt of the compound, either alone or in combination with an antidiabetic agent as described above.

In the present invention, typically, the condition treated is Type 2 diabetes, insulin resistance syndrome or obesity. Preferably, the condition is treated by administering a compound of formula (2), or a pharmaceutically acceptable salt thereof. More preferably, the condition is treated by administering one of the following compounds, or pharmaceutically acceptable salts thereof: {trans-4-[4-(4-amino-5-oxo-7,8-dihydropyrimido[5,4-f][1,4]oxazepin-6(5H)-yl)phenyl]cyclohexyl}-acetonitrile, 2-(4-(4-(4-amino-5-oxo-7,8-dihydro-pyrimido[5,4-f][1,4]oxazepin-6(5H)-yl)-2-fluorophenyl)-cyclohexyl) acetic acid, {trans-4-[4-(4-amino-5-oxo-7,8-dihydropyrimido[5,4-f][1,4]-oxazepin-6(5H)-yl)phenyl]-cyclohexyl}acetic acid, (trans-4-{4-[(8R)-4-amino-8-methyl-5-oxo-7,8-dihydropyrimido[5,4-f][1,4]oxazepin-6 (5H)-yl]phenyl}cyclohexyl) acetonitrile, (trans-4-{4-[(8R)-4-amino-8-methyl-5-oxo-7,8-dihydropyrimido[5,4-f]-[1,4] oxazepin-6(5H)-yl]phenyl}cyclohexyl)acetic acid, or (R)-2-(4-(4-(4-amino-8-methyl-5-oxo-7,8-dihydro-pyrimido[5,4-f][1,4]oxazepin-6(5H)-yl)-2-fluorophenyl)-cyclohexyl) acetic acid.

Preferably, the mammal treated is a human.

In an alternate embodiment, the condition treated is impaired glucose tolerance, hyperglycemia, diabetic complications such as sugar cataracts, diabetic neuropathy, diabetic nephropathy, diabetic retinopathy and diabetic cardiomyopathy, anorexia nervosa, bulimia, cachexia, hyperuricemia, hyperinsulinemia, hypercholesterolemia, hyperlipidemia, dyslipidemia, mixed dyslipidemia, hypertriglyceridemia, nonalcoholic fatty liver disease, atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, vascular stenosis, solid tumors, skin cancer, melanoma, lymphoma, breast cancer, lung cancer, colorectal cancer, stomach cancer, esophageal cancer, pancreatic cancer, prostate cancer, kidney cancer, liver cancer, bladder cancer, cervical cancer, uterine cancer, testicular cancer and ovarian cancer.

The present invention also relates to therapeutic methods for treating the above described conditions in a mammal, including a human, wherein a compound of formula (1) of this invention is administered as part of an appropriate dosage regimen designed to obtain the benefits of the therapy. The appropriate dosage regimen, the amount of each dose administered and the intervals between doses of the compound will depend upon the compound of formula (1) of this invention being used, the type of pharmaceutical compositions being used, the characteristics of the subject being treated and the severity of the conditions.

In general, an effective dosage for the compounds of the present invention is in the range of 0.01 mg/kg/day to 30 mg/kg/day, preferably 0.01 mg/kg/day to 5 mg/kg/day of active compound in single or divided doses. Some variation in dosage will necessarily occur, however, depending on the condition of the subject being treated. The individual responsible for dosing will, in any event, determine the appropriate dose for the individual subject. Practitioners will appreciate that "kg" refers to the weight of the patient measured in kilograms.

The compounds or compositions of this invention may be administered in single (e.g., once daily) or multiple doses or via constant infusion. The compounds of this invention may also be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents.

The compounds or compositions of the present invention may be administered to a subject in need of treatment by a variety of conventional routes of administration, including orally and parenterally, (e.g., intravenously, subcutaneously or intramedullary). Further, the pharmaceutical compositions of this invention may be administered intranasally, as a suppository, or using a "flash" formulation, i.e., allowing the medication to dissolve in the mouth without the need to use water.

EXEMPLIFICATION

The Examples set forth herein below are for illustrative purposes only. The compositions, methods, and various parameters reflected herein are intended only to exemplify various aspects and embodiments of the invention, and are not intended to limit the scope of the claimed invention in any way.

The abbreviations used in the exemplification are defined as follows:
DCM is dichloromethane,
DMF is dimethylformamide,
DPPF is 1,1'-Bis(diphenylphosphino)ferrocene,
EDCI is 1-ethyl-3-(3-dimethylaminopropyl)carbodiimide,
EtOAc is ethyl acetate,
HCl is hydrochloric acid,
HOBt is N-hydroxybenzotriazole,
MTHF is 2-Methyltetrahydrofuran,
RT is retention time in minutes,
TEA is triethylamine,
TFA is trifluoroacetic acid,
Tf$_2$O is Trifluoromethanesulfonic (triflic) anhydride,
THF is tetrahydrofuran, and
X-PHOS is 2-dicyclohexyl phosphino-2',4',6'-triisopropylbiphenyl.

Unless noted otherwise, all reactants were obtained commercially.

Unless otherwise noted, purifications were performed using a Biotage® SNAP FLASH purification cartridge (silica gel).

All Combiflash® purifications, discussed herein, were performed using a CombiFlash® Companion system (Teledyne Isco; Lincoln, Nebr.) utilizing packed RediSep® silica columns.

Mass Spectra were recorded on a Waters® (Waters Corp.; Milford, Mass.) Micromass® Platform II spectrometer. Unless otherwise specified, mass spectra were recorded on a Waters® (Milford, Mass.) Micromass® Platform II spectrometer.

Proton NMR chemical shifts are given in parts per million downfield from tetramethylsilane and were recorded on a Varian Unity 400 MHz (megaHertz) spectrometer (Varian Inc.; Palo Alto, Calif.).

The compounds of the present invention, described in Examples 1-48, were prepared, or subsequently derived from a compound prepared, by the method of Scheme I using the compounds of Preparations 1, 2, 3 or 4.

Preparation 1

Methyl {trans-4-[4-(4-chloro-5-oxo-7,8-dihydropyrimido[5,4-f][1,4]oxazepin-6-(5H)-yl)phenyl] cyclohexyl}acetate

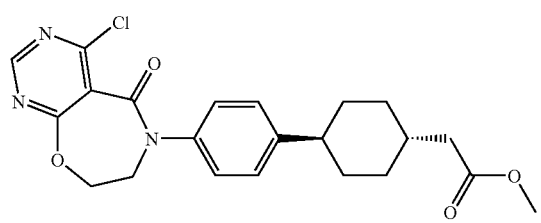

Methyl {trans-4-[4-(4-chloro-5-oxo-7,8-dihydropyrimido[5,4-f][1,4]-oxazepin-6-(5H)-yl)phenyl]cyclohexyl}acetate was prepared as follows.

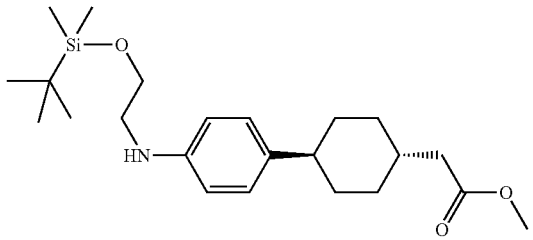

Step 1. Methyl(trans-4-{4-[(2-{[tert-butyl(dimethyl)silyl]oxy}ethyl)amino]-phenyl}cyclohexyl)acetate, shown above, was prepared as follows.

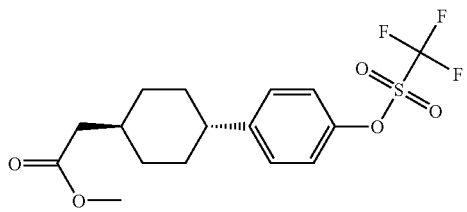

Methyl[trans-4-[4-[[(trifluoromethyl)sulfonyl]oxy]phenyl]cyclohexyl]acetate, shown above, which is identified as Compound 55 in U.S. Pat. No. 7,244,727, issued Jul. 17, 2007, was prepared according to the method described therein. A mixture of methyl[trans-4-[4-[[(trifluoromethyl)sulfonyl]oxy]phenyl]cyclohexyl]acetate (10.1 g, 26.6 mmol), 2-{[tert-butyl (dimethyl)silyl]oxy}ethanamine (5.59 g, 31.9 mmol), which can be prepared by various methods including those disclosed in Journal of the American Chemical Society, 129(37), 11408-11420; 2007, Organic Letters, 9(1), 101-104; 2007 or Bioorganic & Medicinal Chemistry, 13(11), 3821-3839; 2005, cesium carbonate (8.65 g, 26.6 mmol), palladium acetate (0.60 g, 2.66 mmol) and X-PHOS (1.27 g, 2.66 mmol) in toluene (53 mL) under nitrogen was heated in a sealed tube at 120° C. for 16 hours. The reaction was cooled, diluted into EtOAc, washed with water (2×), saturated aqueous brine, dried over sodium sulfate and concentrated to afford a dark oil. Chromatography (330 g Biotage Snap Cartridge® silica gel column, 0-15% EtOAc:heptane) afforded methyl(trans-4-{4-[(2-{[tert-butyl(dimethyl)silyl]oxy}ethyl)-amino]phenyl}cyclohexyl)acetate as a light-yellow oil, 6.70 g. $^1$H NMR (400 MHz, CDCl$_3$): δ 7.02, (d, 2H), 6.61 (d, 2H), 3.80 (m, 2H), 3.64 (s, 3H), 3.20 (m, 2H), 2.37 (m, 1H), 2.24 (m, 2H), 1.85 (m, 5H), 1.44 (m, 2H), 1.13 (m, 2H), 0.87 (s, 9H), 0.04 (s, 6H). m/z=406.4 (M+1).

Step 2. Methyl[trans-4-(4-{(2-{[tert-butyl(dimethyl)silyl]oxy}ethyl)[(4,6-dichloropyrimidine-5-yl)carbonyl]amino}phenyl)cyclohexyl]acetate, shown below, was prepared as follows.

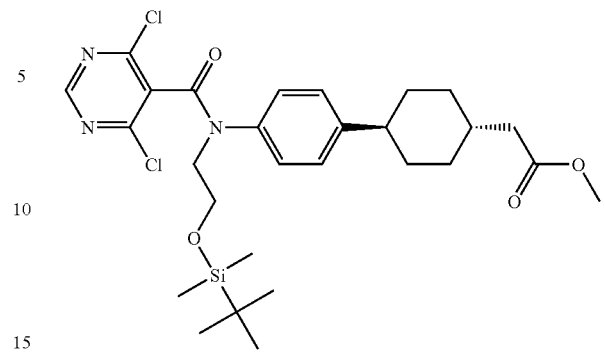

To a stirred, cooled (0° C.) solution of methyl(trans-4-{4-[(2-{[tert-butyl-(dimethyl)silyl]oxy}ethyl)amino]phenyl}cyclohexyl)acetate (9.7 g, 24.0 mmol), from Step 1, and TEA (3.53 mL, 25.3 mmol) in THF (60 mL) was added dropwise a solution of 4,6-dichloropyrimidine-5-carbonyl chloride (5.31 g, 25.1 mmol) in THF (20 mL). After 2 hours, the reaction was concentrated in vacuo, diluted into EtOAc, washed with water (3×), saturated aqueous brine, dried over sodium sulfate and concentrated in vacuo, to afford an oil, which was carried on to the next step without further purification. $^1$H NMR (400 MHz, CDCl$_3$): δ 8.57 (s, 1H), 7.35 (d, 2H), 7.03 (d, 2H), 4.00 (m, 2H), 3.87 (m, 2H), 3.63 (s, 3H), 2.37 (m, 1H), 2.22 (m, 2H), 1.82 (m, 5H), 1.36 (m, 2H), 1.11 (m, 2H), 0.83 (s, 9H), 0.02 (s, 6H). m/z=580.3 (M+1).

Step 3. Methyl(trans-4-{4-[[(4,6-dichloropyrimidin-5-yl)carbonyl](2-hydroxyethyl)amino]phenyl}cyclohexyl)acetate, shown below, was prepared as follows.

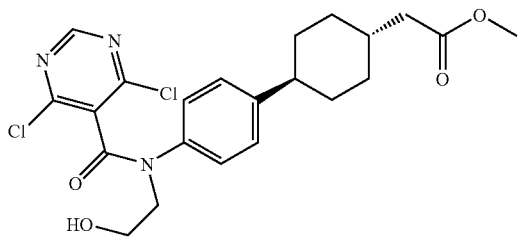

A solution of methyl[trans-4-(4-{(2-{[tert-butyl(dimethyl)silyl]oxy}ethyl)[(4,6-dichloropyrimidin-5-yl)carbonyl]amino}phenyl)cyclohexyl]acetate (14.0 g, 24.0 mmol), from Step 2, in a methanolic solution of HCl (3 mL of concentrated aqueous HCl in 97 mL of methanol) was stirred at room temperature for 30 minutes. Methanol was removed in vacuo, the residue was dissolved in EtOAc, washed with saturated aqueous sodium bicarbonate, saturated aqueous brine, dried over sodium sulfate and concentrated in vacuo to afford an oil, which was carried on to the next step without further purification. $^1$H NMR (400 MHz, CDCl$_3$): δ 8.59 (s, 1H), 7.32 (d, 2H), 7.04 (d, 2H), 4.08 (m, 2H), 3.92 (m, 2H), 3.63 (s, 3H), 2.38 (m, 1H), 2.23 (m, 2H), 1.82 (m, 5H), 1.39 (m, 2H), 1.11 (m, 2H). m/z=466.2 (M+1).

Step 4. The title compound of Preparation 1 was prepared as follows. A slurry of methyl(trans-4-{-[[(4,6-dichloropyrimidin-5-yl)carbonyl](2-hydroxy-ethyl)amino]phenyl}cyclohexyl)acetate (4.78 g, 10.2 mmol, unpurified material from Step 3) and TEA (4.15 g, 41 mmol) in acetonitrile was stirred at 80° C. for 6 hours. The reaction was cooled, concentrated in vacuo, diluted into EtOAc, washed with water (3×), saturated aqueous brine, dried over sodium sulfate and concentrated in vacuo to afford a yellow solid. This material was slurried in methanol (10 mL), filtered, the solids washed with methanol (2×3 mL) and dried in vacuo to afford the title compound as a yellow solid, 4.03 g. ¹H NMR (400 MHz, CDCl₃): δ 8.75 (s, 1H), 7.22 (s, 4H), 4.75 (m, 2H), 4.03 (m, 2H), 3.63 (s, 3H), 2.50 (m, 1H), 2.23 (m, 2H), 1.87 (m, 5H), 1.44 (m, 2H), 1.19 (m, 2H). m/z=430.3 (M+1).

Preparation 2

Methyl 2-((1S,4s)-4-(4-((R)-4-chloro-8-methyl-5-oxo-7,8-dihydropyrimido-[5,4-f][1,4]oxazepin-6 (5H)-yl)phenyl)cyclohexyl)acetate

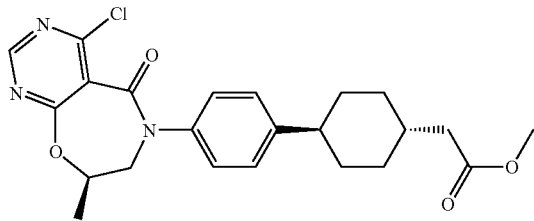

Methyl(trans)-4-(4-((R)-4-chloro-8-methyl-5-oxo-7,8-dihydro-pyrimido[5,4-f][1,4]oxazepin-6(5H)-yl)phenyl]cyclohexyl}acetate was prepared as follows.

Step 1. Methyl[trans-4-(4-{[(2R)-2-{[tert-butyl(dimethyl) silyl]oxy}propyl]-amino}phenyl)cyclohexyl]acetate, shown below, was prepared as follows.

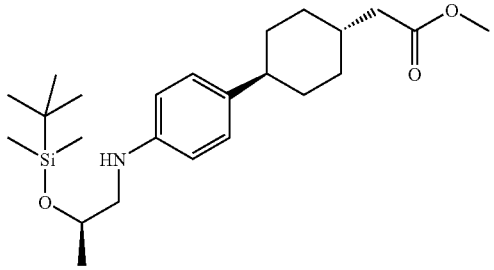

A mixture of methyl[trans-4-[4-[[(trifluoromethyl)sulfonyl]oxy]phenyl]-cyclohexyl]acetate (5.00 g, 13.1 mmol), shown below,

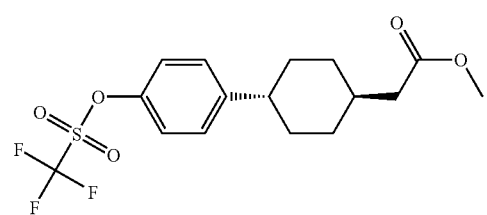

(R)-2-(tert-butyldimethylsilyloxy)propan-1-amine (2.99 g, 15.8 mmol), shown below,

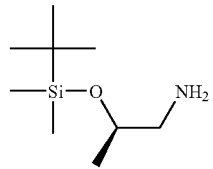

which can be prepared by various methods including those disclosed in the Journal of Organic Chemistry, 72(20), 7726-7735; 2007, cesium carbonate (5.14 g, 15.8 mmol), palladium acetate (310 mg, 1.32 mmol) and X-PHOS (627 mg, 1.32 mmol) in toluene (100 mL) under nitrogen was heated in a sealed tube at 120° C. for 16 hours. The reaction was cooled, diluted into EtOAc (500 mL), washed with water (2×200 mL), saturated aqueous brine, dried over sodium sulfate and concentrated to afford a dark oil. Chromatography (120 g silica gel column, 3-15% EtOAc:heptane) afforded the methyl[trans-4-(4-{[(2R)-2-{[tert-butyl(dimethyl)silyl] oxy}propyl]amino}phenyl)cyclohexyl]acetate as a light-yellow oil, 4.55 g (86%). m/z=420.1 (M+1).

Step 2. Methyl[trans-4-(4-{[(2R)-2-{[tert-butyl(dimethyl) silyl]oxy}propyl]-[(4,6-dichloropyrimidin-5-yl)carbonyl] amino}phenyl)cyclohexyl]acetate, shown below, was prepared as follows.

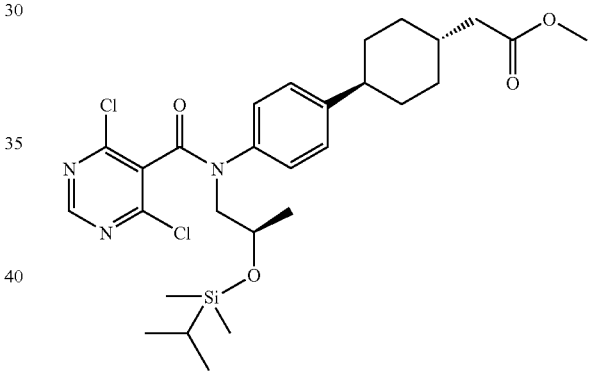

A mixture of 4,6-dichloropyrimidine-5-carbonyl chloride (2.27 g, 10.7 mmol), methyl[trans-4-(4-{[(2R)-2-{[tert-butyl (dimethyl)silyl]oxy}propyl]-amino}phenyl)cyclohexyl]acetate (4.50 g, 10.7 mmol), from Step 1, and TEA (2.24 mL, 16.1 mmol) in THF (150 mL) was stirred at room temperature under nitrogen for 14 hours. The reaction mixture was concentrated to remove THF. The residue was diluted with EtOAc (300 mL), washed with water (2×200 mL), dried over MgSO₄ and concentrated. The crude material was purified by a 120 g silica gel column eluted with 3-15% EtOAc in heptane to give methyl[trans-4-(4-{[(2R)-2-{[tert-butyl(dimethyl)silyl]oxy}propyl][(4,6-dichloropyrimidin-5-yl)carbonyl] amino}phenyl)cyclohexyl]acetate as a colorless oil 4.01 g (63%). m/z=594.2 (M+1). 1H NMR (400 MHz, chloroform-d) δ −0.06 (s, 6H) 0.71 (s, 9H) 0.99-1.14 (m, 2H) 1.25-1.30 (m, 3H) 1.30-1.42 (m, 2H) 1.78 (dd, J=28.30, 11.90 Hz, 5H) 2.20 (d, J=7.03 Hz, 2H) 2.28-2.39 (m, 1H) 3.64 (s, 3H) 3.83-3.97 (m, 2H) 4.04-4.14 (m, 1H) 7.00 (d, J=8.20 Hz, 2H) 7.19 (d, J=8.59 Hz, 2H) 8.53 (s, 1H).

Step 3. The title compound of Preparation 2 was prepared as follows. 4M HCl in dioxane (25 mL) was added to a solution of methyl[trans-4-(4-{[(2R)-2-{[tert-butyl(dimethyl)silyl]oxy}propyl][(4,6-dichloropyrimidin-5-yl)carbonyl]amino}phenyl)cyclohexyl]acetate (3.95 g, 6.72 mmol), from Step 2, in methanol (50 mL). The mixture was stirred at 23° C. for 30 minutes. The reaction mixture was concentrated to remove the solvent. The residue was dissolved in acetonitrile (200 mL), then K$_2$CO$_3$ (1.86 g, 13.5 mmol) and 5 Angstrom molecular sieves (1.0 g) were added to it. The reaction mixture was stirred at 80° C. for 30 hours. EtOAc (250 mL) and water (250 mL) were added to reaction mixture. The organic layer was separated and dried over MgSO$_4$ and concentrated. The crude material was purified by a 120 g silica gel column eluted with 30-50% EtOAc in heptane to give a colorless oil 1.85 g (61%) as the title compound. m/z=444.1 (M+1). 1H NMR (400 MHz, chloroform-d) δ 1.09-1.23 (m, 2H) 1.43 (d, J=6.64 Hz, 3H) 1.44-1.57 (m, 2H) 1.80-1.96 (m, 5H) 2.26 (d, J=7.05 Hz, 2H) 2.44-2.55 (m, 1H) 3.68 (s, 3H) 3.80-3.95 (m, 2H) 5.00-5.12 (m, 1H) 7.29 (s, 4H) 8.76 (s, 1H).

Preparation 3

Methyl(trans-4-{4-[(7S)-4-chloro-7-methyl-5-oxo-7,8-dihydropyrimido[5,4-f][1,4]oxazepin-6(5H)-yl]phenyl}cyclohexyl)acetate

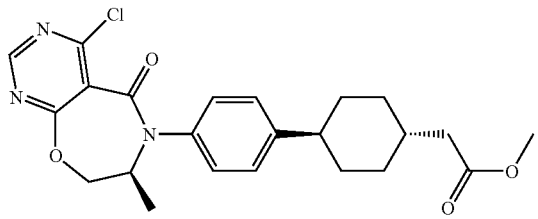

The compound methyl(trans-4-{4-[(7S)-4-chloro-7-methyl-5-oxo-7,8-dihydropyrimido[5,4-f][1,4]oxazepin-6 (5H)-yl]phenyl}cyclohexyl)acetate was prepared as follows.

Step 1. (S)-1-(Tert-butyldimethylsilyloxy)propan-2-amine, shown below, was prepared as follows.

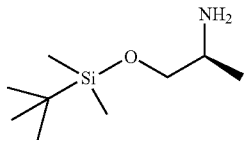

Tert-butyldimethylsilyl chloride (22.1 g, 146 mmol) was added to a stirred solution of the (S)-2-aminopropan-1-ol (10 g, 130 mmol) and TEA (23.9 ml, 172 mmol) in 325 ml of dichloromethane. The heterogeneous mixture was stirred at room temperature for 18 hours. The reaction was diluted into EtOAc and the organic layer was washed with brine then dried over sodium sulfate and concentrated in vacuo to recover 20.37 g of product. 1H NMR (400 MHz, chloroform-d) δ 0.05 (s, 6H) 0.89 (s, 9H) 1.01 (d, J=6.64 Hz, 3H) 2.87-3.07 (m, 1H) 3.18-3.35 (m, 1H) 3.51 (dd, J=9.75, 4.35 Hz, 1H) m/z=190.2 (M+1).

Step 2. 2-((1S,4r)-4-(4-((S)-1-(tert-butyldimethylsilyloxy) propan-2-ylamino)phenyl)cyclohexyl)acetic acid, shown below, was prepared as follows

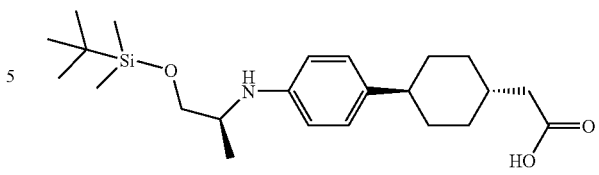

A mixture of methyl[trans-4-(4-{[(trifluoromethyl)sulfonyl]oxy}-phenyl)cyclohexyl]acetate (1 g, 3 mmol), (S)-1-(tert-butyldimethylsilyloxy)-propan-2-amine (0.597 g, 3.16 mmol), palladium(II) acetate (0.061 g, 0.271 mmol), X-PHOS (0.125 g, 0.263 mmol), cesium carbonate (1.03 g, 3.16 mmol) were diluted in 26.3 ml of toluene. The mixture was purged with nitrogen flow for a few minutes and then capped tightly. The reaction was then heated to 120° C. with stirring for 16 hours. The reaction was subsequently cooled, and diluted with EtOAc. The organic mixture was washed with water and brine, dried over MgSO$_4$ and concentrated. The product was columned on silica from 5-20% EtOAc in heptane to recover 0.82 g of methyl trans 2S-(4-(4-(1-(tert-butyldimethylsilyloxy)propan-2-ylamino)phenyl)cyclohexyl)acetate. 1H NMR (400 MHz, chloroform-d) δ 0.03 (d, J=4.98 Hz, 6H) 0.89 (s, 9H) 1.05-1.19 (m, 2H) 1.18 (d, J=6.22 Hz, 3H) 1.44 (q, J=12.44 Hz, 2H) 1.76-1.93 (m, 5H) 2.23 (d, J=7.05 Hz, 2H) 2.34 (t, J=12.03 Hz, 1H) 3.42-3.65 (m, 3H) 3.67 (s, 3H) 6.55 (d, J=8.29 Hz, 2H) 6.99 (d, J=8.29 Hz, 2H). m/z=420.3 (M+1)

Step 3. Methyl[trans-4-(4-{[(3S)-2-{[tert-butyl(dimethyl)silyl]oxy}propyl]-[(4,6-dichloropyrimidin-5-yl)carbonyl]amino}phenyl)cyclohexyl]acetate, shown below, was prepared as follows:

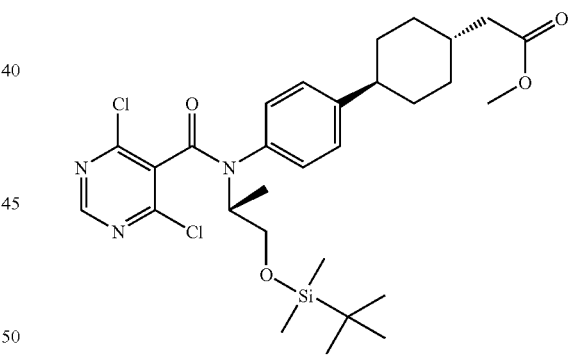

4,6-Dichloropyrimidine-5-carbonyl chloride (0.454 g, 2.15 mmol) was added to a solution of methyl trans 2S-(4-(4-(1-(tert-butyldimethylsilyloxy)propan-2-ylamino)phenyl) cyclohexyl)acetate (0.82 g, 2.0 mmol), from Step 2, and diisopropylethylamine (0.418 ml, 2.4 mmol) in 4.16 ml of MTHF at 0° C. and stirred cold for 1.5 hours. Added water and EtOAc; separated layers. Washed organic layer with Saturated sodium bicarbonate, brine then dried and concentrated. Columned product on silica from 10-30% EtOAc in heptane to recover 0.95 g of product. 1H NMR (400 MHz, chloroform-d) δ 0.06 (d, J=4.98 Hz, 6H) 0.90 (s, 9H) 0.99-1.18 (m, 2H) 1.17 (d, J=6.64 Hz, 3H) 1.28-1.45 (m, 2H) 1.73-1.94 (m, 5H) 2.23 (d, J=6.64 Hz, 2H) 2.38 (t, J=11.61 Hz, 1H) 3.51-3.66 (m, 2H) 3.67 (s, 3H) 4.84-5.03 (m, 1H) 7.03 (d, J=8.71 Hz, 2H) 7.34 (br. s., 2H) 8.50 (s, 1H). m/z=597.2 (M+4)

Step 4. Methyl[trans-4-(4-{[(3S)-2-{oxy}propyl][(4,6-dichloropyrimidin-5-yl)carbonyl]amino}phenyl)cyclohexyl]acetate, shown below, was prepared as follows.

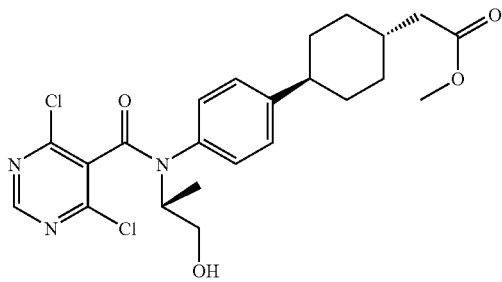

Methyl[trans-4-(4-{[(3S)-2-{[tert-butyl(dimethyl)silyl]oxy}propyl][(4,6-dichloropyrimidin-5-yl)carbonyl]amino}phenyl)cyclohexyl]acetate (0.95 g, 1.6 mmol), from Step 3, and 7.4 ml of 1% HCl-methanol (3 mL of 36% aqueous HCl and 97 mL of methanol) were stirred at room temperature and monitored by LC-MS. The reaction mixture was concentrated to remove methanol. The crude material was dissolved into EtOAc (200 ml). The EtOAc solution was washed with NaHCO₃ aqueous solution (2×100 ml), water (100 ml) and brine (100 mL), dried over MgSO₄ and concentrated to recover 0.77 g of product. 1H NMR (400 MHz, chloroform-d) δ 1.03-1.17 (m, 2H) 1.19 (d, J=7.05 Hz, 3H) 1.29-1.46 (m, 2H) 1.69-1.91 (m, 5H) 2.23 (d, J=7.05 Hz, 2H) 2.38 (t, J=12.23 Hz, 1H) 3.60 (dd, J=11.61, 9.12 Hz, 1H) 3.67 (s, 3H) 3.78 (dd, J=11.82, 4.35 Hz, 1H) 4.85-5.04 (m, 1H) 7.07 (d, J=8.71 Hz, 2H) 7.33 (br. s., 2H) 8.52 (s, 1H) m/z=483.1 (M+4).

Step 5. The title compound of Preparation 3 was prepared as follows. Methyl[trans-4-(4-{[(3S)-2-{oxy}propyl][(4,6-dichloropyrimidin-5-yl)carbonyl]-amino}phenyl)cyclohexyl]acetate (0.8 g, 1.66 mmol), potassium carbonate (0.46 g, 3.33 mmol) and 200 mg of molecular sieves were mixed into 41.6 ml of acetonitrile. The mixture was added to sealed tube and heated at 80° C. overnight. The reaction mixture was concentrated and then diluted with EtOAc and water. Separated layers and washed organic layer with brine, then dried and concentrated. Columned product on silica in 40% ethyl acetate in heptane to recover 0.22 g. 1H NMR (400 MHz, chloroform-d) δ 1.06 (d, J=7.05 Hz, 3H) 1.10-1.25 (m, 2H) 1.42-1.55 (m, 2H) 1.73-1.98 (m, 5H) 2.26 (d, J=6.64 Hz, 2H) 2.41-2.59 (m, 1H) 3.69 (s, 3H) 4.27-4.42 (m, 1H) 4.45-4.70 (m, 2H) 7.17 (d, J=8.29 Hz, 2H) 7.30 (d, J=8.71 Hz, 2H) 8.76 (s, 1H) m/z=444.0 (M+1).

Preparation 4

Methyl 2-(4-(4-(4-chloro-5-oxo-7,8-dihydropyrimido[5,4-f][1,4]oxazepin-6(5H)-yl)-3-fluorophenyl)cyclohexyl)acetate

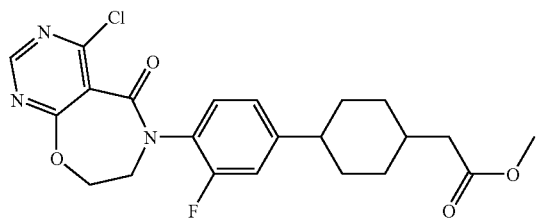

Methyl 2-(4-(4-(4-chloro-5-oxo-7,8-dihydropyrimido[5,4-f][1,4]oxazepin-6(5H)-yl)-3-fluorophenyl)cyclohexyl)acetate, shown above, was prepared as follows.

Step 1. 1-(Bromomethyl)benzene (4.92 g, 28.8 mmol) and K₂CO₃ (3.98 g, 28.8 mmol) were added to a solution of 4-bromo-2-fluorophenol (5.0 g, 26 mmol) in acetone. The reaction mixture was stirred at room temperature for 18 hours. Water (100 mL) and EtOAc (100 mL) were added, the organic layer was separated and dried over MgSO₄ and concentrated to give 1-(benzyloxy)-4-bromo-2-fluorobenzene as a yellow solid 7.06 g.

¹H NMR (400 MHz, CDCl₃): δ 7.24-7.41 (m, 5H), 7.20 (m, 1H), 7.16 (m, 1H), 6.82 (m, 1H), 5.10 (m, 2H).

Step 2. Methyl 2-(4-(4-(benzyloxy)-3-fluorophenyl)cyclohex-3-enyl)acetate, shown below, was prepared as follows.

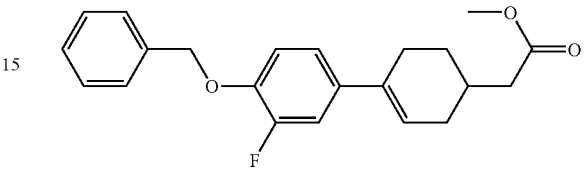

Pd(PPh₃)₄ (16.2 mg, 0.014 mmol) and CsCO₃ (142 mg, 0.428 mmol) were added to a solution of 1-(benzyloxy)-4-bromo-2-fluorobenzene (130 mg, 0.464 mmol) and methyl 2-(4-(4,4,5,5-tetramethyl-1,3,2-dioxaborolan-2-yl)cyclohex-3-enyl)acetate (100 mg, 0.357 mmol), shown below, and prepared as described in Preparation 4A,

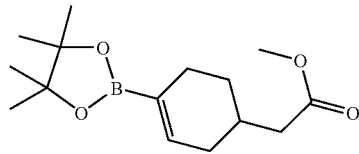

in THF (2 mL) under nitrogen.

The reaction mixture was refluxed with stirring for 24 hours. LC-MS showed desired product. The reaction mixture was cooled, diluted with EtOAc (30 mL), washed with water and brine, dried over MgSO₄ and concentrated. The crude material was purified by chromatography (12 g silica gel column eluted with 5-10% EtOAc:heptane) to give methyl 2-(4-(4-(benzyloxy)-3-fluorophenyl)cyclohex-3-enyl)acetate as a white solid (110 mg). ¹H NMR (400 MHz, CDCl₃): δ 7.28-7.42 (m, 5H), 7.10 (dd, 1H), 7.0 (d, 1H), 6.88 (t, 1H), 6.0 (m, 1H), 5.1 (s, 2H), 3.66 (s, 3H), 2.38 (m, 2H), 2.3 (d, 2H), 2.2 (m, 1H), 2.1 (m, 1H), 1.9 (m, 2H), 1.4 (m, 1H). m/z=355.4 (M+1).

Step 3. Methyl 2-(4-(3-fluoro-4-hydroxyphenyl)cyclohexyl)acetate, shown below, was prepared as follows.

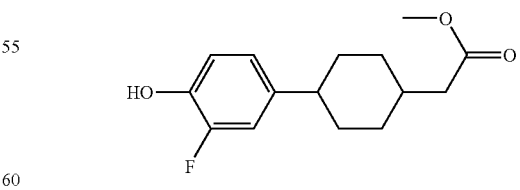

Methyl 2-(4-(4-(benzyloxy)-3-fluorophenyl)cyclohex-3-enyl)acetate (520 mg, 1.47 mmol) was dissolved in ethanol (15 mL) and EtOAc (15 mL). 20% Pd(OH)₂/C (150 mg) was added to it. The reaction mixture was shaken under 50 psi hydrogen for 20 hours. The mixture was filtrated through diatomaceous earth (Celite®) to remove catalyst and then concentrated. The purification was done by chromatography (12 g RediSep® silica gel column (Teledyne ISCO, Lincoln, Nebr.) with 5-10% EtOAc:heptane) to give methyl 2-(4-(4-(benzyloxy)-3-fluorophenyl)cyclohex-3-enyl)acetate as a colorless oil (320 mg). $^1$H NMR (400 MHz, CDCl$_3$): δ 6.80-7.0 (m, 3H), 5.58 (d, 1H), 3.63 (s, 3H), 2.24-2.5 (m, 1H), 2.4, 2.2 (d, 2H), 1.8 (m, 3H), 1.6 (m, 4H), 1.4 (m, 1H), 1, 12 (m, 1H). m/z=265.3 (M−1).

Step 4. Methyl 2-(4-(3-fluoro-4-(trifluoromethylsulfonyloxy)phenyl)cyclohexyl)acetate, shown below, was prepared as follows.

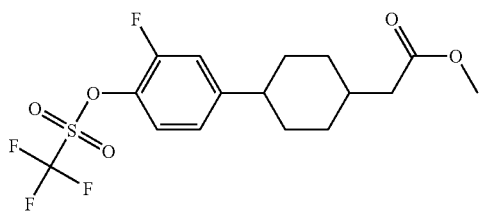

To a stirred solution of phenol (310 mg, 1.16 mmol) and TEA (0.24 mL, 1.75 mmol) in CH$_2$Cl$_2$ (5 mL) was added a triflic anhydride solution (413 mg, 1.46 mmol) dropwise. The mixture was stirred at 0° C. for 2 hours. The reaction mixture was washed with water (×2) and brine (×1), dried over Na$_2$SO$_4$ and filtered. The organic solution was concentrated and purified by chromatography (12 g silica gel column with 3-15% EtOAc:heptane) to give methyl 2-(4-(3-fluoro-4-(trifluoromethylsulfonyloxy)phenyl)cyclohexyl)acetate as a colorless oil (380 mg). m/z=397.4 (M−1).

Step 5. Methyl 2-(4-(4-(2-(tert-butyldimethylsilyloxy) ethylamino)-3-fluorophenyl)cyclohexyl)acetate, shown below, was prepared as follows.

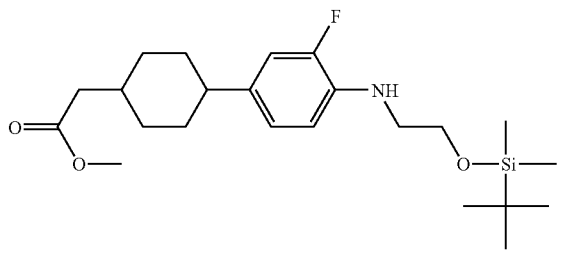

A mixture of methyl 2-(4-(3-fluoro-4-(trifluoromethylsulfonyloxy)phenyl)cyclohexyl)acetate (190 mg, 0.477 mmol), 2-{[tert-butyl(dimethyl)silyl]oxy}ethanamine (100 mg, 0.572 mmol), cesium carbonate (171 mg, 0.525 mmol), palladium acetate (11 mg, 0.048 mmol) and (X-PHOS) (23 mg, 0.048 mmol) in toluene (5 mL), under nitrogen, was heated in a sealed tube at 120° C. for 16 hours. The reaction was cooled, diluted into EtOAc, washed with water (2×), saturated aqueous brine, dried over sodium sulfate and concentrated to afford a dark oil. Chromatography (12 g silica gel column, 3-15% EtOAc:heptane) afforded methyl 2-(4-(4-(2-(tert-butyldimethyl-silyloxy)ethylamino)-3-fluorophenyl)-cyclohexyl)acetate as a light-yellow oil, 110 mg. 1H NMR (400 MHz, CDCl$_3$); δ 7.2 (m, 1H), 6.95 (m, 1H), 6.8 (m, 1H), 3.8 (m, 2H), 3.64 (s, 3H), 3.2 (m, 2H), 2.5, 2.3 (m, 1H), 2.4, 2.2 (d, 2H), 1.85 (m, 2H), 1.64 (m, 5H), 1.4 (m, 1H), 1.1 (m, 1H), 0.88 (s, 9H), 0.06 (s, 6H). m/z=424.2 (M+1).

Step 6. Methyl 2-(4-(4-(N-(2-(tert-butyldimethylsilyloxy) ethyl)-4,6-dichloropyrimidine-5-carboxamido)-3-fluorophenyl)cyclohexyl)acetate, shown below, was prepared as follows.

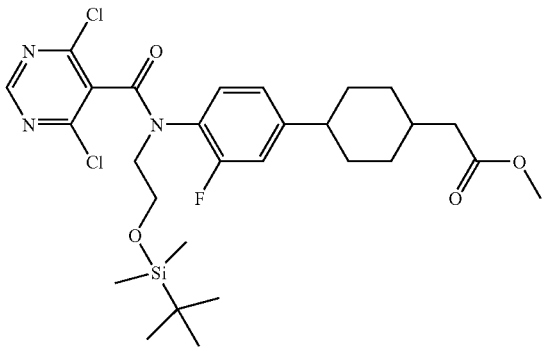

A mixture of 4,6-dichloropyrimidine-5-carbonyl chloride (82.5 mg, 0.390), methyl 2-(4-(4-(2-(tert-butyldimethylsilyloxy)ethylamino)-3-fluorophenyl)cyclohexyl)acetate (110 mg, 0.26 mmol) and TEA (0.054 mL, 0.39 mmol) in THF (2 mL) was stirred at room temperature under nitrogen for 14 hours. The reaction mixture was concentrated to remove THF. The residue was diluted with EtOAc, washed with water, dried over MgSO$_4$ and concentrated. The crude material was purified by a 12 g silica gel column eluted with 3-15% EtOAc in heptane to give methyl 2-(4-(4-(N-(2-(tert-butyldimethylsilyloxy) ethyl)-4,6-dichloropyrimidine-5-carboxamido)-3-fluorophenyl)cyclohexyl)acetate a colorless oil (60 mg). m/z=598.2 (M+1).

Step 7. The title compound of Preparation 4 was prepared as follows. 4M HCl in dioxane (0.5 mL) was added to a solution of methyl 2-(4-(4-(N-(2-(tert-butyldimethylsilyloxy)ethyl)-4,6-dichloropyrimidine-5-carboxamido)-3-fluorophenyl)cyclohexyl)acetate (30 mg, 0.05 mmol) in methanol (1 mL). The mixture was stirred at 23° C. for 30 minutes. The reaction mixture was concentrated to remove solvent. The residue was dissolved in acetonitrile (1 mL) and NEt$_3$ (0.05 mL) was added to it. The reaction mixture was stirred at 80° C. for 18 hours. EtOAc (15 mL) and water (15 mL) were added to reaction mixture. The organic layer was separated and dried over MgSO$_4$ and concentrated. The crude material was purified by a 4 g silica gel column eluted with 30-50% EtOAc in heptane to give methyl 2-(4-(4-(4-chloro-5-oxo-7, 8-dihydropyrimido[5,4-f][1,4]oxazepin-6(5H)-yl)-3-fluorophenyl)cyclohexyl)acetate a colorless oil (20 mg). m/z=448.4 (M+1).

Preparation 4A

Methyl 2-(4-(4,4,5,5-tetramethyl-1,3,2-dioxaborolan-2-yl)cyclohex-3-enyl)acetate

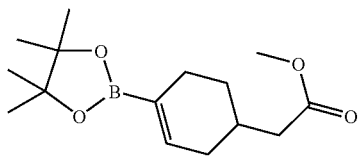

Methyl 2-(4-(4,4,5,5-tetramethyl-1,3,2-dioxaborolan-2-yl)cyclohex-3-enyl)acetate was prepared as follows.

NaH (9.2 g, 384 mmol, 1.5 eq) was suspended in THF (850 ml). This was cooled to ° C. and trimethylphosphonoacetate (40 ml, 277 mmol, 1.1 eq) was added dropwise keeping T<10° C. Mixture was then recooled to 0° C. and stirred for 15 min. Then compound 1 (40 g, 256 mmol, 1.0 eq) in THF (300 ml) was added dropwise. The reaction mixture was stirred over night allowing it to warm to room temperature. The mixture was poured into water (500 ml) and EtOAc (300 ml) were added, the layers were separated. The aqueous layer was extracted with EtOAc (400 ml). The combined organic layers were dried ($Na_2SO_4$) and evaporated. Yield: 51.6 g of methyl 2-(4-(1,3-dioxalane)cyclohexylidene)acetate; $^1$H NMR ($CDCl_3$, 300 MHz) δ 1.78 (q, 4H), 2.37 (t, 2H), 2.99 (t, 2H), 3.68 (s, 3H), 3.99 (s, 4H), 5.65 (s, 1H)

Methyl 2-(4-(1,3-dioxalane)cyclohexylidene)acetate (51.6 g) and 10% Pd/C (50% wet, (5 table-spoons)) was added to EtOAc (1 L). The reaction mixture was degassed and a $H_2$-balloon was mounted. This was stirred over night at room temperature. The reaction mixture was filtered over celite and rinsed with EtOAc. The filtrate was evaporated. Yield: 51.1 g of methyl 2-(4-(1,3-dioxalane)cyclohexyl)acetate. $^1$H NMR ($CDCl_3$, 300 MHz) δ 1.35 (m, 2H), 1.57 (m, 2H), 1.76 (m, 4H), 1.82 (m, 1H), 2.22 (d, 2H), 3.65 (s, 3H), 3.95 (s, 4H)

Methyl 2-(4-(1,3-dioxalane)cyclohexyl)acetate (51.1 g, 238 mmol, 1.0 eq) was dissolved in THF (2 L). This was cooled to 0° C. and 2 N HCl (1.4 L, 2.8 mol, 12.0 eq) was added dropwise in 2.5 hours keeping T=0° C. The reaction mixture was stirred over night allowing it to warm to room temperature. Then water (1 L) and EtOAc (1 L) were added and the layers were separated. The aqueous layer was extracted with EtOAc (1 L). The combined organic layers were washed with brine (1 L) and dried ($Na_2SO_4$). The mixture was evaporated and purified by column chromatography (silica: EtOAc/heptane=¼). Yield: 21.9 g, 54% (clear oil) of methyl 2-(4-oxocyclohexyl)acetate. $^1$H NMR ($CDCl_3$, 300 MHz) δ 1.50 (m, 2H), 2.16 (m, 2H), 2.36 (d, 2H), 2.38 (m, 1H), 2.39 (m, 4H), 3.71 (s, 3H)

Methyl 2-(4-oxocyclohexyl)acetate (8.13 g, 47.9 mmol, 1.0 eq) and 2,-di-tert.butyl-4-methylpyridine (11.3 g, 55 mmol, 1.15 eq) were dissolved in dry DCM (300 ml). To the reaction mixture $Tf_2O$ (8.35 ml, 50 mmol, 1.05 eq) was added dropwise and stirred for 2 h. The reaction mixture turned from orange to green while adding $Tf_2O$ and after 30 min a suspension was formed. The suspension was filtered and the filtrate was evaporated. Crude mixture was dissolved in DCM (200 ml) and filtered. The filtrate was evaporated. Yield: 14.3 g, 99% (green semi-solid) of methyl 2-(4-(trifluoromethyl-sulfonyloxy)cyclohex-3-enyl)acetate. $^1$H NMR ($CDCl_3$, 300 MHz) δ 1.92 (m, 2H), 2.18 (m, 2H), 2.31 (d, 2H), 2.36 (m, 2H), 2.42 (m, 1H), 3.65 (s, 3H), 5.74 (t, 1H)

Methyl 2-(4-(trifluoromethyl-sulfonyloxy)cyclohex-3-enyl)acetate (21.9 g, 72.4 mmol, 1.0 eq), bis(pinacolato)diboron (16.7 g, 65.8 mmol, 0.9 eq), KOAc (21.5 g, 219 mmol, 3.0 eq) and $PdCl_2$(dppf) (1.6 g, 2.19 mmol, 0.03 eq) were dissolved in DMSO (550 ml). The reaction mixture was bubbled through with $N_2$-gas for 15 min and then heated to 50° C. and stirred for 2.5 h. To the reaction mixture water (400 ml) and EtOAc (600 ml) were added and the layers were separated. The aqueous layer was extracted with EtOAc (600 ml). The combined organic layers were washed with brine (500 ml) and dried ($Na_2SO_4$). The mixture was evaporated and purified by column chromatography (silica: EtOAc/heptane=5/95). Yield: 9.15 g, 45% (brown-yellow oil) of methyl 2-(4-(4,4,5,5-tetramethyl-1,3,2-dioxaborolan-2-yl)cyclohex-3-enyl)acetate. $^1$H NMR ($CDCl_3$, 300 MHz) δ 1.25 (s, 12H), 1.77 (m, 2H), 1.83 (m, 1H), 2.07 (m, 1H), 2.14 (m, 1H), 2.20 (m, 2H), 2.56 (d, 2H), 3.67 (s, 3H), 6.50 (t, 1H).

Example 1

Methyl {trans-4-[4-(4-amino-5-oxo-7,8-dihydropyrimido[5,4-f][1,4]oxazepin-6-(5H)-yl)phenyl]cyclohexyl}Acetate

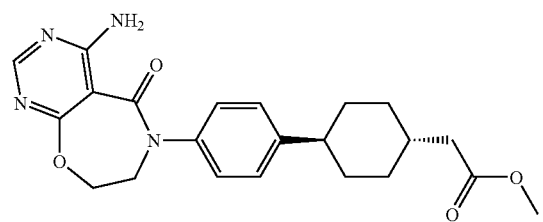

The compound methyl {trans-4-[4-(4-amino-5-oxo-7,8-dihydropyrimido[5,4-f][1,4]oxazepin-6-(5H)-yl)phenyl]cyclohexyl}acetate, shown above, was prepared as follows.

A solution of methyl {trans-4-[4-(4-chloro-5-oxo-7,8-dihydropyrimido[5,4-f][1,4]oxazepin-6-(5H)-yl)phenyl]cyclohexyl}acetate, from Preparation 1, (5.29 g, 12.3 mmol) in 0.5M ammonia in p-dioxane (120 mL) was stirred at room temperature for 24 hours. The reaction mixture was concentrated in vacuo, diluted into EtOAc (1 L), washed with water, saturated aqueous brine, dried over sodium sulfate and concentrated in vacuo to afford the title compound as an off-white solid, 5.04 g. $^1$H NMR (400 MHz, $CDCl_3$): δ 8.22 (s, 1H), 8.16 (br s, 1H), 7.23 (d, 2H), 7.16 (d, 2H), 5.75 (br s, 1H), 4.63 (m, 2H), 3.98 (m, 2H), 3.64 (s, 3H), 2.44 (m, 1H), 2.21 (m, 2H), 1.81 (m, 5H), 1.42 (m, 2H), 1.10 (m, 2H). m/z=411.3 (M+1). $IC_{50}$ 34.5 nM (range 30-40 nM).

Example 2

{Trans-4-[4-(4-amino-5-oxo-7,8-dihydropyrimido[5,4-f][1,4]oxazepin-6(5H)-yl)phenyl]cyclohexyl}Acetic Acid

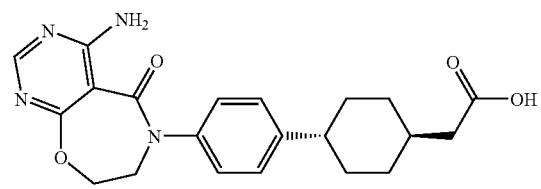

The compound {trans-4-[4-(4-amino-5-oxo-7,8-dihydropyrimido[5,4-f][1,4]oxazepin-6-(5H)-yl)phenyl]cyclohexyl}acetate, shown above, was prepared as follows.

A stirred solution of methyl {trans-4-[4-(4-amino-5-oxo-7,8-dihydropyrimido[5,4-f][1,4]oxazepin-6-(5H)-yl)phenyl]cyclohexyl}acetate (5.05 g, 12.3 mmol), from Example 1, and 1N aqueous lithium hydroxide (36.9 mL) in p-dioxane (96 mL) and water (27 mL) was stirred at 50° C. for one hour. After cooling, the reaction solution was adjusted to pH~3.5 with 6N aqueous hydrochloric acid and the mixture was concentrated to near dryness. This residue was slurried in water (40 mL) for 1 hour, filtered, the solids washed with water (2×20 mL), ether (3×30 mL) and dried in vacuo to afford the title compound as an off-white solid, 4.58 g. $^1$H NMR (400 MHz, DMSO-$d_6$): δ 8.12 (s, 1H), 7.58 (br s, 2H) 7.21 (s, 4H), 4.56 (m, 2H), 3.92 (m, 2H), 2.42 (m, 1H), 2.08 (m, 2H), 1.75 (m, 5H), 1.42 (q, 2H), 1.05 (q, 2H). m/z=397.3 (M+1). IC$_{50}$ 19.1 nM (range 5.2-63.6 nM).

Example 3

(Trans-4-{4-[(8R)-4-amino-8-methyl-5-oxo-7,8-dihydropyrimido[5,4-f][1,4]oxazepin-6(5H)-yl]phenyl}cyclohexyl)acetic Acid

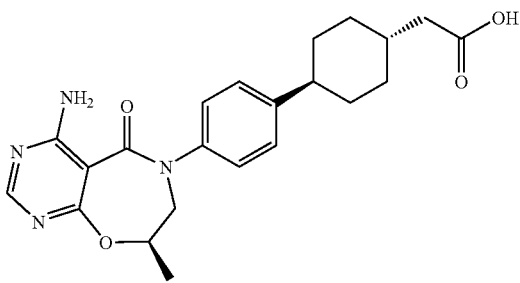

The compound (trans-4-{4-[(8R)-4-amino-8-methyl-5-oxo-7,8-dihydropyrimido[5,4-f][1,4]oxazepin-6(5H)-yl]phenyl}cyclohexyl)acetic acid was prepared as follows.

A mixture of methyl(trans-4-{4-[(8R)-4-chloro-8-methyl-5-oxo-7,8-dihydropyrimido[5,4-f][1,4]oxazepin-6(5H)-yl]phenyl}cyclohexyl)acetate, from Preparation 2, (1.50 g, 3.38 mmol) in 0.5M ammonia in dioxane (20 mL) was stirred at 50° C., in a tightly capped flask, for 6 hours. The reaction mixture was concentrated to give a white solid, which was carried on to the next step without further purification. LiOH (247 mg, 9.89 mmol) was added to a solution of the white solid in THF/MeOH/water (30 mL, 3:2:1) and then the resulting solution was stirred at 23° C. for 18 hours. 1M HCl solution was added to reaction solution to adjust pH to about 3. 20% i-propanol in DCM (130 mL) was added to extract reaction mixture. The organic layer was separated and dried over MgSO$_4$ and concentrated to give a solid. Purification was done by chromatography (80 g, silica gel column) with methanol/DCM from 2-6% to give a white solid 1210 mg (89%) as the title compound. m/z=411.1 (M+1). $^1$H NMR (400 MHz, METHANOL-$d_4$) δ ppm 1.11-1.25 (m, 2H) 1.36 (d, J=6.64 Hz, 3H) 1.53 (q, J=12.88 Hz, 2H) 1.75-1.96 (m, 5H) 2.21 (d, J=7.03 Hz, 2H) 2.46-2.58 (m, 1H) 3.80-3.96 (m, 2H) 4.92-5.03 (m, 1H) 7.25 (d, 2H) 7.31 (d, 2H) 8.17 (s, 1H). IC$_{50}$ 19.3 nM (range 7.0-30.4 nM).

Example 4

Methyl(trans-4-{4-[(7S)-4-amino-7-methyl-5-oxo-7,8-dihydropyrimido[5,4-f][1,4]oxazepin-6(5H)-yl]phenyl}cyclohexyl)acetate

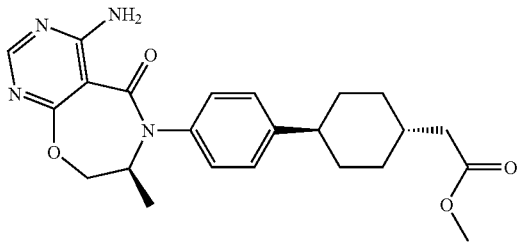

The compound methyl(trans-4-{4-[(7S)-4-amino-7-methyl-5-oxo-7,8-dihydropyrimido[5,4-f][1,4]oxazepin-6(5H)-yl]phenyl}cyclohexyl)acetate was prepared as follows.

Methyl(trans-4-{4-[(7S)-4-chloro-7-methyl-5-oxo-7,8-dihydropyrimido[5,4-f][1,4]oxazepin-6(5H)-yl]phenyl}cyclohexyl)acetate (0.22 g, 0.496 mmol), from Preparation 2, was diluted in 24.8 ml of 0.5M ammonia in dioxane and heated to 50° C., in a tightly capped vial for four hours. After completion, reaction was concentrated to recover 0.26 g of methyl(trans-4-{4-[(7S)-4-amino-7-methyl-5-oxo-7,8-dihydropyrimido[5,4-f][1,4]oxazepin-6(5H)-yl]phenyl}cyclohexyl)acetate. 1H NMR (400 MHz, chloroform-d) δ ppm 1.04-1.26 (m, 2H) 1.33 (d, J=7.05 Hz, 3H) 1.40-1.60 (m, 2H) 1.74-2.04 (m, 5H) 2.26 (d, J=6.64 Hz, 2H) 2.43-2.64 (m, 1H) 3.68 (s, 3H) 3.95-4.16 (m, 1H) 4.46-4.73 (m, 2H) 7.10 (d, J=8.29 Hz, 2H) 7.29 (d, J=8.29 Hz, 2H) 8.22 (s, 1H) m/z=425.1 (M+1).

Example 5

(Trans-4-{4-[(7S)-4-amino-7-methyl-5-oxo-7,8-dihydropyrimido[5,4-f][1,4]oxazepin-6(5H)-yl]phenyl cyclohexyl)acetic acid

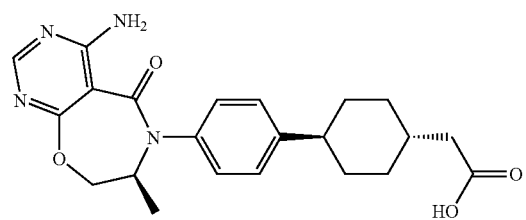

The compound (trans-4-{4-[(7S)-4-amino-7-methyl-5-oxo-7,8-dihydropyrimido[5,4-f][1,4]oxazepin-6(5H)-yl]phenyl cyclohexyl)acetic acid was prepared as follows.

Lithium hydroxide (11.3 mg, 0.472 mmol) was added to a solution of methyl (trans-4-{4-[(7S)-4-amino-7-methyl-5-oxo-7,8-dihydropyrimido[5,4-f][1,4]oxazepin-6(5H)-yl]phenyl cyclohexyl)acetate (50 mg, 0.12 mmol), from Example 4, in 2.76 ml of THF/methanol/water (3:2:1) and the resulting solution was stirred at room temperature. After completion, reaction was acidified with 1N NaOH until acidic pH, and concentrated reaction mixture. EtOAc and water were added, and repulped product for two hours. Filtered and dried to recover 2.1 mg of product. $^1$H NMR (400 MHz, DMSO-$d_6$) δ ppm 0.99-1.19 (m, 2H) 1.08 (d, 3H) 1.33-1.53 (m, 2H) 1.57-1.88 (m, 5H) 2.06 (d, J=6.65 Hz, 2H) 2.30-2.61 (m, 1H) 3.93-4.19 (m, 1H) 4.38-4.69 (m, 2H) 7.13 (d, J=8.31 Hz, 2H) 7.26 (d, J=8.31 Hz, 2H) 8.07 (s, 1H) m/z=411.2 (M+1). IC$_{50}$ 33.9 nM.

Example 6

2-(4-(4-(4-amino-5-oxo-7,8-dihydropyrimido[5,4-f][1,4]oxazepin-6(5H)-yl)-3-fluorophenyl)cyclohexyl)acetic Acid

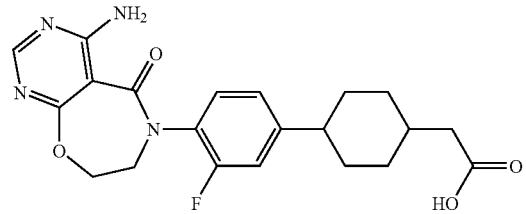

The title compound was prepared as follows. A mixture of methyl 2-(4-(4-(4-chloro-5-oxo-7,8-dihydropyrimido[5,4-f][1,4]oxazepin-6(5H)-yl)-3-fluorophenyl)cyclohexyl)acetate (20 mg, 0.045 mmol), from Preparation 4, in 0.5M ammonia in dioxane was stirred at 50° C., in a tightly capped flask, for 3 hours. The reaction mixture was concentrated to give a white solid, which was carried on to the next step without further purification. LiOH (4.5 mg, 0.18 mmol) was added to a solution of the white solid in THF/methanol/water (2.4 mL, 3:2:1) and the resulting solution was stirred at 23° C. for 16 hours. 1M HCl solution was added to reaction solution to adjust the pH about 3. 20% i-propanol in DCM (30 mL) was added to extract reaction mixture. The organic layer was separated and dried over MgSO$_4$ and concentrated to give a solid. Purification was done by chromatography (4 g, silica gel column) with methanol/DCM from 2-6% to give a white solid 12 mg as the title compound.

$^1$H NMR (400 MHz, CD3OD): δ 8.18 (s, 1H), 7.28 (m, 1H), 7.16 (m, 2H), 4.66 (m, 2H), 3.98 (m, 2H), 2.64-2.5 (m, 1H), 2.4, 2.2 (d, 2H), 2.22 (m, 1H), 1.90 (m, 2H), 1.7 (m, 4H), 1.54 (m, 2H), 1.2 (m, 2H). m/z=415.4 (M+1). IC$_{50}$ 55.5 nM (range 29.1-89.6 nM).

The compounds of the Examples 7-16, having the following structure, were prepared using the procedures described in Examples 1-4.

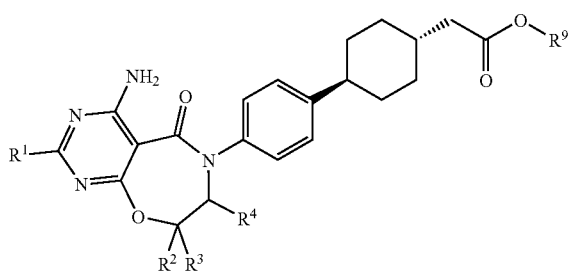

Example 7

($R^1$=H, $R^2$CH$_3$, $R^3$=CH$_3$, $R^4$=H, $R^9$=CH$_2$CH$_3$)—ethyl {trans-4-[4-(4-amino-8,8-dimethyl-5-oxo-7,8-dihydropyrimido[5,4-f][1,4]oxazepin-6(5H)-yl)phenyl]cyclohexyl}acetate m/z=453.3 (M+1) m/z=453.3 (M+1); IC$_{50}$ 183 nM

Example 8

($R^1$=H, $R^2$=CH$_3$, $R^3$=CH$_3$, $R^4$=H, $R^9$=H)-{trans-4-[4-(4-amino-8,8-dimethyl-5-oxo-7,8-dihydropyrimido[5,4-f][1,4]oxazepin-6(5H)-yl)phenyl]cyclohexyl}acetic acid $^1$H NMR (400 MHz, DMSO-d$_6$) δ 8.18 (s, 1H), 7.59 (br s, 1H) 7.20 (m, 4H), 3.79 (m, 2H), 2.42 (m, 1H), 2.08 (m, 2H), 1.78 (m, 4H), 1.67 (m, 1H), 1.43 (m, 2H), 1.24 (s, 6H), 1.05 (m, 2H). m/z=425.3 (M+1). IC$_{50}$ 146 nM (range 125.0-170.0 nM)

Example 9

($R^1$=CH$_3$, $R^2$=H, $R^3$=H, $R^4$=H, $R^9$=CH$_3$)— methyl {trans-4-[4-(4-amino-2-methyl-5-oxo-7,8-dihydropyrimido[5,4-f][1,4]oxazepin-6(5H)-yl)phenyl]cyclohexyl}acetate. $^1$H NMR (400 MHz, CHLOROFORM-d) ppm δ 1.04-1.32 (m, 2H) 1.39-1.56 (m, 2H) 1.77-1.98 (m, 5H) 2.15-2.32 (m, 2H) 2.38 (s, 0H) 2.41-2.60 (m, 4H) 3.68 (s, 3H) 3.91-4.03 (m, 2H) 4.56-4.73 (m, 2H) 5.60 (br. s., 1H) 7.12-7.22 (m, 2H) 7.22-7.36 (m, 2H) 8.23 (br. s., 1H); m/z=425.3 (M+1). IC$_{50}$ 239 nM

Example 10

($R^1$=CH$_3$, $R^2$=H, $R^3$=H, $R^4$=H, $R^9$=H)-{trans-4-[4-(4-amino-2-methyl-5-oxo-7,8-dihydropyrimido[5,4-f][1,4]oxazepin-6(5H)-l)phenyl]cyclohexyl}acetic acid $^1$H NMR (400 MHz, CDCl$_3$) δ 6.98 (m, 2H) 6.85 (m, 2H), 4.43 (m, 2H), 3.78 (m, 2H), 2.20 (m, 1H), 2.08 (s, 3H), 1.90 (m, 2H), 1.59 (m, 5H), 1.20 (m, 2H), 0.83 (m, 2H). m/z=411.4 (M+1). IC$_{50}$ 59.4 nM (range 49.9-78.2 nM)

Example 11

($R^1$=H, $R^2$=CH$_3$, $R^3$=H, $R^4$=H, $R^9$=H)-{4-[4-(4-Amino-8-methyl-5-oxo-7,8-dihydro-5H-9-oxa-1,3,6-triaza-benzocyclohepten-6-yl)-phenyl]-cyclohexyl}-acetic acid $^1$H NMR (400 MHz, METHANOL-d$_4$) δ ppm 1.11-1.27 (m, 2H) 1.37 (d, J=4.98 Hz, 3H) 1.46-1.62 (m, 2H) 1.76-2.00 (m, 5H) 2.21 (d, J=5.39 Hz, 2H) 2.45-2.61 (m, 1H) 3.80-3.98 (m, 2H) 4.93-5.05 (m, 1H) 7.20-7.28 (m, 2H) 7.29-7.36 (m, 2H) 8.17 (s, 1H) m/z=411.4, 409.5 (M+1). IC$_{50}$ 125 nM (range 52.8-492.0 nM)

Example 12

($R^1$=H, $R^2$=″″″″CH$_3$, $R^3$=H, $R^4$=H, $R^9$=H)-{4-[4-((S)-4-Amino-8-methyl-5-oxo-7,8-dihydro-5H-9-oxa-1,3,6-triaza-benzocyclohepten-6-yl)-phenyl]-cyclohexyl}-acetic acid $^1$H NMR (400 MHz, METHANOL-d$_4$) δ ppm 1.15-1.25 (m, 2H) 1.37 (d, J=6.64 Hz, 3H) 1.53 (q, J=12.75 Hz, 2H) 1.77-1.96 (m, 5H) 2.21 (d, J=7.03 Hz, 2H) 2.45-2.59 (m, 1H) 3.85-3.92 (m, 2H) 4.94-5.04 (m, 1H) 7.22-7.28 (m, 2H) 7.28-7.35 (m, 2H) 8.17 (s, 1H); m/z=411.4, 409.5 (M+1). IC$_{50}$ 625 nM

Example 13

($R^1$=H, $R^2$=CH$_2$CH$_3$, $R^3$=H, $R^4$=H, $R^9$=H)-{4-[4-(4-Amino-8-ethyl-5-oxo-7,8-dihydro-5H-9-oxa-1,3,6-triaza-benzocyclohepten-6-yl)-phenyl]-cyclohexyl}-acetic acid m/z=425.2 (M+1) IC$_{50}$ 1330 nM (range 1070-1660 nM)

Example 14

($R^1$=H, $R^2$=H, $R^3$=H, $R^4$=″″″″CH$_3$, $R^9$=H)-(trans-4-{4-[(7R)-4-amino-7-methyl-5-oxo-7,8-dihydropyrimido[5,4-f][1,4]-oxazepin-6(5H)-yl]phenyl cyclohexyl)acetic acid $^1$H NMR (400 MHz, DMSO-d6) δ ppm 1.00-1.16 (m, 2H) 1.08 (d, 3H) 1.34-1.52 (m, 2H) 1.67-1.86 (m, 5H) 2.11 (d, J=7.06 Hz, 2H) 2.36-2.45 (m, 1H) 4.00-4.11 (m, 1H) 4.44-4.54 (m, 1H) 4.61 (d, J=11.22 Hz, 1H) 7.14 (d, J=8.31 Hz, 2H) 7.26 (d, J=8.31 Hz, 2H) 8.07 (s, 1H), m/z=411.2 (M+1). IC$_{50}$ 24.7 nM (range 20.2-36.7 nM)

Example 15

($R^1$=H, $R^2$=H, $R^3$=H, $R^4$=CH$_3$, $R^9$=H)-{4-[4-(4-Amino-7-methyl-5-oxo-7,8-dihydro-5H-9-oxa-1,3,6-triaza-benzocyclohepten-6-yl)-phenyl]-cyclohexyl}-acetic acid 1H NMR (400 MHz, METHANOL-d4) δ ppm 1.08-1.34 (m, 2H) 1.26 (d, 3H) 1.45-1.63 (m, 2H) 1.76-2.01 (m, 5H) 2.22 (d, J=7.06 Hz, 2H) 2.54 (t, J=7.69 Hz, 1H) 4.16-4.37 (m, 2H) 4.65-4.87 (m, 2H) 7.17 (d, J=8.31 Hz, 2H) 7.33 (d, J=8.31 Hz, 2H) 8.24 (s, 1H) m/z=411.2 (M+1). IC$_{50}$ 27.3 nM (range 13.6-77.9 nM)

Example 16 shown below, {cis-4-[4-(4-amino-5-oxo-7,8-dihydropyrimido[5,4-f][1,4]oxazepin-6(5H)-yl)phenyl]cyclohexyl}acetic acid

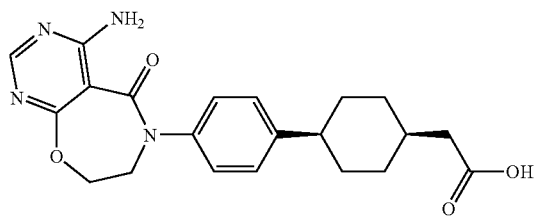

IC$_{50}$ 18.1 nM (range 16.0-20.5 nM)

The compounds of Examples 17-25, having one of the following structures, using starting materials prepared analogous to the method for preparing the compound of Preparation 4, were prepared my the method of Scheme 1 by the methods of Examples 3 and 6.

| Ex. | R$^3$ | R$^{5d}$ | R$^{5a}$ | DGAT-1 IC$_{50}$ (nM) | DGAT-1 IC$_{50}$ Range (nM) |
|---|---|---|---|---|---|
| 17 | CH$_3$ | H | F | <6.21 | <3-15.5 |
| 18 | H | H | Cl | 5.82 | 4.4-6.9 |
| 19 | H | H | F | <8.26 | <3-15.5 |
| 20 | H | H | CH$_3$ | 13 | 8.6-17.2 |
| 21 | CH$_3$ | H | CH$_3$ | 14.8 | 6.1-37.4 |
| 22 | CH$_3$ | F | H | 30 | 27.9-34.5 |
| 23 | H | CH$_3$ | H | 1410 | 643-2270 |

Example 17

(R)-2-(4-(4-(4-amino-8-methyl-5-oxo-7,8-dihydropyrimido[5,4-f][1,4]oxazepin-6(5H)-yl)-2-fluorophenyl)cyclohexyl)acetic acid (400 MHz, CD3OD): δ 8.18 (s, 1H), 7.38 (m, 1H), 7.10 (m, 2H), 4.96 (m, 1H), 3.90 (m, 2H), 2.9 (m, 1H), 2.8, 2.3 (m, 1H), 2.4, 2.2 (d, 2H), 1.90 (m, 2H), 1.7 (m, 2H), 1.54 (m, 2H), 1.4 (d, 3H), 1.2 (m, 2H)

Example 18

2-(4-(4-(4-amino-5-oxo-7,8-dihydropyrimido[5,4-f][1,4]oxazepin-6(5H)-yl)-2-chlorophenyl)cyclohexyl)acetic acid (400 MHz, CD3OD): δ 8.18 (s, 1H), 7.42 (m, 2H), 7.14 (m, 1H), 4.66 (m, 2H), 3.98 (m, 2H), 3.0 (m, 1H), 2.3 (m, 1H), 2.44, 2.2 (d, 2H), 1.95-1.42 (m, 6H), 1.2 (m, 1H)

Example 19

2-(4-(4-(4-amino-5-oxo-7,8-dihydropyrimido[5,4-f][1,4]oxazepin-6(5H)-yl)-2-fluorophenyl)cyclohexyl)acetic acid (400 MHz, CD3OD): δ 8.18 (s, 1H), 7.38 (m, 1H), 7.1 (m, 2H), 4.68 (m, 2H), 4.02 (m, 2H), 2.9 (m, 1H), 2.24 (m, 1H), 2.4, 2.2 (d, 2H), 1.90 (m, 2H), 1.7 (m, 2H), 1.54 (m, 2H), 1.2 (m, 2H)

Example 20

2-(4-(4-(4-amino-5-oxo-7,8-dihydropyrimido[5,4-f][1,4]oxazepin-6(5H)-yl)-2-methylphenyl)cyclohexyl)acetic acid (400 MHz, CD3OD): δ 8.18 (s, 1H), 7.32 (m, 1H), 7.08 (m, 2H), 4.68 (m, 2H), 3.98 (m, 2H), 2.78 (m, 1H), 2.38 (s, 3H), 2.32 (m, 1H), 2.4, 2.2 (d, 2H), 1.90-1.5 (m, 7H), 1.2 (m, 7H)

Example 21

(R)-2-(4-(4-(4-amino-8-methyl-5-oxo-7,8-dihydropyrimido[5,4-f][1,4]oxazepin-6(5H)-yl)-2-methylphenyl)cyclohexyl)acetic acid (400 MHz, CD3OD): δ 8.18 (s, 1H), 7.36 (m, 1H), 7.10 (m, 2H), 4.96 (m, 1H), 3.92 (m, 2H), 2.78 (m, 1H), 2.34 (s, 3H), 2.3 (m, 1H), 2.5, 2.2 (d, 2H), 1.90 (m, 1H), 1.7 (m, 3H), 1.54 (m, 3H), 1.38 (d, 3H), 1.2 (m, 1H)

Example 22

(R)-2-(4-(4-(4-amino-8-methyl-5-oxo-7,8-dihydropyrimido[5,4-f][1,4]oxazepin-6(5H)-yl)-3-fluorophenyl)cyclohexyl)acetic acid (400 MHz, CD3OD): δ 8.18 (s, 1H), 7.28 (m, 1H), 7.08 (m, 2H), 4.96 (m, 1H), 3.92 (m, 2H), 2.6 (m, 1H), 2.4, 2.2 (d, 2H), 2.3 (m, 1H), 1.90 (m, 2H), 1.7 (m, 4H), 1.5 (m, 1H), 1.4 (d, 3H), 1.2 (m, 1H)

Example 23

2-(4-(4-(4-amino-5-oxo-7,8-dihydropyrimido[5,4-f][1,4]-oxazepin-6(5H)-yl)-3-methylphenyl)cyclohexyl)acetic acid-1H NMR (400 MHz, METHANOL-d$_4$) δ ppm 1.12-1.25 (m, 1H) 1.45-1.59 (m, 1H) 1.62-1.76 (m, 3H) 1.88 (t, J=15.61 Hz, 3H) 2.22 (d, J=3.51 Hz, 3H) 2.26 (d, J=3.90 Hz, 1H) 2.43 (d, J=7.81 Hz, 2H) 2.46-2.55 (m, 1H) 3.78-4.05 (m, 2H) 4.60-4.78 (m, 2H) 7.07-7.26 (m, 3H) 8.16 (s, 1H); LCMS was 411.4 (t=2.0 min).

Examples 24-25

| Ex. |  | R$^3$ | R$^{5d}$ | R$^{5a}$ | DGAT-1 IC$_{50}$ (nM) | DGAT-1 IC$_{50}$ Range (nM) |
|---|---|---|---|---|---|---|
| 24 | Cis | CH$_3$ | H | F | 4.6 | 1.7-13.2 |
| 25 | Trans | CH$_3$ | H | F | 12.3 | 10.0-17.0 |

Example 24

(cis-4-{4-[(8R)-4-amino-8-methyl-5-oxo-7,8-dihydropyrimido[5,4-f][1,4]oxazepin-6(5H)-yl]-2-fluorophenyl}cyclohexyl)acetic acid (400 MHz, CD3OD): δ 8.18 (s, 1H), 7.38 (m, 1H), 7.10 (m, 2H), 4.96 (m, 1H), 3.90 (m, 2H), 2.9 (m, 1H), 2.4 (d, 2H), 2.3 (m, 1H), 1.90 (m, 1H), 1.7-1.5 (m, 6H), 1.4 (d, 3H), 1.2 (m, 1H)

Example 25

(trans-4-{4-[(8R)-4-amino-8-methyl-5-oxo-7,8-dihydropyrimido[5,4-f][1,4]oxazepin-6(5H)-yl]-2-fluorophenyl}cyclohexyl)acetic acid (400 MHz, CD3OD): δ 8.18 (s, 1H), 7.38 (m, 1H), 7.10 (m, 2H), 4.96 (m, 1H), 3.88 (m, 2H), 2.8 (m, 1H), 2.2 (d, 2H), 1.90 (m, 5H), 1.58 (q, 2H), 1.4 (d, 3H), 1.2 (m, 2H).

Example 26

2-{Trans-4-[4-(4-amino-5-oxo-7,8-dihydropyrimido[5,4-f][1,4]oxazepin-6(5H)-yl)phenyl]cyclohexyl}-N-(methylsulfonyl)acetamide

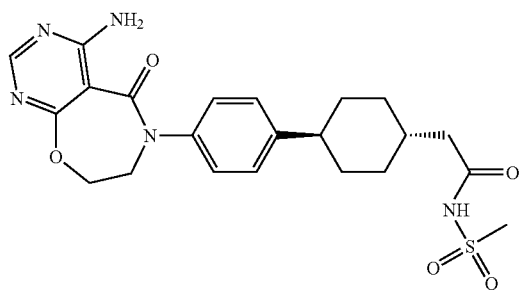

The compound 2-{trans-4-[4-(4-amino-5-oxo-7,8-dihydropyrimido[5,4-f][1,4]oxazepin-6(5H)-yl)phenyl]cyclohexyl}-N-(methylsulfonyl)acetamide was prepared as follows.

To a stirred solution of {trans-4-[4-(4-amino-5-oxo-7,8-dihydropyrimido[5,4-f][1,4]oxazepin-6(5H)-yl)phenyl]cyclohexyl}acetic acid (50 mg, 0.13 mmol), from Example 2, N-methylsulfonamide (30 mg, 0.32 mmol) were added HOBT (29 mg, 0.19 mmol), EDCl (30 mg, 0.32 mmol) and TEA (19.1 mg, 0.19 mmol). After 18 hours, the reaction mixture was diluted into EtOAc, washed with water, dried over sodium sulfate and concentrated in vacuo. Reverse-phase chromatography afforded the desired product as a white solid, 5.3 mg. $^1$H NMR (400 MHz, DMSO-$d_6$): δ 8.17 (s, 1H), 7.64 (br s, 2H) 7.20 (s, 4H), 4.58 (m, 2H), 3.92 (m, 2H), 3.20 (s, 3H), 2.42 (m, 1H), 2.17 (m, 2H), 1.73 (m, 5H), 1.40 (m, 2H), 1.05 m, 2H). m/z=474.4 (M+1). IC$_{50}$ 44.5 nM (range 34.2-75.0 nM).

Example 27

(Trans-4-{4-[(8R)-4-amino-8-methyl-5-oxo-7,8-dihydropyrimido[5,4-f][1,4]oxazepin-6(5H)-yl]phenyl}cyclohexyl)acetamide

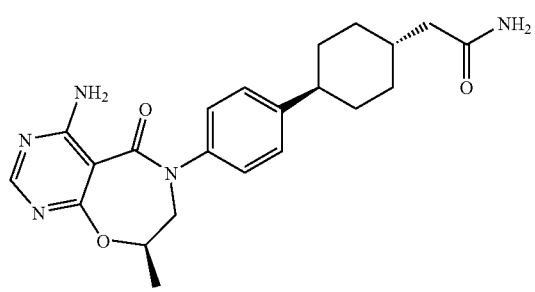

The compound 2-((1S,4s)-4-(4-((R)-4-amino-8-methyl-5-oxo-7,8-dihydropyrimido[5,4-f][1,4]oxazepin-6(5H)-yl)phenyl)cyclohexyl)acetamide was prepared as follows.

(Trans-4-{4-[(8R)-4-amino-8-methyl-5-oxo-7,8-dihydropyrimido[5,4-f]-[1,4]oxazepin-6(5H)-yl]phenyl}cyclohexyl)acetic acid (1100 mg, 2.68 mmol), from Example 3, was added into DCM (20 mL) and DMF (0.02 mL). Oxalyl chloride (0.47 mL, 5.36 mmol) was then added dropwise at 0° C., and the resulting mixture was warmed to room temperature and stirred for 2 hours. The mixture was concentrated to afforded a pale yellow solid (acyl chloride) and dried on a vacuum pump for 1 hour. The acyl chloride was then dissolved in 30 mL of 0.5N NH$_3$ in dioxane and the reaction was stirred for 90 minutes. 20% i-propanol in DCM (130 mL) and water (100 mL) were added to reaction mixture. The organic layer was separated and dried over MgSO$_4$ and concentrated to give a solid. Purification was done by chromatography (80 g, silica gel column) with methanol/DCM from 2-10% to give a white solid 950 mg (87%) as the title compound. m/z=410.1 (M+1). $^1$H NMR (400 MHz, METHANOL-$d_4$) δ ppm 1.10-1.24 (m, 2H) 1.36 (d, J=6.24 Hz, 3H) 1.45-1.60 (m, 2H) 1.73-1.95 (m, 5H) 2.12 (d, J=7.03 Hz, 2H) 2.52 (t, J=12.29 Hz, 1H) 3.80-3.96 (m, 2H) 4.92-5.03 (m, 1H) 7.22-7.27 (m, 2H) 7.27-7.34 (m, 2H) 8.17 (s, 1H). IC$_{50}$ 52.2 nM (range 11.4-68.1 nM).

The compounds of the following Examples 28-46 were prepared utilizing the method of Examples 26-27 wherein an amide is formed by reacting a carboxylic acid with an amine. The compounds of Examples 33-44 were separated using reverse phase column chromatography utilizing YMC ODS-AQ (2.0×50 mm 5 µm), which is a reversed-phase packing material with both a hydrophobic high carbon loading and a relatively hydrophilic surface (YMC Co., Ltd., Tokyo, Japan) and 0.05% TFA in water as an eluent.

Example 28
(R)-2-(4-(4-(4-amino-8-methyl-5-oxo-7,8-dihydro-pyrimido[5,4-f][1,4]oxazepin-6(5H)-yl)-2-fluorophenyl)cyclohexyl)acetamide
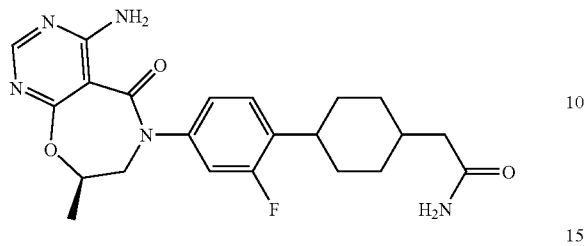
The titled compound was prepared by the methods of Examples 6 and 27. 1H NMR (400 MHz, DMSO): δ 8.18 (s, 1H), 7.6 (br s, 1H), 7.34 (m, 3H), 7.20 (m, 2H), 6.72 (br s, 1H), 4.9 (m, 1H), 3.82 (m, 2H), 2.87 (m, 1H), 2.2 (m, 3H), 1.7-1.44 (m, 8H), 1.2 (d, 3H). $IC_{50}$ 11.3 nM (range 7.3-19.9 nM).
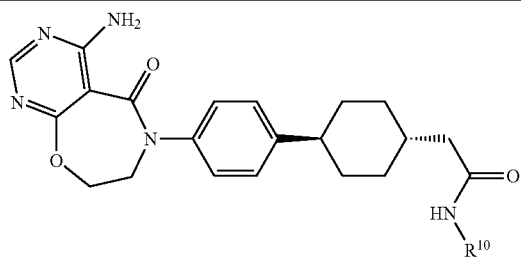
| Ex. | $R^{10}$ | DGAT-1 $IC_{50}$ (nM) | Ex. | $R^{10}$ | DGAT-1 $IC_{50}$ (nM) | $IC_{50}$ Range (nM) |
|---|---|---|---|---|---|---|
| 29 | S(O)$_2$CF$_3$ | 57.9 | 30 | H | 31.7 | 11.4-68.1 |
| 31 | Tetrazole | 18.3 | 32 | CH$_2$CH$_3$ | 93.7 | 68.6-135.0 |
| 33 | Cyclohexyl | 11.1 | 34 | cyclopentyl | 64.3 | |
| 35 | 2-indanyl | 24.9 | 36 | t-butyl | 164 | 65.1-394.0 |
| 37 | | 81.5 | 38 | | 54.1 | |
| 39 | | 56.8 | 40 | | 51.5 | |
| 41 | | 65.3 | 42 | | 69.9 | |
| 43 | | 55.8 | 44 | CH$_3$ | 85.5 | 41.1-72.1 |
| 45 | | 43.5 | 46 | i-propyl | 76.9 | 58.1-104 |

Example 29

2-{Trans-4-[4-(4-amino-5-oxo-7,8-dihydropyrimido[5,4-f][1,4]oxazepin-6(5H)-yl)phenyl]cyclohexyl}-N-[(trifluoromethyl)sulfonyl]acetamide $^1$H NMR (400 MHz, DMSO-$d_6$): δ 8.23 (s, 1H), 8.10 (br s, 2H) 7.22 (m, 4H), 4.62 (m, 2H), 3.99 (m, 2H), 2.40 (m, 1H), 2.01 (m, 2H), 1.71 (m, 5H), 1.39 (m, 2H), 1.00 (m, 2H). m/z=528.4 (M+1)

Example 30

2-{Trans-4-[4-(4-amino-5-oxo-7,8-dihydropyrimido[5,4-f][1,4]oxazepin-6(5H)-yl)phenyl]cyclohexyl}acetamide $^1$H NMR (400 MHz, DMSO-$d_6$): δ 8.17 (s, 1H), 7.59 (br s, 2H) 7.24 (s, 4H), 4.58 (m, 2H), 3.96 (m, 2H), 2.44 (m, 1H), 1.97 (m, 2H), 1.78 (m, 4H), 1.68 (m, 1H), 1.42 (m, 2H), 1.03 (m, 2H). m/z=396.2 (M+1)

Example 31

2-{Trans-4-[4-(4-amino-5-oxo-7,8-dihydropyrimido[5,4-f][1,4]oxazepin-6(5H)-yl)phenyl]cyclohexyl}-N-1H-tetrazol-5-ylacetamide $^1$H NMR (400 MHz, DMSO-$d_6$): δ 8.17 (s, 1H), 7.63 (br s, 2H) 7.22 (m, 4H), 4.57 (m, 2H), 3.90 (m, 2H), 2.40 (m, 1H), 2.33 (m, 2H), 1.78 (m, 5H), 1.40 (m, 2H), 1.10 (m, 2H). m/z=464.4 (M+1)

Example 32

2-{trans-4-[4-(4-amino-5-oxo-7,8-dihydropyrimido[5,4-f][1,4]oxazepin-6(5H)-yl)phenyl]cyclohexyl}-N-ethylacetamide $^1$H NMR (400 MHz, DMSO-d6) δ ppm 8.11 (s, 1H) 7.74 (t, J=5.39 Hz, 1H) 7.55 (br. s., 2H) 7.18-7.27 (m, 4H) 4.49-4.57 (m, 2H) 3.86-3.95 (m, 2H) 2.94-3.06 (m, 2H) 2.36-2.48 (m, 1H) 1.92 (d, J=6.64 Hz, 1H) 1.73 (t, J=9.75 Hz, 6H) 1.32-1.48 (m, 2H) 0.88-1.09 (m, 5H)

Example 33

2-{trans-4-[4-(4-amino-5-oxo-7,8-dihydropyrimido[5,4-f]-[1,4]oxazepin-6(5H)-yl)phenyl]cyclohexyl}-N-cyclohexylacetamide Mass Spectrum M/Z (M+1) 478; RT=2.843

Example 34

2-{trans-4-[4-(4-amino-5-oxo-7,8-dihydropyrimido[5,4-f]-[1,4]oxazepin-6(5H)-yl)phenyl]cyclohexyl}-N-cyclopentylacetamide Mass Spectrum M/Z (M+1) 464; RT=2.6

Example 35

2-{trans-4-[4-(4-amino-5-oxo-7,8-dihydropyrimido[5,4-f]-[1,4]oxazepin-6(5H)-yl)phenyl]cyclohexyl}-N-2-indanyl-acetamide Mass Spectrum M/Z (M+1) 512; RT=2.586

Example 36

2-{trans-4-(4-(4-amino-5-oxo-7,8-dihydropyrimido[5,4-f]-[1,4]oxazepin-6(5H)-yl)phenyl)cyclohexyl}-N-tert-butylacetamide Mass Spectrum M/Z (M+1) 452; RT=2.633

Example 37

2-{trans-4-[4-(4-amino-5-oxo-7,8-dihydropyrimido[5,4-f]-[1,4]oxazepin-6(5H)-yl)phenyl]cyclohexyl}-N-[(1S)-1,2,2-trimethylpropyl]acetamide Mass Spectrum M/Z (M+1) 480; RT=2.597

Example 38

2-{trans-4-[4-(4-amino-5-oxo-7,8-dihydropyrimido[5,4-f]-[1,4]oxazepin-6(5H)-yl)phenyl]cyclohexyl}-N-(1,1-dimethylpropyl)acetamide Mass Spectrum M/Z (M+1) 466; RT=2.763

Example 39

2-{trans-4-[4-(4-amino-5-oxo-7,8-dihydropyrimido[5,4-f]-[1,4]oxazepin-6(5H)-yl)phenyl]cyclohexyl}-N-(2,2-dimethylpropyl)acetamide Mass Spectrum M/Z (M+1) 466; RT=2.498

Example 40

2-{trans-4-[4-(4-amino-5-oxo-7,8-dihydropyrimido[5,4-f]-[1,4]oxazepin-6(5H)-yl)phenyl]cyclohexyl}-N-[(2S)-2-methylbutyl]acetamide Mass Spectrum M/Z (M+1) 466; RT=2.508

Example 41

2-{trans-4-[4-(4-amino-5-oxo-7,8-dihydropyrimido[5,4-f]-[1,4]oxazepin-6(5H)-yl)phenyl]cyclohexyl}-N-(1-ethylpropyl)acetamide Mass Spectrum M/Z (M+1) 466; RT=2.463

Example 42

2-{trans-4-[4-(4-amino-5-oxo-7,8-dihydropyrimido[5,4-f]-[1,4]oxazepin-6(5H)-yl)phenyl]cyclohexyl}-N-(1,2-dimethylpropyl)acetamide Mass Spectrum M/Z (M+1) 466; RT=2.991

Example 43

2-{trans-4-[4-(4-amino-5-oxo-7,8-dihydropyrimido[5,4-f]-[1,4]oxazepin-6(5H)-yl)phenyl]cyclohexyl}-N-[(1S)-1-methylbutyl]acetamide Mass Spectrum M/Z (M+1) 466; RT=2.808

Example 44

2-{4-[4-(4-Amino-5-oxo-7,8-dihydro-5H-9-oxa-1,3,6-triaza-benzocyclohepten-6-yl)-phenyl]-cyclohexyl}-N-methyl-acetamide 1H NMR (400 MHz, DMSO-$d_6$) δ ppm 0.89-1.15 (m, 2H) 1.30-1.50 (m, 2H) 1.59-1.83 (m, 5H) 1.85-1.98 (m, 2H) 2.39-2.59 (m, 2H) 3.02-3.38 (m, 3H) 3.83-3.96 (m, 2H) 4.46-4.59 (m, 2H) 7.15-7.29 (m, 2H) 7.47-7.59 (m, 2H) 7.66 (br. s., 2H) 8.11 (s, 1H).

Example 45

2-{trans-4-[4-(4-amino-5-oxo-7,8-dihydropyrimido[5,4-f]-[1,4]oxazepin-6(5H)-yl)phenyl]cyclohexyl}-N-(2-methylbutyl)acetamide Mass Spectrum M/Z (M+1) 466; RT=2.822

Example 46

{Trans-4-[4-(4-amino-5-oxo-7,8-dihydropyrimido[5,4-f][1,4]oxazepin-6(5H)-yl)phenyl]cyclohexyl}acetonitrile

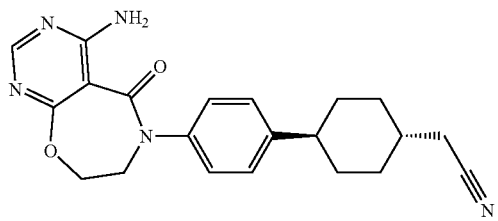

The compound {trans-4-[4-(4-amino-5-oxo-7,8-dihydropyrimido[5,4-f][1,4]oxazepin-6(5H)-yl)phenyl]cyclohexyl}acetonitrile was prepared as follows.

To a stirred slurry of 2-{trans-4-[4-(4-amino-5-oxo-7,8-dihydropyrimido[5,4-f][1,4]oxazepin-6(5H)-yl)phenyl]cyclohexyl}acetamide (45 mg, 0.11 mmol), from Example 30, in THF (1 mL) was added DMF (0.002 mL) and oxalyl chloride (0.05 mL, 0.6 mmol). After two hours of stirring at room temperature, the reaction was quenched with aqueous sodium bicarbonate and extracted with EtOAc. The organic layer was washed with water, dried over sodium sulfate and concentrated in vacuo to afford the title compound as a light-yellow colored solid, 34 mg. $^1$H NMR (400 MHz, DMSO-$d_6$): δ 8.17 (s, 1H), 7.63 (br s, 2H) 7.22 (m, 4H), 4.57 (m, 2H), 3.90 (m, 2H), 2.43 (m, 3H), 1.78 (m, 4H), 1.63 (m, 1H), 1.43 (m, 2H), 1.08 (m, 2H). m/z=378.3 (M+1). $IC_{50}$ 64.3 nM (range 51.2-91.1 nM).

Example 47

(Trans-4-{4-[(8R)-4-amino-8-methyl-5-oxo-7,8-dihydropyrimido[5,4-f][1,4]oxazepin-6(5H)-yl]phenyl}cyclohexyl)acetonitrile

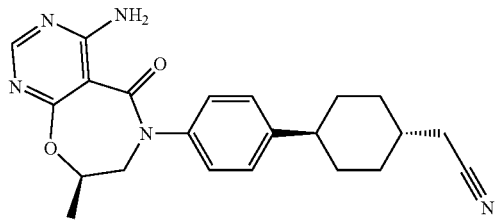

The compound (trans-4-{4-[(8R)-4-amino-8-methyl-5-oxo-7,8-dihydropyrimido[5,4-f][1,4]oxazepin-6(5H)-yl]phenyl}cyclohexyl)acetonitrile was prepared as follows.

(Trans-4-{4-[(8R)-4-amino-8-methyl-5-oxo-7,8-dihydropyrimido[5,4-f][1,4]oxazepin-6(5H)-yl]phenyl}cyclohexyl)acetic acid, from Example 27, (500 mg, 1.22 mmol) was dissolved in THF (12 mL) and DMF (0.01 mL, 0.12 mmol), and oxalyl chloride (0.5 mL, 6 mmol) was added dropwise to it at room temperature and the resulting mixture was stirred at room temperature for 2 hours. The reaction mixture was quenched with a carefully added NaHCO$_3$ solution and water, and then was extracted with EtOAc (2×100 mL). The organic layers were combined and washed with water, dried over MgSO$_4$ and concentrated to give some crude product. The material was chromatographed on 40 g silica gel column with 1-5% methanol/DCM to give 250 mg (53%) white solid as the title compound. m/z=392.2 (M+1). $^1$H NMR (400 MHz, chloroform-d) δ 1.19-1.37 (m, 2H) 1.42-1.58 (m, 5H) 1.69-1.84 (m, 1H) 1.90-2.05 (m, 4H) 2.31 (d, J=6.65 Hz, 2H) 2.46-2.60 (m, 1H) 3.76-3.96 (m, 2H) 4.86-5.00 (m, 1H) 5.58 (br. s., 1H) 7.20 (d, 2H) 7.27 (d, 2H) 7.99 (br. s., 1H) 8.29 (s, 1H). $IC_{50}$ 38.4 nM (range 30.1-48.1 nM).

Example 48

(R)-2-(4-(4-(4-amino-8-methyl-5-oxo-7,8-dihydropyrimido[5,4-f][1,4]oxazepin-6(5H)-yl)-2-fluorophenyl)cyclohexyl)acetonitrile

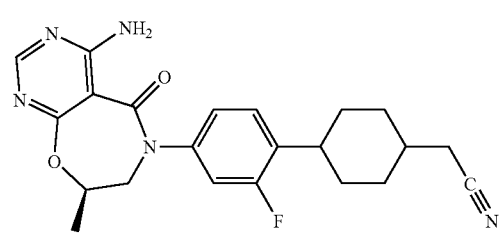

The titled compound was prepared by the methods of Examples 6 and 47. 1H NMR (400 MHz, CD3OD): δ 8.18 (s, 1H), 7.38 (m, 1H), 7.10 (m, 2H), 4.96 (m, 1H), 3.90 (m, 2H), 2.84 (m, 1H), 2.6, 2.4 (d, 2H), 1.96-1.56 (m, 4H), 1.4 (d, 3H), 1.28 (m, 1H), 0.88 (m, 4H). $IC_{50}$ 12.9 nM (range 4.5-22.2 nM).

Example 49

4-[4-(4-Amino-5-oxo-7,8-dihydro-5H-9-oxa-1,3,6-triaza-benzocyclohepten-6-yl)-phenyl]-cyclohexanecarboxylic Acid

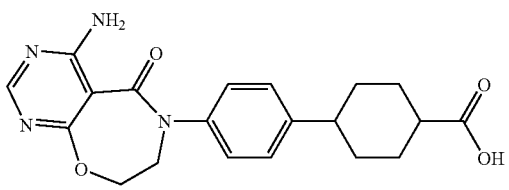

Prepared according the methods described in Example 1. $^1$H NMR (400 MHz, DMSO-d6) δ ppm 1.37-1.55 (m, 4H) 1.81 (br. s., 2H) 1.99 (br. s., 2H) 2.25 (br. s., 2H) 3.85-4.03 (m, 2H) 4.45-4.61 (m, 2H) 7.20-7.32 (m, 4H) 7.58 (s, 2H) 8.15 (s, 1H). m/z=381 (M−1). $IC_{50}$ 7.8 nM (range 5.8-10.5 nM)

Example 50

4-[4-(4-Amino-5-oxo-7,8-dihydro-5H-9-oxa-1,3,6-triaza-benzocyclohepten-6-yl)-phenyl]-cyclohexanecarboxylic Acid Methyl Ester

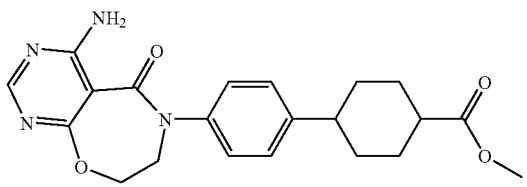

Prepared according the methods described in Example 1. ¹H NMR (400 MHz, CHLOROFORM-d) δ ppm 1.32-1.68 (m, 5H) 1.87-1.98 (m, 2H) 2.03-2.14 (m, 2H) 2.22-2.38 (m, 1H) 2.46-2.58 (m, 1H) 3.59-3.70 (m, 2H) 3.91-4.03 (m, 2H) 4.55-4.72 (m, 2H) 5.64 (br. s., 1H) 7.10-7.30 (m, 4H) 8.14 (br. s., 1H) 8.25 (s, 1H). m/z=397.4 (M+1). IC$_{50}$ 47.3 nM (range 45.2-49.5 nM)

Example 51

4-Amino-6-{4-[4-(1H-tetrazol-5-ylmethyl)-cyclohexyl]-phenyl}-7,8-dihydro-6H-9-oxa-1,3,6-triazabenzocyclohepten-5-one

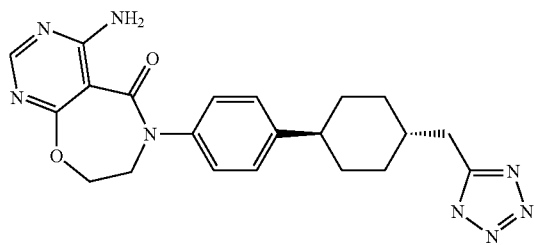

To a cooled 0° C., stirred solution of trimethylaluminum (2M in toluene, 0.33 mL) in toluene (0.66 mL) were added trimethylsilylazide (0.86 mL) and {trans-4-[4-(4-amino-5-oxo-7,8-dihydropyrimido[5,4-f][1,4]oxazepin-6(5H)-yl) phenyl]cyclohexyl}acetonitrile (25 mg). This mixture was heated at 80° C. for 40 hours, cooled, concentrated in vacuo and chromatographed (4 g silica gel column, 0-10% methanol:chloroform) to afford the title compound as a white solid, 2.8 mg. 1H NMR (400 MHz, DMSO-d$_6$) δ ppm 0.96-1.28 (m, 2 H) 1.25-1.45 (m, 2H) 1.62-1.80 (m, 5H) 2.31-2.50 (m, 1H) 2.62-2.76 (m, 2H) 3.85-3.95 (m, 2H) 4.45-4.57 (m, 2H) 7.13-7.29 (m, 4H) 7.55 (br. s., 2H) 8.10 (s, 1H) m/z=421.3 (M+1). IC$_{50}$ 76.2 nM (range 47.5-163 nM).

The following compounds of the present invention, as described in Examples 52-57, were prepared, or were derived from compounds prepared, by the method of Scheme 2 using the compound of Preparation 5.

Preparation 5

4-Amino-6-(4-iodophenyl)-7,8-dihydropyrimido[5,4-f][1,4]oxazepin-5(6H)-one

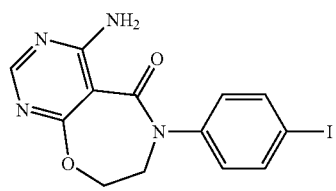

4-Amino-6-(4-iodophenyl)-7,8-dihydropyrimido[5,4-f][1,4]oxazepin-5(6H)-one was prepared as follows.

Step 1. N-(2-{[Tert-butyl(dimethyl)silyl]oxy}ethyl)-4-iodoaniline, shown below, was prepared as follows,

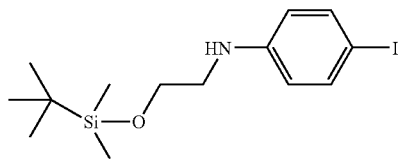

To a stirred slurry of sodium hydride (464 mg 60% in oil, 11.6 mmol) in THF (5 mL) was added a solution of 4-iodoaniline (1.27 grams, 5.80 mmol) in THF (1 mL) dropwise. After 15 minutes, (2-bromoethoxy)(tert-butyl)dimethyl silane (1.39 g, 5.83 mmol) was added and the resulting slurry was stirred for 40 hours. The reaction was quenched with water, partitioned between EtOAc and saturated aqueous ammonium chloride. The aqueous layer was washed with EtOAc (2×) and the combined organic layers were saturated aqueous brine, dried over magnesium sulfate and concentrated in vacuo to afford an oil. Chromatography (40 grams silica gel column, 0-20% EtOAc:heptane) afforded the title compound as a gummy solid, 1.41 grams. ¹H NMR (400 MHz, CDCl$_3$): δ 7.41, (d, 2H), 6.40 (d, 2H), 4.08 (br s, 1H), 3.81 (m, 2H), 3.18 0.92 (s, 9H), 0.04 (d, 6H). m/z=378.2 (M+1).

Step 2. 4,6-Dichloro-N-(2-hydroxyethyl)-N-(4-iodophenyl)pyrimidine-5-carboxamide, shown below, was prepared as follows,

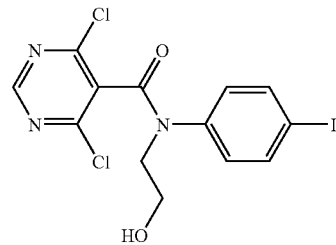

To a cooled (ice/water), stirred solution of N-(2-{[tert-butyl(dimethyl)silyl]oxy}ethyl)-4-iodoaniline (1.34 g, 2.78 mmol) and diethylisopropylamine (0.7 mL, 4.0 mmol) in MTHF (5 mL) was added 4,6-dichloroprimidine-5-carbonyl chloride (560 mg, 2.65 mmol). After 5 minutes, the cooling bath was removed and the slurry was stirred for 5 hours. Aqueous hydrochloric acid (1N, 5 mL) was added and the mixture was allowed to stand for 72 hours. The layers were separated and the aqueous layer was washed with MTHF (2×). The combined organic layers were washed with saturated aqueous sodium bicarbonate, saturated aqueous brine, dried over sodium sulfate and concentrated in vacuo to afford an oil. Chromatography (40 g silica gel column, 20-100% EtOAc:heptane) afforded the title compound, 542 mg. 1H NMR (400 MHz, CDCl$_3$) δ 8.64 (s, 1H), 7.62 (d, 2H), 7.17 (d, 2H), 4.07 (t, 2H), 3.91 (q, 2H). m/z=438.0 (M+1).

Step 3. 4-Chloro-6-(4-iodophenyl)-7,8-dihydropyrimido[5,4-f][1,4]oxazepin-5(6H)-one, shown below, was prepared as follows.

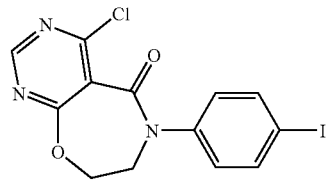

A stirred slurry of 4,6-dichloro-N-(2-hydroxyethyl)-N-(4-iodophenyl)pyrimidine-5-carboxamide (543 mg, 1.24 mmol) and potassium carbonate (350 mg, 2.53 mmol) in DMF was heated at 80° C. for 2 hours. The reaction was cooled, filtered, solids washed with small portion of DMF and the combined filtrates were concentrated in vacuo. The residue was chromatographed (40 g of silica gel, 0-70% EtOAc:heptane) to afford 4-chloro-6-(4-iodophenyl)-7,8-dihydropyrimido[5,4-f][1,4]oxazepin-5(6H)-one as a white solid, 427 mg. $^1$H NMR (400 MHz, CDCl$_3$) δ 8.78 (s, 1H), 7.80 (d, 2H), 7.17 (d, 2H), 4.77 (m, 2H), 4.03 (m, 2H). m/z=402.0 (M+1).

Step 4. A solution of 4-chloro-6-(4-iodophenyl)-7,8-dihydropyrimido[5,4-f][1,4]oxazepin-5(6H)-one (279 mg, 0.70 mmol) in 0.5 N ammonia in p-dioxane was stirred in a sealed tube for 18 hours. Concentration of the reaction mixture, followed by chromatography (10 g silica gel, 0-5% methanol:chloroform) afforded the title compound of Preparation 5 as a white solid, 122 mg. $^1$H NMR (400 MHz, DMSO-d6) δ 8.18 (s, 1H), 7.80 (d, 2H), 7.60 (br s, 2H), 7.19 (d, 2H), 4.60 (m, 2H), 3.96 (m, 2H). m/z=383.1 (M+1).

Example 52

Methyl(+)-{4-[4-(4-Amino-5-oxo-7,8-dihydropyrimido[5,4-f][1,4]oxazepin-6(5H)-yl)phenyl]cyclohex-3-en-1-yl}acetate

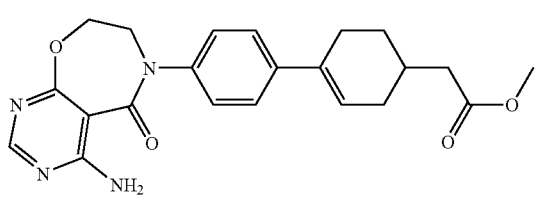

Methyl(±)-{4-[4-(4-Amino-5-oxo-7,8-dihydropyrimido[5,4-f][1,4]oxazepin-6(5H)-yl)phenyl]cyclohex-3-en-1-yl}acetate, shown above, was prepared as follows.

A stirred solution of 4-amino-6-(4-iodophenyl)-7,8-dihydropyrimido[5,4-f][1,4]oxazepin-5(6H)-one (40 mg, 0.10 mmol), methyl[4-(4,4,5,5-tetramethyl-1,3,2-dioxaborolan-2-yl)cyclohex-3-en-1-yl]acetate (38 mg, 0.14 mmol), cesium carbonate (42 mg, 0.28 mmol) and palladium tetrakis(triphenyl-phosphine) (6 mg, 0.005 mmol) in 1,2-dimethoxyethane (1.0 mL) was heated at 100° C. for 18 hours. The reaction mixture was cooled, concentrated and chromatographed to afford a white solid, 19 mg. IC$_{50}$ 84.3 nM.

Example 53

(+)-{4-[4-(4-Amino-5-oxo-7,8-dihydropyrimido[5,4-f][1,4]oxazepin-6(5H)-yl)phenyl]cyclohex-3-en-1-yl}acetic Acid

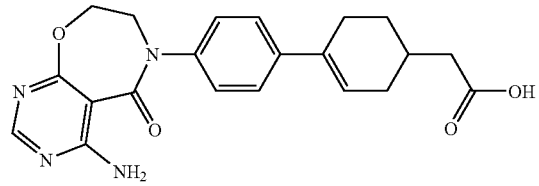

To form the named compound, shown above, the compound of Example 52 was hydrolyzed utilizing the conditions described in Example 2 to afford the title compound as light brown solid, 11 mg. $^1$H NMR (400 MHz, DMSO-d$_6$) δ 12.07 (br. s., 1H), 8.16 (s, 1H), 7.61 (br. s., 2H), 7.44 (d, J=8.30 Hz, 2H), 7.31 (d, 2H), 6.13 (br. s., 1H), 4.58 (t, 2H), 3.97 (br. s., 2H), 2.42 (br. s., 2H), 2.32 (d, 2H), 2.23 (d, 2H), 1.92-2.03 (m, 1H), 1.83-1.93 (m, 1H), 1.31-1.45 (m, 1H). m/z=395.3 (M+1). IC$_{50}$ 36.4 nM (range 33.8-39.3 nM).

Example 54

Methyl {4-[4-(4-amino-5-oxo-7,8-dihydropyrimido[5,4-f][1,4]oxazepin-6(5H)-yl)phenoxy]phenyl}acetate

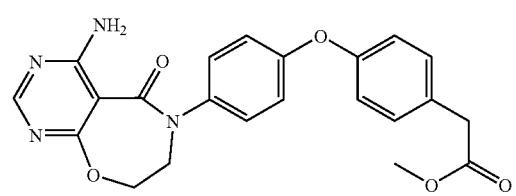

A stirred slurry of 4-amino-6-(4-iodophenyl)-7,8-dihydropyrimido[5,4-f][1,4]oxazepin-5(6H)-one (38 mg, 0.10 mmol), methyl 4-hydroxyphenylacetic acid (25 mg, 0.15 mmol), cesium carbonate (78 mg, 0.24 mmol), N,N-dimethyl glycine (10.3 mg, 0.10 mmol) and copper (I) iodide (6 mg, 0.03 mmol) in p-dioxane (0.4 mL) were heated at 90° C. for 18 hours. The reaction mixture was cooled, concentrated in vacuo and chromatographed (0-5% methanol: chloroform) to afford the title compound as a solid, 2.4 mg. $^1$H NMR (400 MHz, CDCl$_3$) δ 8.31 (s, 1H), 7.25 (d, 2H), 7.20 (d, 2H), 7.07 (d, 2H), 7.02 (d, 2H), 4.69 (m, 2H), 4.00 (m, 2H), 3.68 (s, 3H). m/z=421.2 (M+1). IC$_{50}$ 254 nM.

Example 55

±{(1R,3aS,4R,6aR)₄-[4-(4-Amino-5-oxo-7,8-dihydropyrimido[5,4-f][1,4]oxazepin-6(5H)-yl)phenyl]octahydropentalen-1-yl}acetic Acid

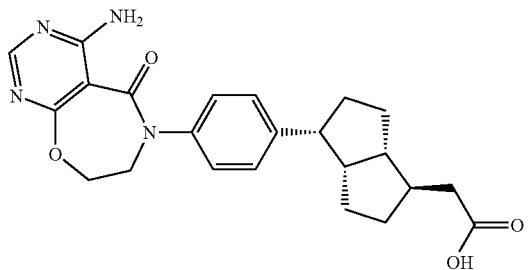

The named compound, shown above, was prepared as follows.

Step 1. Dimethyl(±)-{(1R,3aS,4R,6aS)-4-[4-(4-amino-5-oxo-7,8-dihydro pyrimido[5,4-f][1,4]oxazepin-6(5H)-yl)phenyl]octahydropentalen-1-yl}malonate was prepared as follows. A slurry of 4-amino-6-(4-iodophenyl)-7,8-dihydro pyrimido[5,4-f][1,4]oxazepin-5(6H)-one (207 mg, 0.54 mmol), 1,5-cyclo octadiene (119 mg, 1.1 mmol), dimethylmalonate (347 mg, 2.6 mmol), tetra-N-butylammonium chloride (165 mg, 0.59 mmol), sodium bicarbonate (284 mg, 3.4 mmol) and dipalladium(0)tris(dibenzylideneacetone)-chloroform (26 mg, 0.02 mmol) in dimethylsulfoxide (6 mL) was stirred at 80° C. for 65 hr. The reaction mixture was cooled, concentrated and chromatographed to afford the title compound, 197 mg. ¹H NMR (400 MHz, CDCl₃) δ 8.25 (s, 1H), 7.29 (d, 2H), 7.18 (d, 2H), 4.65 (m, 2H), 3.75 (s, 3H), 3.72 (s, 3H), 3.38 (d, 1H), 2.80 (m, 1H), 2.43 (m, 2H), 1.97 (m, 1H), 1.75-1.32 (m, 7H). m/z=495.3 (M+1).

Step 2. (±)-{(1R,3aS,4R,6aS)-4-[4-(4-Amino-5-oxo-7,8-dihydropyrimido[5,4-f][1,4]oxazepin-6(5H)-yl)phenyl]octahydropentalen-1-yl}malonic acid was prepared as follows. A solution of dimethyl(±)-{(1R,3aS,4R,6aS)-4-[4-(4-amino-5-oxo-7,8-dihydropyrimido[5,4-f][1,4]oxazepin-6(5H)-yl)phenyl]octahydropentalen-1-yl}malonate (190 mg, 0.38 mmol) and lithium hydroxide monohydrate (166 mg, 3.9 mmol) in p-dioxane/water (8:3-11 mL) was stirred at 50° C. for 3 hours. The reaction was concentrated to remove the p-dioxane, water (2 mL) added and the mixture extracted with EtOAc (5 mL). The aqueous layer was adjusted to pH~3 with 2N aqueous hydrochloric acid, the solids filtered and dried in vacuo to afford the title compound as a white solid, 179 mg. ¹H NMR (400 MHz, DMSO-d₆) δ 8.17 (s, 1H), 7.58 (br s, 2H), 7.13 (d, 2H), 7.10 (d, 2H), 4.57 (m, 2H), 3.95 (m, 2H), 3.08 (d, 1H), 2.64 (m, 1H), 2.39 (m, 2H), 2.24 (m, 1H), 1.87-1.10 (m, 7H). m/z=467.3 (M+1).

Step 3. The title compound was prepared as follows. A solution of (±)-{(1R,3aS,4R,6aS)-4-[4-(4-amino-5-oxo-7,8-dihydropyrimido[5,4-f][1,4]oxazepin-6(5H)-yl)phenyl]octahydropentalen-1-yl}malonic acid (87 mg, 0.19 mmol) in xylenes (3 mL) and dimethylsulfoxide (0.5 mL) was stirred at 150° C. for 2 hours. After cooling the reaction mixture was diluted in EtOAc, washed with water and a precipitate formed in the organic layer. This solid was filtered and dried under vacuum to afford the title compound as a white solid, 24 mg. ¹H NMR (400 MHz, DMSO-d₆) δ 8.17 (s, 1H), 7.60 (br s, 2H), 7.15 (d, 2H), 7.12 (d, 2H), 4.58 (m, 2H), 3.96 (m, 2H), 3.13 (s, 1H), 2.62-1.12 (m, 13H). m/z=423.3 (M+1). IC₅₀<10 nM (range <3-27.2 nM).

Example 56

(1R,5R,6S)-6-[4-(4-Amino-5-oxo-7,8-dihydro-5H-9-oxa-1,3,6-triaza-benzo cyclohepten-6-yl)-phenyl]-tricyclo[3.2.1.0*2,4*]octane-3-carboxylic Acid Methyl Ester

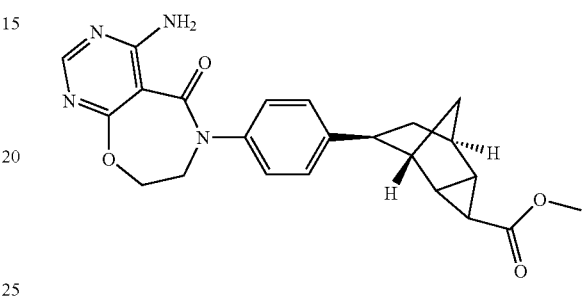

The named was prepared as follows. A slurry of 4-amino-6-(4-iodophenyl)-7,8-dihydropyrimido[5,4-f][1,4]oxazepin-5(6H)-one (340 mg, 0.89 mmol), tricycle[3.2.1.0*2,4*]oct-6-ene-3-carboxylic acid ethyl ester (240 mg, 1.35 mmol), tetrabutylammonium iodide (67 mg, 0.18 mmol), piperidine (230 mg, 2.7 mmol), formic acid (170 mg, 0.14 mmol) and dichlorobis(acetonitrile) palladium(II) (23 mg, 0.09 mmol) in DMF (0.36 mL) was stirred at 125° C. for 16 hours. The reaction mixture was cooled, diluted into EtOAc, washed with water, saturated aqueous brine, dried over magnesium sulfate and concentrated in vacuo to afford an oil. Chromatography (20 g of silica gel, 1-5% methanol:chloroform) afforded a solid, 127 mg. IC₅₀ 78.3 nM.

Example 57

(±)-(1R,5R,6S)-6-[4-(4-Amino-5-oxo-7,8-dihydro-pyrimido[5,4-f][1,4]oxazepin-6(5H)-yl)phenyl]tricyclo[3.2.1.0~2.4~]octane-3-carboxylic Acid

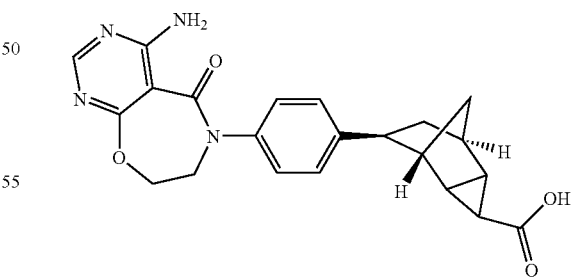

The title compound was prepared from the compound of Example 56 by hydrolyzing the ester as described in Example 2 to afford an off-white solid, 27 mg. ¹H NMR (400 MHz, DMSO-d₆) δ 8.19 (s, 1H), 7.75 (br s, 2H), 7.24 (m, 4H), 4.60 (m, 2H), 3.97 (m, 2H), 2.89 (s, 1H), 2.42 (m, 1H), 1.83 (m, 2H), 1.60 (m, 2H), 1.38 (AB pattern, 2H), 0.90 (s, 2H). m/z=407.4 (M+1). IC₅₀ 34.7 nM (range 26.7-58.6 nM).

Biological Protocols

The utility of the compounds of formula (1), the pharmaceutically acceptable salts of the compounds, (such as are described herein) in animals, particularly mammals (e.g., humans) may be demonstrated by the activity thereof in conventional assays known to one of ordinary skill in the relevant art, including the in vitro and in vivo assays discussed below. Such assays also provide a means whereby the activities of the compounds of formula (1) can be compared with the activities of other known compounds.

In Vitro Assay for DGAT-1 Inhibition

Human full-length diacylglycerol:acylCoA acyltransferase 1 (DGAT-1) was expressed in Sf9 insect cells which are then lysed and a crude membrane fraction (105,000×g pellet) was prepared. The DGAT-1 gene is a human DGAT-1 gene described in J. Biol. Chem. 273:26765, 1998 and U.S. Pat. No. 6,100,077.

In vitro inhibition of DGAT-1 was measured using a modification, further described below, of the assay methodology described in U.S. Pat. No. 6,994,956 B2.

The cells were cultured as follows. Sf9 cells (20 L) were infected with 4 mL of DGAT1 Baculovirus Infected Insect Cells (BIIC) for 72 hours in a Wave Bioreactor System 20/50P (Wave Biotec/GE Healthcare).

Crude DGAT-1 microsomes were prepared as follows. Cell pellets were washed once with ice-cold Dulbecco's phosphate-buffered saline. Cells were collected in tabletop centrifuge (Beckman GS-6KR), 15 minutes, 2000×g, 4° C. Twenty (20) mL of ice-cold Microsome Buffer (MB) was added per 5 g of cell pellet. The suspension was passed through a microfluidizer 3 times (18K psi). The lysate was transferred to centrifuge tubes and centrifuged for 20 minutes at 5000×g (Beckman-Coulter, Inc. Allegra® 64R High-Speed Refrigerated Benchtop Centrifuge, F0650 rotor) at 4° C. The supernatant was transferred to Ultracentrifuge tubes and centrifuged at 125,000×g for 1 hr in a Beckman Ti-45 rotor, 4° C. The supernatant fluid was discarded. The pellet was resuspended in 70 mL of MB by sonication. The microsome concentration was determined using Bio-Rad Protein DC Protein Assay. The microsomes were filter sterilized with a 0.22 µm filter. The samples were portioned, flash frozen and stored at −80° C.

The Microsome Buffer, used for microsome preparation, was prepared by conventional means and contained 125 mM sucrose, 3 mM imidazole, 0.2 µg/mL aprotinin, 0.2 µg/mL leupeptin and 5 mM dithiothreitol (Cleland's reagent), DGAT-1 activity was measured in 384-well format in a total assay volume of 25 µl that contained, Hepes buffer (50 mM, pH 7.5), $MgCl_2$ (10 mM), bovine serum albumin (0.6 mg/ml), [$^{14}$C]decanoylCoA (20 µM, 58 Ci/mol) and membranes (25 µg/ml) into which 1,2 dioleoyl-sn-glycerol (75 µM) in acetone has already been incorporated. Inhibitors in DMSO were pre-incubated with membranes before initiating the DGAT-1 reaction by the addition of decanoylCoA. Two control DGAT-1 reactions were also incubated in parallel: 1) DMSO without inhibitor to measure zero percent effect of inhibition and 2) and a maximally inhibited DGAT-1 reaction ("blank") incubated with 1 µM {trans-4-[4-(4-amino-2,7,7-trimethyl-7H-pyrimido[4,5-b][1,4]oxazin-6-yl)phenyl]cyclohexyl}acetic acid (WO2004/047755). The DMSO concentration was 2.5%. The inhibitors were present at a range of eight concentrations to generate an apparent $IC_{50}$ for each compound. The eight inhibitor concentration employed ranged from 10 µM to 3 nM (from high to low concentration). Specifically, the eight concentrations used were 10 µM, 3 µM, 1 µM, 300 nM, 100 nM, 30 nM, 10 nM and 3 nM.

The reactions were allowed to proceed for 1.5 h at room temperature and then terminated by the addition of 10 µl of HCl (0.5 M). Reaction mixtures were neutralized by the addition of 15 µl of tris(hydroxy-methyl)aminomethane (1M, pH 8.0) and then mixed by trituration with 37.5 µl of Microscint™-E (Perkin Elmer). Plates contents were allowed to partition for 15 to 30 min before $^{14}$C was measured in a scintillation spectrometer (Wallac Microbeta Trilux 1450-030 liquid scintillation counter 12 detector in the top-count DPM mode). Percent inhibition of test compounds was computed as 100−((DPM DMSO uninhibited−DPM test compound)/(DPM DMSO uninhibited)).

The compounds of the present invention, described in Examples 1-3 and 5-57, were tested for in vitro DGAT-1 inhibition, and were found to generally exhibit DGAT-1 inhibition with $IC_{50}$ values of 1000 nM or less. Where this DGAT-1 inhibition assay was performed on a compound more than once, an inhibition range is also provided for that compound. Preferably, the compounds of the present invention exhibit DGAT-1 inhibition with $IC_{50}$ values of 100 nM or less.

In Vivo Assay for Glucose Lowering

Oral glucose tolerance tests ("OGTT") have been in use in humans since, at least, the 1930s, Pincus et al., Am. J. Med. Sci, 188: 782 (1934), and are routinely used in the diagnosis of human diabetes, though not to evaluate the efficacy of therapeutic agents in patients.

KK mice have been used to evaluate glitazones (Fujita et al. Diabetes 32:804-810 (1983); Fujiwara et al., Diabetes 37: 1549-48 (1988); Izumi et al. Biopharm Durg. Dispos. 18:247-257 (1997)), metformin (Reddi et al. Diabet. Metabl. 19:44-51 (1993)), glucosidase inhibitors (Hamada et al. Jap. Pharmacol. Ther. 17:17-28 (1988); Matsuo et al. Am. J. Clin. Nutr. 55:314 S-317S (1992)), and the extra-pancreatic effects of sulfonylureas (Kameda et al Arzenim. Forsch./Drug Res. 32:39044 (1982); Muller et al. Horm. Metabl. Res. 28:469-487 (199)).

KK mice are derived from an inbred line first established by Kondo et al. (Kondo et al. Bull. Exp. Anim. 6:107-112 (1957)). The mice spontaneously develop a hereditary form of polygenic diabetes that progresses to cause renal, retinal and neurological complications analogous to those seen in human diabetic subjects, but they do not require insulin or other medication for survival. Another aspect of the invention is directed to the use of KK mice to evaluate the effects of insulin secretagogue agents in the context of an oral glucose tolerance test.

In Vivo Assay for Food Intake

The following screen may be used to evaluate the efficacy of test compounds for inhibiting food intake in Sprague-Dawley rats after an overnight fast.

Male Sprague-Dawley rats are individually housed and fed powdered chow. They are maintained on a 12 hour light/dark cycle and received food and water ad libitum. The animals are acclimated to the vivarium for a period of one week before testing is conducted. Testing is completed during the light portion of the cycle.

To conduct the food intake efficacy screen, rats are transferred to individual test cages without food the afternoon prior to testing, and the rats are fasted overnight. After the overnight fast, rats are dosed the following morning with vehicle or test compounds. A known antagonist is dosed (3 mg/kg) as a positive control, and a control group receives vehicle alone (no compound). The test compounds are dosed at ranges between 0.1 and 100 mg/kg depending upon the compound. The standard vehicle is 0.5% (w/v) methylcellulose in water and the standard route of administration is oral. However, different vehicles and routes of administration may be used to accommodate various compounds when required. Food is provided to the rats 30 minutes after dosing and an Oxymax automated food intake system (Columbus Instruments, Columbus, Ohio) is started. Individual rat food intake is recorded continuously at 10-minute intervals for a period of two hours. When required, food intake is recorded manually using an electronic scale; food is weighed every 30 minutes after food is provided up to four hours after food is provided. Compound efficacy is determined by comparing the food intake pattern of compound-treated rats to vehicle and the standard positive control.

We claim:

1. A compound having the formula

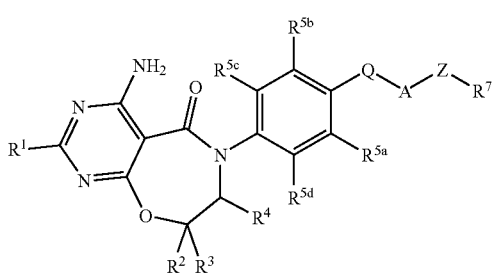

(1)

or a tautomer thereof, or a pharmaceutically acceptable salt of said compound or tautomer, wherein:
(a) $R^1$ is H —$(C_1-C_4)$alkyl, —$(C_1-C_4)$perfluoroalkyl, —$(C_1-C_4)$perfluoroalkoxy, or —$(C_1-C_4)$alkoxy;
(b) $R^2$ and $R^3$, taken separately, are independently H, —$(C_1-C_4)$alkyl, or —$(C_1-C_4)$perfluoroalkyl;
or $R^2$ and $R^3$, taken together with the carbon to which they are attached, is —$(C_3-C_6)$cycloalkyl;
(c) $R^4$ is H or —$(C_1-C_4)$alkyl;
(d) $R^{5a}$, $R^{5b}$, $R^{5c}$ and $R^{5d}$ are each independently H, F, Cl, Br, —$(C_1-C_4)$alkyl, —OH or —O—$(C_1-C_4)$alkyl;
(e) Q is —O— or a bond;
(f) A is a —$(C_3-C_6)$cycloalkylene group, a —$(C_3-C_6)$cycloalkenylene group or phenylene;
(g) Z is —$C(R^{6a})(R^{6b})$— or a bond wherein $R^{6a}$ and $R^{6b}$ are each independently —H or —$(C_1-C_4)$alkyl, or $R^{6a}$ and $R^{6b}$, taken together with the carbon to which they are attached, is a —$(C_3-C_6)$cycloalkyl;
(h) $R^7$ is C(O)$R^8$, cyano, hydroxyl, —$(C_1-C_4)$alkoxy, —$(C_1-C_4)$perfluoroalkoxy or a carboxylic acid mimic;
(i) $R^8$ is —$OR^9$ or $NHR^{10}$;
(j) $R^9$ is —H, —$(C_1-C_4)$alkyl, or —$(C_1-C_4)$perfluoroalkyl; and
(k) $R^{10}$ is —H, —$(C_1-C_4)$alkyl, tetrazolyl or $S(O)_2CF_3$.

2. The compound of claim 1, or a tautomer thereof, or pharmaceutically acceptable salt of said compound or tautomer, wherein
(a) $R^1$, $R^2$, $R^3$ and $R^4$ are each independently H or —$CH_3$;
(b) $R^{5b}$ and $R^{5c}$ are each H;
(c) $R^{5d}$ is H, F or Cl;
(d) $R^{5a}$ is H, F, Cl or methyl;
(e) Z is —$CH_2$— or a bond, and
(f) $R^7$ is C(O)$R^8$ or cyano.

3. The compound of claim 2, or a tautomer thereof, or pharmaceutically acceptable salt of said compound or tautomer, wherein:

Q is a bond; and
A is a —$(C_3-C_{10})$cycloalkylene group or a —$(C_3-C_{10})$cycloalkenylene group.

4. The compound of claim 3, or a tautomer thereof, or pharmaceutically acceptable salt of said compound or tautomer, wherein $R^{5d}$ is H.

5. The compound of claim 4, or a tautomer thereof, or pharmaceutically acceptable salt of said compound or tautomer, wherein A is 1,4-cyclohexylene, cyclohex-3-en-1,4-di-yl, tricyclo[3.2.1.0~2,4~]octylene-1,3-di-yl or octahydropentalene-1,4-di-yl.

6. A compound of claim 5, having the formula

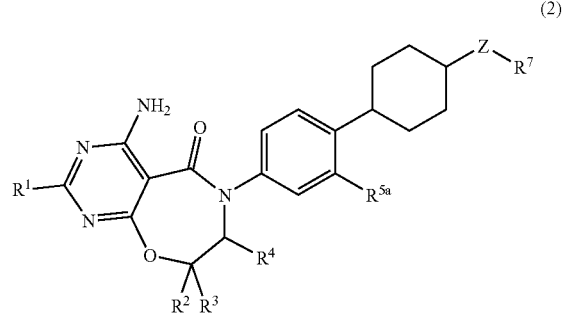

(2)

or a tautomer thereof, or a pharmaceutically acceptable salt of said compound or tautomer, wherein:
$R^1$ is H or —$CH_3$;
$R^2$ is H or —$CH_3$;
$R^3$ is H or —$CH_3$;
$R^4$ is H or —$CH_3$;
$R^{5a}$ is H, F, Cl or methyl;
Z is —$C(R^{6a})(R^{6b})$— or a bond wherein $R^{6a}$ and $R^{6b}$ are each independently —H or —$(C_1-C_4)$alkyl, or $R^{6a}$ and $R^{6b}$, taken together with the carbon to which they are attached, is a —$(C_3-C_6)$cycloalkyl;
$R^7$ is C(O)$R^8$, cyano, hydroxyl, —$(C_1-C_4)$alkoxy, —$(C_1-C_4)$perfluoroalkoxy or a carboxylic acid mimic;
$R^8$ is —$OR^9$ or $NHR^{10}$;
$R^9$ is —H, —$(C_1-C_4)$alkyl, or —$(C_1-C_4)$perfluoroalkyl; and
$R^{10}$ is —H, —$(C_1-C_4)$alkyl, tetrazolyl or $S(O)_2CF_3$.

7. The compound of claim 6, or a tautomer thereof, or pharmaceutically acceptable salt of said compound or tautomer, wherein Z is —$CH_2$—.

8. The compound of claim 7, or a tautomer thereof, or pharmaceutically acceptable salt of said compound or tautomer, wherein $R^7$ is —C(O)$NHR^{10}$.

9. The compound of claim 7, or a tautomer thereof, or pharmaceutically acceptable salt of said compound or tautomer, wherein $R^7$ is —CN.

10. The compound of claim 9 which is {trans-4-[4-(4-amino-5-oxo-7,8-dihydropyrimido[5,4-f][1,4]oxazepin-6 (5H)-yl]phenyl]cyclohexyl}acetonitrile or a tautomer thereof, or pharmaceutically acceptable salt of said compound or tautomer.

11. The compound of claim 7, or a tautomer thereof, or pharmaceutically acceptable salt of said compound or tautomer, wherein $R^7$ is —C(O)OH.

12. The compound of claim 11 which is 2-(4-(4-(4-amino-5-oxo-7,8-dihydropyrimido[5,4-f][1,4]oxazepin-6(5H)-yl)-2-fluorophenyl)cyclohexyl)acetic acid or a tautomer thereof, or pharmaceutically acceptable salt of said compound or tautomer.

13. The compound of claim 11 which is {trans-4-[4-(4-amino-5-oxo-7,8-dihydropyrimido[5,4-f][1,4]oxazepin-6(5H)-yl)phenyl]cyclohexyl}acetic acid or a tautomer thereof, or pharmaceutically acceptable salt of said compound or tautomer.

14. The compound of claim 7, or a tautomer thereof, or pharmaceutically acceptable salt of said compound or tautomer wherein $R^2$ is (R)-methyl.

15. The compound of claim 14, or a tautomer thereof, or pharmaceutically acceptable salt of said compound or tautomer, wherein $R^7$ is —CN.

16. The compound of claim 14 which is (trans-4-{4-[(8R)-4-amino-8-methyl-5-oxo-7,8-dihydropyrimido[5,4-f][1,4]oxazepin-6(5H)-yl]phenyl}cyclohexyl)acetonitrile or a tautomer thereof, or pharmaceutically acceptable salt of said compound or tautomer.

17. The compound of claim 14, or a tautomer thereof, or pharmaceutically acceptable salt of said compound or tautomer, wherein $R^7$ is —C(O)OH.

18. The compound of claim 17 which is (trans-4-{4-[(8R)-4-amino-8-methyl-5-oxo-7,8-dihydropyrimido[5,4-f][1,4]oxazepin-6(5H)-yl]phenyl}cyclohexyl)acetic acid or a tautomer thereof, or pharmaceutically acceptable salt of said compound or tautomer.

19. The compound of claim 17 which is (R)-2-(4-(4-(4-amino-8-methyl-5-oxo-7,8-dihydropyrimido[5,4-f][1,4]oxazepin-6(5H)-yl)-2-fluorophenyl)-cyclohexyl)acetic acid or a tautomer thereof, or pharmaceutically acceptable salt of said compound or tautomer.

20. A pharmaceutical composition comprising:
(a) a compound having the formula (1)

or a tautomer thereof, or a pharmaceutically acceptable salt of said compound or tautomer, wherein:
$R^1$ is H —($C_1$-$C_4$)alkyl, —($C_1$-$C_4$)perfluoroalkyl, —($C_1$-$C_4$)perfluoroalkoxy, or —($C_1$-$C_4$)alkoxy;
$R^2$ and $R^3$, taken separately, are independently H, —($C_1$-$C_4$)alkyl, or —($C_1$-$C_4$)perfluoroalkyl;
or $R^2$ and $R^3$, taken together with the carbon to which they are attached, is —($C_3$-$C_6$)cycloalkyl;
$R^4$ is H or —($C_1$-$C_4$)alkyl;
$R^{5a}$, $R^{5b}$, $R^{5c}$ and $R^{5d}$ are each independently H, F, Cl, Br, —($C_1$-$C_4$)alkyl, —OH or —O—($C_1$-$C_4$)alkyl;
Q is —O— or a bond;
A is a —($C_3$-$C_6$)cycloalkylene group, a —($C_3$-$C_6$)cycloalkenylene group or phenylene;
Z is —C($R^{6a}$)($R^{6b}$)— or a bond wherein $R^{6a}$ and $R^{6b}$ are each independently —H or —($C_1$-$C_4$)alkyl, or $R^{6a}$ and $R^{6b}$, taken together with the carbon to which they are attached, is a —($C_3$-$C_6$)cycloalkyl;
$R^7$ is C(O)$R^8$, cyano, hydroxyl, —($C_1$-$C_4$)alkoxy, —($C_1$-$C_4$)perfluoroalkoxy or a carboxylic acid mimic;
$R^8$ is —O$R^9$ or NH$R^{10}$;

$R^9$ is —H, —($C_1$-$C_4$)alkyl, or —($C_1$-$C_4$)perfluoroalkyl; and
$R^{10}$ is —H, —($C_1$-$C_4$)alkyl, tetrazolyl or S(O)$_2$CF$_3$; and
(b) a pharmaceutically acceptable carrier, vehicle, diluent or excipient.

21. The pharmaceutical composition of claim 20 comprising:
(a) a compound having the formula (2)

or a tautomer thereof, or a pharmaceutically acceptable salt of said compound or tautomer, wherein:
$R^1$ is H or —CH$_3$;
$R^2$ is H or —CH$_3$;
$R^3$ is H or —CH$_3$;
$R^4$ is H or —CH$_3$;
$R^{5a}$ is H, F, Cl or methyl;
A is 1,4-cyclohexylene;
Z is —C($R^{6a}$)($R^{6b}$)— or a bond wherein $R^{6a}$ and $R^{6b}$ are each independently —H or —($C_1$-$C_4$)alkyl, or $R^{6a}$ and $R^{6b}$, taken together with the carbon to which they are attached, is a —($C_3$-$C_6$)cycloalkyl;
$R^7$ is C(O)$R^8$, cyano, hydroxyl, —($C_1$-$C_4$)alkoxy, —($C_1$-$C_4$)perfluoroalkoxy or a carboxylic acid mimic;
$R^8$ is —O$R^9$ or NH$R^{10}$;
$R^9$ is —H, —($C_1$-$C_4$)alkyl, or —($C_1$-$C_4$)perfluoroalkyl; and
$R^{10}$ is —H, —($C_1$-$C_4$)alkyl, tetrazolyl or S(O)$_2$CF$_3$; and
(b) a pharmaceutically acceptable carrier, vehicle, diluent or excipient.

22. A method for treating Type 2 diabetes in a mammal in need of such treatment comprising administering to said mammal a therapeutically effective amount of a compound having the formula (1)

or a tautomer thereof, or a pharmaceutically acceptable salt of said compound or tautomer, wherein:
$R^1$ is H —($C_1$-$C_4$)alkyl, —($C_1$-$C_4$)perfluoroalkyl, —($C_1$-$C_4$)perfluoroalkoxy, or —($C_1$-$C_4$)alkoxy;

$R^2$ and $R^3$, taken separately, are independently H, —($C_1$-$C_4$)alkyl, or —($C_1$-$C_4$)perfluoroalkyl;

or $R^2$ and $R^3$, taken together with the carbon to which they are attached, is —($C_3$-$C_6$)cycloalkyl;

$R^4$ is H or —($C_1$-$C_4$)alkyl;

$R^{5a}$, $R^{5b}$, $R^{5c}$ and $R^{5d}$ are each independently H, F, Cl, Br, —($C_1$-$C_4$)alkyl, —OH or —O—($C_1$-$C_4$)alkyl;

Q is —O— or a bond;

A is a —($C_3$-$C_6$)cycloalkylene group, a —($C_3$-$C_6$)cycloalkenylene group or phenylene;

Z is —C($R^{6a}$)($R^{6b}$)— or a bond wherein $R^{6a}$ and $R^{6b}$ are each independently —H or —($C_1$-$C_4$)alkyl, or $R^{6a}$ and $R^{6b}$, taken together with the carbon to which they are attached, is a —($C_3$-$C_6$)cycloalkyl;

$R^7$ is C(O)$R^8$, cyano, hydroxyl, —($C_1$-$C_4$)alkoxy, —($C_1$-$C_4$)perfluoroalkoxy or a carboxylic acid mimic;

$R^8$ is —O$R^9$ or NH$R^{10}$;

$R^9$ is —H, —($C_1$-$C_4$)alkyl, or —($C_1$-$C_4$)perfluoroalkyl; and $R^{10}$ is —H, —($C_1$-$C_4$)alkyl, tetrazolyl or S(O)$_2$CF$_3$.

23. A method of claim 22 for treating Type 2 diabetes in a mammal in need of such treatment comprising administering to said mammal a therapeutically effective amount of a compound having the formula

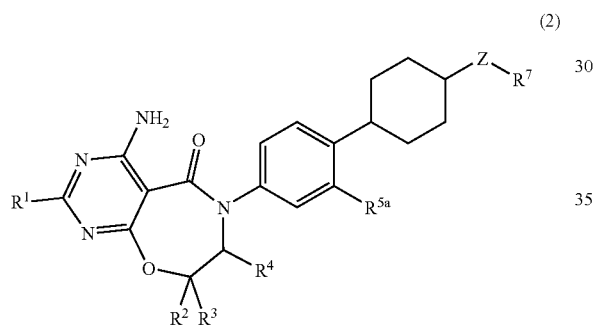

(2)

or a tautomer thereof, or a pharmaceutically acceptable salt of said compound or tautomer, wherein:

$R^1$ is H or —CH$_3$;

$R^2$ is H or —CH$_3$;

$R^3$ is H or —CH$_3$;

$R^4$ is H or —CH$_3$;

$R^{5a}$ is H, F, Cl or methyl;

A is 1,4-cyclohexylene;

Z is —C($R^{6a}$)($R^{6b}$)— or a bond wherein $R^{6a}$ and $R^{6b}$ are each independently —H or —($C_1$-$C_4$)alkyl, or $R^{6a}$ and $R^{6b}$, taken together with the carbon to which they are attached, is a —($C_3$-$C_6$)cycloalkyl;

$R^7$ is C(O)$R^8$, cyano, hydroxyl, —($C_1$-$C_4$)alkoxy, —($C_1$-$C_4$)perfluoroalkoxy or a carboxylic acid mimic;

$R^8$ is —O$R^9$ or NH$R^{10}$;

$R^9$ is —H, —($C_1$-$C_4$)alkyl, or —($C_1$-$C_4$)perfluoroalkyl; and $R^{10}$ is —H, —($C_1$-$C_4$)alkyl, tetrazolyl or S(O)$_2$CF$_3$.

24. The method of claim 23 wherein said mammal is a human.

25. A method for treating obesity in a mammal in need of such treatment comprising administering to said mammal a therapeutically effective amount of a compound having the formula

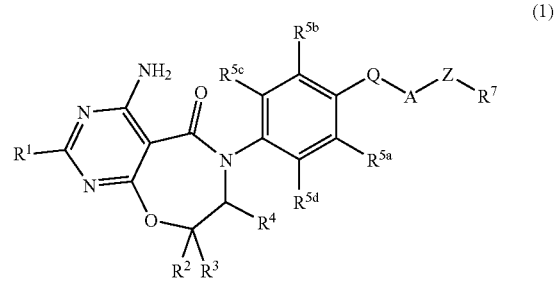

(1)

or a tautomer thereof, or a pharmaceutically acceptable salt of said compound or tautomer, wherein:

$R^1$ is H —($C_1$-$C_4$)alkyl, —($C_1$-$C_4$)perfluoroalkyl, —($C_1$-$C_4$)perfluoroalkoxy, or —($C_1$-$C_4$)alkoxy;

$R^2$ and $R^3$, taken separately, are independently H, —($C_1$-$C_4$)alkyl, or —($C_1$-$C_4$)perfluoroalkyl;

or $R^2$ and $R^3$, taken together with the carbon to which they are attached, is —($C_3$-$C_6$)cycloalkyl;

$R^4$ is H or —($C_1$-$C_4$)alkyl;

$R^{5a}$, $R^{5b}$, $R^{5c}$ and $R^{5d}$ are each independently H, F, Cl, Br, —($C_1$-$C_4$)alkyl, —OH or —O—($C_1$-$C_4$)alkyl;

Q is —O— or a bond;

A is a —($C_3$-$C_6$)cycloalkylene group, a —($C_3$-$C_6$)cycloalkenylene group or phenylene;

Z is —C($R^{6a}$)($R^{6b}$)— or a bond wherein $R^{6a}$ and $R^{6b}$ are each independently —H or —($C_1$-$C_4$)alkyl, or $R^{6a}$ and $R^{6b}$, taken together with the carbon to which they are attached, is a —($C_3$-$C_6$)cycloalkyl;

$R^7$ is C(O)$R^8$, cyano, hydroxyl, —($C_1$-$C_4$)alkoxy, —($C_1$-$C_4$)perfluoroalkoxy or a carboxylic acid mimic;

$R^8$ is —O$R^9$ or NH$R^{10}$;

$R^9$ is —H, —($C_1$-$C_4$)alkyl, or —($C_1$-$C_4$)perfluoroalkyl; and $R^{10}$ is —H, —($C_1$-$C_4$)alkyl, tetrazolyl or S(O)$_2$CF$_3$.

26. A method of claim 25 for treating obesity in a mammal in need of such treatment comprising administering to said mammal a therapeutically effective amount of a compound having the formula

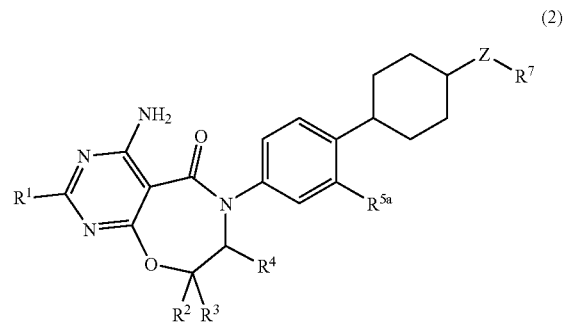

(2)

or a tautomer thereof, or a pharmaceutically acceptable salt of said compound or tautomer, wherein:

$R^1$ is H or —CH$_3$;

$R^2$ is H or —CH$_3$;

$R^3$ is H or —CH$_3$;

$R^4$ is H or —CH$_3$;

$R^{5a}$ is H, F, Cl or methyl;

A is 1,4-cyclohexylene;

Z is —C($R^{6a}$)($R^{6b}$)— or a bond wherein $R^{6a}$ and $R^{6b}$ are each independently —H or —($C_1$-$C_4$)alkyl, or $R^{6a}$ and $R^{6b}$, taken together with the carbon to which they are attached, is a —($C_3$-$C_6$)cycloalkyl;

$R^7$ is C(O)$R^8$, cyano, hydroxyl, —($C_1$-$C_4$)alkoxy, —($C_1$-$C_4$)perfluoroalkoxy or a carboxylic acid mimic;

$R^8$ is —O$R^9$ or NH$R^{10}$;

$R^9$ is —H, —($C_1$-$C_4$)alkyl, or —($C_1$-$C_4$)perfluoroalkyl; and $R^{10}$ is —H, —($C_1$-$C_4$)alkyl, tetrazolyl or S(O)$_2$CF$_3$.

27. The method of claim 26 wherein said mammal is a human.

* * * * *